United States Patent
Panzner et al.

(10) Patent No.: US 9,283,186 B2
(45) Date of Patent: Mar. 15, 2016

(54) AMPHOTERIC LIPOSOMES, A METHOD OF FORMULATING AN AMPHOTERIC LIPOSOME AND A METHOD OF LOADING AN AMPHOTERIC LIPOSOME

(75) Inventors: Steffen Panzner, Halle (DE); Silke Lutz, Halle (DE); Evgenios Siepi, Leipzig (DE); Claudia Müller, Nerchau (DE)

(73) Assignee: Marina Biotech, Inc., Bothell, WA (US)

( * ) Notice: Subject to any disclaimer, the term of this patent is extended or adjusted under 35 U.S.C. 154(b) by 1038 days.

(21) Appl. No.: 13/350,137

(22) Filed: Jan. 13, 2012

(65) Prior Publication Data
US 2012/0135065 A1    May 31, 2012

Related U.S. Application Data

(63) Continuation of application No. 11/974,350, filed on Oct. 12, 2007, now abandoned, which is a continuation-in-part of application No. 11/581,054, filed on Oct. 13, 2006, now abandoned.

(30) Foreign Application Priority Data

Oct. 13, 2006 (EP) .................................... 06255277

(51) Int. Cl.
*C07D 265/30*    (2006.01)
*A61K 9/127*    (2006.01)
(52) U.S. Cl.
CPC .................................... *A61K 9/1272* (2013.01)
(58) Field of Classification Search
CPC .............................. A61K 9/127; C07D 265/30
USPC ......................................... 424/450; 544/154
See application file for complete search history.

(56) References Cited

U.S. PATENT DOCUMENTS

| 5,296,231 A | 3/1994 | Yarosh |
| 5,302,389 A | 4/1994 | Kripke et al. |

(Continued)

FOREIGN PATENT DOCUMENTS

| DE | 19753182 A1 | 7/1999 |
| EP | 1392341 A2 | 3/2004 |

(Continued)

OTHER PUBLICATIONS

Cho-Chung et al. "Oligonucleotides as Transcription Factor Decoys." *Curr. Opin. Mol. Ther.* 1.3(1999):386-392.

(Continued)

*Primary Examiner* — Gollamudi Kishore
(74) *Attorney, Agent, or Firm* — Eckman Basu LLP

(57) ABSTRACT

An amphoteric liposome composed of a mixture of lipids, said mixture comprising a cationic amphiphile, an anionic amphiphile and optionally one or more neutral amphiphiles, at least one of said cationic and anionic amphiphiles being chargeable and the respective amounts of said cationic and anionic amphiphiles being selected such there is a stoichiometric excess of positively charged cationic amphiphile at a first lower pH, a stoichiometric excess of negatively charged anionic amphiphile at a second higher pH and said mixture has an isoelectric point intermediate said first and second pHs; characterised in that said positively charged cationic and negatively charged anionic amphiphiles are adapted to form a lipid salt with one another at said isoelectric point. Also disclosed are methods of predicting the fusogenicity of an amphoteric liposome at a given pH, formulating an amphoteric liposome and loading an amphoteric liposome with a cargo moiety.

18 Claims, 16 Drawing Sheets

(56) References Cited

U.S. PATENT DOCUMENTS

| | | | |
|---|---|---|---|
| 7,371,404 | B2 | 5/2008 | Panzner et al. |
| 7,780,983 | B2 | 8/2010 | Panzner et al. |
| 7,858,117 | B2 | 12/2010 | Panzner et al. |
| 2003/0099697 | A1 | 5/2003 | Panzner et al. |
| 2004/0037874 | A1 | 2/2004 | Hong et al. |
| 2006/0002991 | A1 | 1/2006 | Essler et al. |
| 2008/0088046 | A1 | 4/2008 | Panzner |
| 2008/0089932 | A1 | 4/2008 | Panzner et al. |
| 2010/0330154 | A1 | 12/2010 | Panzner et al. |

FOREIGN PATENT DOCUMENTS

| | | | |
|---|---|---|---|
| WO | 96/20208 | * | 7/1996 |
| WO | WO-9821322 A1 | | 5/1998 |
| WO | WO-9851278 A2 | | 11/1998 |
| WO | WO-9932619 A1 | | 7/1999 |
| WO | WO-02055693 A2 | | 7/2002 |
| WO | WO-02066012 A2 | | 8/2002 |
| WO | WO-02066489 A2 | | 8/2002 |
| WO | WO-2004047792 A2 | | 6/2004 |
| WO | WO-2005094783 A2 | | 10/2005 |
| WO | WO-2006047792 A1 | | 5/2006 |
| WO | WO-2006048329 A1 | | 5/2006 |
| WO | WO-2006053646 A2 | | 5/2006 |
| WO | WO-2007012191 A1 | | 2/2007 |
| WO | WO-2007031333 A2 | | 3/2007 |
| WO | WO-2007064857 A2 | | 6/2007 |
| WO | WO-2007107304 A2 | | 9/2007 |
| WO | WO-2008043575 A2 | | 4/2008 |
| WO | WO-2009047006 A2 | | 4/2009 |

OTHER PUBLICATIONS

Connolly. "Computation of Molecular Volume." *J. Am. Chem. Soc.* 107(1985):1118-1124.

Hafez et al. "Cholesteryl Hemisuccinate Exhibits pH Sensitive Polymorphic Phase Behavior," *Biochim. Biophys. Acta.* 1463(2000):107-114.

Hafez et al. "Tunable pH-Sensitive Liposomes Composed of Mixtures of Cationic and Anionic Lipids." *Biophys. J.* 79(2000):1438-1446.

Israelachvili et al. "Theory of Self-Assembly of Lipid Bilayers and Vesicles." *Biochim. Biophys. Acta.* 470(1977):185-201.

Israelachvili et al. "A Model for the Packing of Lipids in Bilayer Membranes." *Biochim. Biophys. Acta.* 389(1975):13-19.

Israelachvili et al. "Physical Principles of Membrane Organization." *Quart. Rev. Biophys.* 13.2(1980):121-200.

Kley et al. "Synthesis of Novel Thiol-Reactive Amphiphilic Lipids Based on Cholesterol for Protein-Liposome Coupling," *Monatsheft Chim.* 129(1998):319-327.

Li et al. "Theory of Tunable pH-Sensitive Vesicles of Anionic and Cationic Lipids or Anionic and Neutral Lipids." *Biophys. J.* 80(2001):1703-1711.

Pohle et al. "Comparative FTIR Spectroscopic Study Upon the Hydration of Lecithins and Cephalins," *J. Mol. Struct.* 408-409(1997):273-277.

Shi et al. "Efficient Intracellular Drug and Gene Delivery Using Folate Receptor-Targeted pH-Sensitive Liposomes Composed of Cationic/Anionic Lipid Combinations." *J. Controll. Rel.* 80(2002):309-319.

Straubinger et al. "pH-Sensitive Liposomes Mediate Cytoplasmic Delivery of Encapsulated Macromolecules." *FEBS.* 179.1(1985):148-154.

Wilson, Jr. et al. "Thiophenyl Malonate." *J. Org. Chem.* 39(1974):3170.

* cited by examiner

AMPHOTERIC LIPOSOMES, A METHOD OF FORMULATING AN AMPHOTERIC LIPOSOME AND A METHOD OF LOADING AN AMPHOTERIC LIPOSOME

CROSS-REFERENCE TO RELATED APPLICATIONS

This application is a continuation of U.S. patent application Ser. No. 11/974,350, filed Oct. 12, 2007, which is a continuation-in-part of U.S. patent application Ser. No. 11/581,054, filed on Oct. 13, 2006 and European Patent Application No: 06255277.3, also filed on Oct. 13, 2006.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates to improvements in or relating to amphoteric liposomes. In particular, the present invention provides a novel method for formulating such liposomes and a method for loading them, as well as liposomes produced by such methods.

BACKGROUND OF THE INVENTION

Amphoteric liposomes have been found to exhibit excellent biodistribution and to be well tolerated in animals. They can encapsulate active agents, including nucleic acid molecules, with high efficiency.

In contrast to zwitterionic structures, amphoteric liposomes advantageously have an isoelectric point and are negatively charged at higher pH values and positively charged at lower pH values. Amphoteric liposomes belong to the larger group of pH-sensitive liposomes that were introduced by Straubinger, et al. (FEES Lett., 1985, 179(1), 148-154). Typical pH-responsive elements in pH-sensitive liposomes are cholesterol hemisuccinate (CHEMS), palmitoylhomocysteine, dioleoylglycerol hemisuccinate (DOG-Succ) and the like. CHEMS can stabilise dioleoylphosphatidylethanolamine (DOPE), a lipid which preferentially adopts the inverted hexagonal phase at temperatures above 10° C., into the lamellar phase at pH 7.4. Lamellar CHEMS/DOPE systems can be prepared at neutral or slightly alkaline pH but these systems become unstable and fuse at acidic pH (Hafez and Cullis, Biochim. Biophys. Acta, 2000, 1463, 107-114).

Fusogenic liposomes are very useful in pharmaceutical applications, especially for the intracellular delivery of drugs, e.g., nucleic acids, such, for example, as plasmids and oligonucleotides. After the uptake of a liposome into a cell by endocytosis the release of the drug from the endosome is a crucial step for the delivery of a drug into the cytosol of cells.

The pH within an endosome is slightly acidic and therefore pH sensitive liposomes can fuse with the endosomal membrane and thereby allowing the release of the drug from the endosome. This means that destabilisation of the lipid phase, e.g., by enhanced fusogenicity, facilitates endosome escape and intracellular delivery. Also other environments of low pH can trigger the fusion of such liposomes, e.g., the low pH found in tumors or sites of inflammation.

Hafez, et al. (Biophys. J. 2000, 79(3), 1438-1446) were unsatisfied with the limited control over the pH at which such fusion occurs and demonstrated a rational approach to fine-tune the fusion point by adding cationic lipids. Such mixtures have true amphoteric properties in that they exist in a cationic state at low pH and as anionic particles at higher pH, typically at physiological pH. According to Hafez, et al. fusion starts at pH values where the net charge of the particles is zero (their isoelectric point), and once such point is crossed (the pH is lower to any extent) fusion is a continuous process. This view is shared by Li and Schick (Biophys. J., 2001, 80, 1703-1711) who analysed the fusion tendency for amphoteric lipid mixtures using a mathematical model.

Israelachvili and Mitchell in 1975 (Biochim. Biophys. Acta, 1975, 389, 13-19) introduced the molecular shape concept which assumes that the overall form of lipid molecules determines the structure of the hydrated lipid membrane. This means that the lipid geometry and more specifically the size ratio between the polar head-group and the hydrophobic membrane anchor is the key parameter determining the lipid phase (Israelachvili, et al. Biochim Biophys Acta. 1977 17; 470(2):185-201). The original theory however did not consider counterions being a steric part of the polar head-group, but this was contributed by Li and Schick (Biophys. J., 2001, 80, 1703-1711). In their description of the DODAC/CHEMS system, the sodium ion enlarges the head-group of CHEMS at neutral pH, but dissociates as the pH drops, thus minimising the head-group volume and promoting a hexagonal phase; DODAC as a strong cation is assumed to be in constant association with its respective counterion, irrespective of the pH. The model predicts fusion at some pH and below.

Lipid phases according to the molecular shape concept (Israelachvili et al., 1980, Q. Rev. Biophys., 13(2), 121-200):

| Shape | Organisation | Lipid phase | Examples |
| --- | --- | --- | --- |
| Inverted cone | Micelles | Isotropic Hexagonal I | Detergents Lysophopholipids |
| Cylinder | Bilayer | Lamellar (Cubic) | PC, PS, PI, SM |
| Cone | Reverse micelles | Hexagonal II | PE, PA at low pH or with Ca2+, Cholesterol, Cardiolipin |

The addition of neutral lipids to amphoteric lipid mixtures has been found to have little impact on the isoelectric point of amphoteric liposomes. WO 02/066012 (Panzner, et al.) discloses certain amphoteric liposomes comprising neutral lipids with a stable size at both low and neutral pHs. WO 02/066012 also describes a method of loading such particles with nucleic acids starting from a low pH.

Amphoteric liposomes are complex structures and comprise at least a complementary pair of charged lipids. The inclusion of one or more such neutral lipids significantly adds to the complexity of the mixture, especially since the individual amounts of the components may vary. Hafez, et al. (Biophys. J. 2000, 79(3), 1438-1446) and WO 02/066012 provide some guidance as to how to select lipid mixtures with truly amphoteric properties and more specifically how to determine their isoelectric point and onset of fusion. Nevertheless, the very high number of possible combinations of lipids represents a practical hurdle towards a more rapid optimisation of amphoteric liposomes, and there remains a need in the art for a method of predicting or analysing which mixtures of lipids form satisfactorily stable lamellar phases at high and low pH, whilst forming a fusogenic, hexagonal phase at an intermediate pH.

It is an object of the present invention therefore to provide improved methods for formulating such fusogenic amphoteric liposomes. Amphoteric liposomes that form a stable lipid phase at neutral pH and a fusogenic phase at low pH represent another object of the invention. Yet another object of the invention is the provision of amphoteric liposomes that form stable lipid phases both at low pH and at neutral pH, but undergo fusion at an intermediate pH. The inventors have recognised that it would be desirable to control the pH at which an amphoteric liposome is fusogenic, so as to enable the liposome to be better targeted in some applications to the endosomal environment where its cargo is desired to be released. Yet another object of the invention therefore is to provide a way of controlling the pH at which fusion of such amphoteric liposomes occurs.

SUMMARY OF THE INVENTION

According to one aspect of the present invention therefore there is provided a method of formulating amphoteric liposomes comprising:

(i) selecting an anionic amphiphile, a cationic amphiphile, each of said anionic and cationic amphiphiles having respective polar head and apolar tail-groups, cationic and anionic counterions for said anionic and cationic amphiphiles respectively, and optionally one or more neutral amphiphiles, at least one of said anionic and cationic amphiphiles being chargeable;

(ii) calculating the κ values for each of said anionic and cationic amphiphiles, when uncharged and when charged and associated respectively with said cationic and anionic counterions, and said one or more optional neutral amphiphiles and the $\kappa_{salt}$ value for a lipid salt comprising said anionic and cationic amphiphiles in charged form, κ being the ratio of the molecular volume of the polar head-group $V_{head}$ to the molecular volume of the apolar tail-group $V_{apolar}$ of the respective species, the molecular volumes of the polar head-groups of the charged anionic and cationic amphiphiles including the respective counterions, $\kappa_{salt}$ being defined as:

$$\kappa_{salt} = \frac{V_{head}(cat) + V_{head}(an)}{V_{apolar}(cat) + V_{apolar}(an)}$$

wherein $V_{head}$ (cat) is the molecular volume of the polar head-group of the cationic amphiphile without the respective counter-anion, $V_{head}$ (an) is the molecular volume of the polar head-group of the anionic amphiphile without the respective counter-cation, $V_{apolar}$(cat) is the molecular volume of the apolar tail-group of the cationic amphiphile and $V_{apolar}$(an) is the molecular volume of the apolar tail-group of the anionic amphiphile;

(iii) modelling the function $\kappa_{total}$(pH) for a lipid mixture of said anionic and cationic amphiphiles and said one or more optional neutral amphiphiles, assuming said cationic and anionic amphiphiles form said lipid salt when charged, the respective amounts of said amphiphiles in said lipid mixture being chosen such that said mixture of lipids has an isoelectric point between a first lower pH and a second higher pH and has a stoichiometric excess of positively charged cationic amphiphile at said first pH and a stoichiometric excess of negatively charged anionic amphiphile at said second pH, $\kappa_{total}$ (pH) being defined as:

$$K_{total}(pH) = K_{an} \cdot c_{an}(pH) + K_{cat} \cdot c_{cat}(pH) + K_{an-} \cdot c_{an-}(pH) + K_{cat+} \cdot c_{cat+}(pH) + K_{salt} \cdot c_{salt}(pH) + \Sigma \kappa_n \cdot c_n$$

wherein $c_{an}$(pH), $c_{cat}$(pH), $c_{an-}$(pH), $c_{cat+}$(pH) and $c_{salt}$ (pH) are the respective concentrations in the lipid mixture of the uncharged anionic, uncharged cationic, charged anionic and charged cationic amphiphiles and said lipid salt as a function of pH, $c_n$ is the concentration in the lipid mixture of the or each optional neutral amphiphile, and $\kappa_{an}, \kappa_{cat}, \kappa_{an-}, \kappa_{cat+}, \kappa_{salt}$ and $\kappa_n$ are the respective κ values for the uncharged anionic, uncharged cationic, charged anionic and charged cationic amphiphiles, said lipid salt and the or each optional neutral amphiphile;

(iv) determining that $\kappa_{total}$(pH) exhibits a minimum at said isoelectric point;

(v) making liposomes composed of said lipid mixture and empirically confirming that said mixture exhibits a stable lamellar phases at said second pH and, optionally, at said first pH and a fusogenic, hexagonal phase at or around said isoelectric point; and thereafter (vi) manufacturing an amphoteric liposome composed of said lipid mixture.

Suitably said molecular volumes may be calculated by molecular modelling.

Said mixture may have an isoelectric point in the range pH 4 to pH 8, preferably in the range pH 5 to pH 7.

Suitably, said first pH may be in the range pH 4 to pH 5 or in the range pH 2 to pH 4. Said second pH may be in the range pH 7 to pH 8. Advantageously, said second pH is about physiological pH (about pH 7.4).

According to another aspect of the present invention there is provided an amphoteric liposome composed of a mixture of lipids, said mixture comprising a cationic amphiphile, an anionic amphiphile and optionally one or more neutral amphiphiles, at least one of said cationic and anionic amphiphiles being chargeable and the respective amounts of said cationic and anionic amphiphiles being selected such there is a stoichiometric excess of positively charged cationic amphiphile at a first lower pH, a stoichiometric excess of negatively charged anionic amphiphile at a second higher pH, and said mixture has an isoelectric point intermediate said first and second pHs; characterised in that said positively charged cationic and negatively charged anionic amphiphiles are adapted to form a lipid salt with one another at said isoelectric point.

Anionic and cationic amphiphiles have respective polar head and apolar tail-groups. In accordance with the invention, the polar head and apolar tail-groups of the anionic and cationic amphiphiles and said counterions may be selected such that $\kappa_{total}$(pH) for the mixture exhibits a minimum at said isoelectric point, whereby said mixture exhibits stable lamellar phases at said second pH and, optionally, at said first pH and a fusogenic, hexagonal phase at or around said isoelectric point.

Suitably, therefore, $\kappa_{total}$(pH) (as defined above) for the amphoteric liposome according to the invention exhibits a minimum at said isoelectric point.

It has been found therefore that the combination of the following assumptions allows a proper description of lipid phase behaviour:
1) shape theory as a basis for the description;
2) for polar head-groups in the charged state, counterions become part of the head-group volume; and
3) lipid-lipid salt formation occurs in the membrane The method of the present invention therefore facilitates the identification of fusogenic amphoteric liposomes, the description of their fusion behaviour with respect to the relationship between lipid composition and fusion pH and the impact of counterions on the stability and fusion behaviour of amphoteric liposomes.

The amphoteric liposomes of the present invention comprise a lipid pair that is capable of forming a lipid-lipid salt within a bilayer. In some embodiments the capacity of the lipid pair to form a lipid-lipid salt may render the liposome bistable. Alternatively, the liposome may be stable only at said second pH and fusogenic at or around said isoelectric point.

In some embodiments, said amphoteric liposome of the invention may comprise a lipid mixture comprising a chargeable anionic amphiphile and a chargeable cationic amphiphile that are adapted to form a lipid salt with one another, wherein $\kappa_{salt}<0.34$.

Said anionic amphiphile may be selected from Chems, DMGS, DMGM, DMGG, DMGA, DMAS, DMAM, DMAG, DMAA, DOGS, DOGM, DOGG, DOGA, DOAS, DOAM, DOAG, DOAA, DMS, DMM, DMG, DMA, DOS, DOM, DOG, DOA, Chol-C3, Chol-C5 and Chol-C6. Said cationic amphiphile may be cholesterol-based or based on diacylglycerols, and may be selected from MoChol, Chim, H is Chol and Desh4.

Alternatively, said amphoteric liposome may comprise a chargeable anionic amphiphile and a chargeable cationic amphiphile that are adapted to form a lipid salt with one another, wherein $\kappa_{salt}<0.45$; and wherein said chargeable cationic amphiphile is selected from DmC4Mo2, DmC3Mo2, C4Mo4, C3Mo3, C3Mo2, C5Mo2, C6Mo2 and C8Mo2;and said chargeable anionic amphiphile is selected from Chems, DMGS, DMGM, DMGG, DMGA, DMAS, DMAM, DMAG, DMAA, DOGS, DOGM, DOGG, DOGA, DOAS, DOAM, DOAG, DOAA, DMS, DMM, DMG, DMA, DOS, DOM, DOG, DOA, Chol-C3,Chol-C5 and Chol-C6.

In yet another alternative, said amphoteric liposome may comprise a chargeable anionic amphiphile and a stable cationic amphiphile that are adapted to form a lipid salt with one another, said chargeable anionic amphiphile being in excess; wherein $\kappa_{salt}<0.34$ and the difference between $\kappa_{total}$(pH 8) for C/A=0.5 and $\kappa_{salt}>0.08$.

In such case, said chargeable anionic amphiphile may be selected from Chems, DMGS, DMGM, DMGG, DMGA, DMAS, DMAM, DMAG, DMAA, DOGS, DOGM, DOGG, DOGA, DOAS, DOAM, DOAG, DOAA, DMS, DMM, DMG, DMA, DOS, DOM, DOG, DOA, Chol-C3, Chol-C5 or Chol-C6 and fatty acids.

In yet another alternative, said amphoteric liposome may comprise a chargeable anionic amphiphile and a stable cationic amphiphile that are adapted to form a lipid salt with one another, said lipid mixture comprising an excess of said chargeable anionic amphiphile and κsalt being <0.34; wherein said stable cationic amphiphile is selected from DDAB, DC-Chol, DAC-Chol, TC-Chol, DODAP, N-methyl-PipChol, DOTAP, DOEPC and CTAB, and said chargeable anionic lipid is selected from DMGS, DMGM, DMGG, DMGA, DMAS, DMAM, DMAG, DMAA, DOGS, DOGM, DOGG, DOGA, DOAS, DOAM, DOAG, DOAA, DMS, DMM, DMG, DMA, DOS, DOM, DOG, DOA, Chol-C3, Chol-C5 and Chol-C6.

In still yet another alternative, said amphoteric liposome may comprise a lipid mixture comprising an excess of a chargeable cationic amphiphile and a stable anionic amphiphile, wherein said cationic lipid is selected from MoChol, Chim, HisChol or Desh4, DmC4Mo2, DmC3Mo2, C4Mo4, C3Mo3, C3Mo2, C5Mo2, C6Mo2 and C8Mo2, DOIM and DPIM.

Suitably, said amphoteric liposome may comprise one or more neutral or zwitterionic amphiphiles. In some embodiments, said neutral amphiphile may be cholesterol. The cholesterol can be present in the amphoteric liposomes as essentially the only neutral lipid, and can comprise more than 80 mol % of the total neutral lipids present in the liposomes. In other embodiments, cholesterol is the only neutral lipid present in the amphoteric liposomes of the invention. Alternatively, said neutral or zwitterionic lipid may be selected from phosphatidylcholines, sphingomyelins, ceramides, phosphatidylethanolamines, cholesterol and mixtures thereof.

In some embodiments, said neutral or zwitterionic lipids may be phosphatidylcholines, sphingomyelins or ceramides and may be present in the lipid mix in an amount of less than 40 mol %.

Alternatively, said neutral or zwitterionic lipids may be DOPE or cholesterol or a mixture thereof and maybe present in the lipid mix in an amount of less than 65 mol %.

In a further alternative, said neutral or zwitterionic lipids may comprise a mix of phosphatidylcholines (PC), sphingomyelins or ceramides and phosphatidylethanolamines (PE) or a mix of phosphatidylcholines (PC), sphingomyelins or ceramides and cholesterol (Chol); wherein said mix of neutral lipids is present in the lipid mix in an amount of not more than 80 mol %.

In another aspect of the invention the liposome may comprise a lipid salt other than those of the following specific combinations of amphiphiles DODAC/CHEMS; DDAB/CHEMS; DOTAP/DOGS; DOTAP/DMGS; DOTAP/DPGS; DOTAP/CHEMS; CHIM/CHEMS; CHIM/DMGS; CHIM/DOGS; HisChol/CHEMS; HisChol/DMGS; HisChol/DPGS; HisChol/DOGS; HisChol/DPPS; MoChol/CHEMS; MoChol/DMGS; MoChol/DPGS; MoChol/DOGS; MoChol/Cetyl-P; MoChol/DMPS; MoChol/DPPS; DC-CHOL/DOPA; DOTAP+CHIM/CHEMS; DC-Chol/Chems; DOIM/DMGS; DOIM/DOGS; DOTAP/oleic acid.

There are a number of amphoteric lipid combinations that show little or no fusion and might not form a lipid salt. Such lipid combinations are:
MoCHOL/POPG; MoCHOL/DPPG; HisCHOL/POPG; HisChol/DPPG.

In another aspect of the invention, the liposome may comprise a lipid mixture other than one having one of the following specific combinations of amphiphiles:

| Cationic amphiphile | Anionic amphiphile | Other | Ratio (mol. %) |
|---|---|---|---|
| DOTAP | Chems | | 30:40 |
| DOTAP | Chems | POPC | 10:40:50 |
| DOTAP | Chems | POPC | 25:25:50 |
| DOTAP | Chems | POPC | 20:30:50 |
| DOTAP | Chems | POPC | 20:20:60 |
| DOTAP | Chems | POPC | 10:30:60 |
| DOTAP | Chems | POPC | 15:25:60 |
| DOTAP | Chems | POPC:N- | 10:30:50:10 |

-continued

| Cationic amphiphile | Anionic amphiphile | Other | Ratio (mol. %) |
|---|---|---|---|
| | | glutaryl-DPPE | |
| DOTAP | Chems | DPPC:Chol | 10:30:50:10 |
| DOTAP | Chems | DPPC | 10:30:60 |
| DOTAP | Chems | DPPC | 15:35:50 |
| DOTAP | Chems | POPC:Chol | 10:20:30:40 |
| DOTAP | Chems | DMPC:Chol | 10:30:20:40 |
| DOTAP | Chems | POPC | 15:45:40 |
| DOTAP | Chems | POPC | 20:60:20 |
| DOTAP | Chems | | 25:75 |
| DOTAP | Chems | POPC | 40:40:20 |
| DOTAP | Chems | POPC | 30:50:20 |
| DOTAP | Chems | POPC | 10:70:20 |
| DOTAP | Chems | POPC | 28:47:25 |
| DOTAP | Chems | DOPE | 40:40:20 |
| DOTAP | Chems | DOPE | 30:50:20 |
| DOTAP | Chems | DOPE | 20:60:20 |
| DOTAP | Chems | DOPE | 10:70:20 |

In yet another aspect of the invention, the liposome may comprise a lipid mixture other than one having one of the following specific combinations of amphiphiles

| Cationic amphiphile | Anionic amphiphile | Other | Ratio (mol. %) |
|---|---|---|---|
| CHIM | Chems | DPPC | 15:35:50 |
| CHIM | Chems | POPC | 15:35:50 |
| DC-Chol | DOPA | | 66:34 |
| DC-Chol | DOPA | Chol | 40:20:40 |
| DC-Chol | DOPA | DMPC | 27:13:60 |
| DC-Chol | DOPA | DMPC:Chol | 27:13:20:40 |
| DC-Chol | DOPA | DMPC:Chol | 20:10:30:40 |
| DC-Chol | DOPA | DMPC:Chol | 13:7:40:40 |
| HisChol | DG-Succ | DMPC:Chol | 10:10:40:40 |
| MoChol | DG-Succ | DMPC:Chol | 10:15:35:40 |
| MoChol | DG-Succ | DMPC:Chol | 10:10:40:40 |
| MoChol | DG-Succ | DMPC:Chol | 10:30:20:40 |
| MoChol | DG-Succ | DPPC:Chol | 10:30:20:40 |
| MoChol | DG-Succ | POPC:Chol | 10:15:35:40 |
| MoChol | DG-Succ | POPC:Chol | 10:30:20:40 |
| MoChol | DG-Succ | POPC:Chol | 20:10:30:40 |

In yet another aspect of the invention, the liposome may comprise a lipid mixture other than one having one of the following specific combinations of amphiphiles:

| Cationic amphiphile | Anionic amphiphile | Other | Ratio (mol. %) |
|---|---|---|---|
| CHIM | DMG-Succ | POPC:DOPE | 17:33:12.5:37.5 |
| CHIM | DMG-Succ | POPC:DOPE | 33:17:12.5:37.5 |
| CHIM | DMG-Succ | POPC:DOPE | 23:47:7.5:22.5 |
| CHIM | DMG-Succ | POPC:DOPE | 47:23:7.5:22.5 |
| CHIM | Chems | POPC:DOPE | 17:33:12.5:37.5 |
| CHIM | Chems | POPC:DOPE | 33:17:12.5:37.5 |
| CHIM | Chems | POPC:DOPE | 23:47:7.5:22.5 |
| CHIM | Chems | POPC:DOPE | 47:23:7.5:22.5 |
| MoChol | Cetyl-P | POPC:DOPE | 20:10:10:60 |
| MoChol | Cetyl-P | POPC:Chol | 20:10:35:35 |
| MoChol | DOG-Succ | POPC:DOPE | 17:33:12.5:37.5 |
| MoChol | DOG-Succ | POPC:DOPE | 33:17:12.5:37.5 |
| MoChol | DOG-Succ | POPC:DOPE | 23:47:7.5:22.5 |
| MoChol | DOG-Succ | POPC:DOPE | 47:23:7.5:22.5 |

According to yet another aspect of the present invention there is provided a method of loading amphoteric liposomes according to the present invention with a negatively charged cargo moiety, said method comprising generating said liposomes in the presence of said negatively charged cargo moiety at said first pH using a first solvent comprising anionic counterions, and thereafter exposing said liposome to said second pH using a second solvent comprising cationic counterions.

Preferably such liposomes are bistable, exhibiting a stable lamellar phase at said first pH as well as at said second pH.

Suitably, said solvent changes are performed by the one-step admixture of the respective second solvent, such that said liposome is rapidly brought to the desired pH. Said first pH may be about pH 2-5, preferably pH 2-4. Said second pH may be about pH 7.4. In order to stabilise the liposome at said first pH, said counter-anions may preferably have a molecular volume of at least 50 Å$^3$. Thus, said counter-anions may be selected from citrate, pyrophosphate, barbituric acid and methyl sulphate.

In order to stabilise the liposome at said second pH, said counter-cations may preferably have a molecular volume of at least 50 Å$^3$.

In accordance with another aspect of the present invention, the liposome may encapsulate at least one active agent. In some embodiments, said active agent may comprise a nucleic acid. In particular, said active agent may comprise an oligonucleotide.

Without being limited to such use, the amphoteric liposomes according to the present invention are well suited for use as a carrier for nucleic acid-based drugs such, for example, as oligonucleotides and DNA plasmids. These drugs are classified into nucleic acids that encode one or more specific sequences for proteins, polypeptides or RNAs and into oligonucleotides that can specifically regulate protein expression levels or affect the protein structure through inter alia interference with splicing and artificial truncation.

In some embodiments of the present invention, therefore, the nucleic acid-based therapeutic may comprise a nucleic acid that is capable of being transcribed in a vertebrate cell into one or more RNAs, which RNAs may be mRNAs, shRNAs, miRNAs or ribozymes, wherein such mRNAs code for one or more proteins or polypeptides. Such nucleic acid therapeutics may be circular DNA plasmids, linear DNA constructs, like MIDGE vectors (Minimalistic Immunogenically Defined Gene Expression) as disclosed in WO 98/21322 or DE 19753182, or mRNAs ready for translation (e.g., EP 1392341).

In another embodiment of the invention, oligonucleotides may be used that can target existing intracellular nucleic acids or proteins. Said nucleic acids may code for a specific gene, such that said oligonucleotide is adapted to attenuate or modulate transcription, modify the processing of the transcript or otherwise interfere with the expression of the protein. The term "target nucleic acid" encompasses DNA encoding a specific gene, as well as all RNAs derived from such DNA, being pre-mRNA or mRNA. A specific hybridisation between the target nucleic acid and one or more oligonucleotides directed against such sequences may result in an inhibition or modulation of protein expression. To achieve such specific targeting, the oligonucleotide should suitably comprise a continuous stretch of nucleotides that is substantially complementary to the sequence of the target nucleic acid.

Oligonucleotides fulfilling the abovementioned criteria may be built with a number of different chemistries and topologies. Oligonucleotides may be single stranded or double stranded.

Oligonucleotides are polyanionic structures having 8-60 charges. Oligonucleotides are therefore well adapted for use as negatively charged cargo in the loading method of the present invention. In most cases these structures are polymers comprising nucleotides. The present invention is not limited to a particular mechanism of action of the oligonucleotides and an understanding of the mechanism is not necessary to practice the present invention.

The mechanisms of action of oligonucleotides may vary and might comprise effects on inter alia splicing, transcription, nuclear-cytoplasmic transport and translation.

In a preferred embodiment of the invention single stranded oligonucleotides may be used, including, but not limited to, DNA-based oligonucleotides, locked nucleic acids, 2'-modified oligonucleotides and others, commonly known as antisense oligonucleotides. Backbone or base or sugar modifications may include, but are not limited to, Phosphothioate DNA (PTO), 2'O-methyl RNA (2'Ome), 2'Fluoro RNA (2'F), 2' O-methoxyethyl-RNA (2'MOE), peptide nucleic acids (PNA), N3'-P5' phosphoamidates (NP), 2'fluoroarabino nucleic acids (FANA), locked nucleic acids (LNA), Morpholine phosphoamidate (Morpholino), Cyclohexene nucleic acid (CeNA), tricyclo-DNA (tcDNA) and others. Moreover, mixed chemistries are known in the art, being constructed from more than a single nucleotide species as copolymers, block-copolymers or gapmers or in other arrangements. In addition to the aforementioned oligonucleotides, protein expression can also be inhibited using double stranded RNA molecules containing the complementary sequence motifs. Such RNA molecules are known as siRNA molecules in the art (e.g., WO 99/32619 or WO 02/055693). Other siRNAs comprise single stranded siRNAs or double stranded siRNAs having one non-continuous strand. Again, various chemistries were adapted to this class of oligonucleotides. Also, DNA/RNA hybrid systems are known in the art.

In another embodiment of the present invention, decoy oligonucleotides can be used. These double stranded DNA molecules and chemical modifications thereof do not target nucleic acids but transcription factors. This means that decoy oligonucleotides bind sequence-specific DNA-binding proteins and interfere with the transcription (e.g., Cho-Chung, et al. in Curr. Opin. Mol. Ther., 1999).

In a further embodiment of the invention, oligonucleotides that may influence transcription by hybridizing under physiological conditions to the promoter region of a gene may be used. Again various chemistries may adapt to this class of oligonucleotides.

In a still further alternative of the invention, DNAzymes may be used. DNAzymes are single-stranded oligonucleotides and chemical modifications thereof with enzymatic activity. Typical DNAzymes, known as the "10-23" model, are capable of cleaving single-stranded RNA at specific sites under physiological conditions. The 10-23 model of DNAzymes has a catalytic domain of 15 highly conserved deoxyribonucleotides, flanked by 2 substrate-recognition domains complementary to a target sequence on the RNA. Cleavage of the target mRNAs may result in their destruction and the DNAzymes recycle and cleave multiple substrates.

In yet another embodiment of the invention, ribozymes can be used. Ribozymes are single-stranded oligoribonucleotides and chemical modifications thereof with enzymatic activity. They can be operationally divided into two components, a conserved stem-loop structure forming the catalytic core and flanking sequences which are reverse complementary to sequences surrounding the target site in a given RNA transcript. Flanking sequences may confer specificity and may generally constitute 14-16 nt in total, extending on both sides of the target site selected.

In a still further embodiment of the invention, aptamers may be used to target proteins. Aptamers are macromolecules composed of nucleic acids, such as RNA or DNA, and chemical modifications thereof that bind tightly to a specific molecular target and are typically 15-60 nt long. The chain of nucleotides may form intramolecular interactions that fold the molecule into a complex three-dimensional shape. The shape of the aptamer allows it to bind tightly against the surface of its target molecule including but not limited to acidic proteins, basic proteins, membrane proteins, transcription factors and enzymes. Binding of aptamer molecules may influence the function of a target molecule.

All of the above-mentioned oligonucleotides may vary in length between as little as 10, preferably 15 and even more preferably 18, and 50, preferably 30 and more preferably 25, nucleotides. The fit between the oligonucleotide and the target sequence is preferably perfect with each base of the oligonucleotide forming a base pair with its complementary base on the target nucleic acid over a continuous stretch of the abovementioned number of oligonucleotides. The pair of sequences may contain one or more mismatches within the said continuous stretch of base pairs, although this is less preferred. In general, the type and chemical composition of such nucleic acids is of little impact for the performance of the inventive liposomes as vehicles be it in vivo or in vitro, and the skilled artisan may find other types of oligonucleotides or nucleic acids suitable for combination with the inventive liposomes.

According to yet another aspect of the present invention there is provided a pharmaceutical composition comprising an active-agent loaded amphoteric liposome according to the invention and pharmaceutically acceptable vehicle therefor.

Other features and advantages of the invention will be apparent from the following detailed description and claims.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

DETAILED DESCRIPTION OF THE INVENTION

Figure 1:
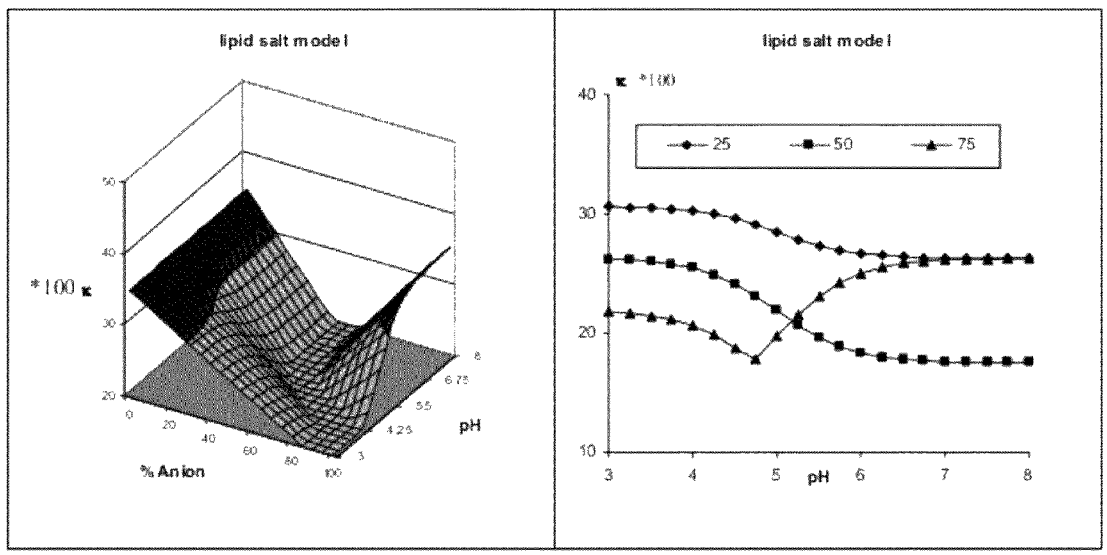
FIGS. 1 and 2 are graphical representations of the calculation of κ for different ratios between anionic and cationic model lipids. Left panel: Surface plot for κ in response to pH and percentage of anionic lipid. Right panel: Detailed analysis of the pH response for selected amounts of anionic lipids.

By "chargeable" is meant that the amphiphile has a pK in the range pH 4 to pH 8. A chargeable amphiphile may therefore be a weak acid or base. A "stable" amphiphile is a strong acid or base, having a substantially stable charge on the range pH 4 to pH 8.

By "amphoteric" herein is meant a substance, a mixture of substances or a supra-molecular complex (e.g., a liposome) comprising charged groups of both anionic and cationic character wherein:
1) at least one, and optionally both, of the cation and anionic amphiphiles is chargeable, having at least one charged group with a pK between 4 and 8,
2) the cationic charge prevails at pH 4, and
3) the anionic charge prevails at pH 8.

As a result the substance or mixture of substances has an isoelectric point of neutral net charge between pH 4 and pH 8. Amphoteric character is by this definition different from zwitterionic character, as zwitterions do not have a pK in the range mentioned above. In consequence, zwitterions are essentially neutrally charged over a range of pH values; phosphatidylcholines and phosphatidylethanolamines are neutral lipids with zwitterionic character.

By "C/A" or "C/A ratio" or "C/A molar ratio" herein is meant the molar ratio of cationic amphiphiles to anionic amphiphiles in a mixture of amphiphiles.

By "κ(min)" herein is meant the minimum of the function $\kappa_{total}(pH)$

The following abbreviations for lipids are used herein, the majority of which abbreviations are in standard use in the literature:

PC Phosphatidylcholine (unspecified membrane anchor)
PE Phosphatidylethanolamine (unspecified membrane anchor)
SM Sphingomyelin
DMPC Dimyristoylphosphatidylcholine
DPPC Dipalmitoylphosphatidylcholine
DSPC Distearoylphosphatidylcholine
POPC Palmitoyl-oleoylphosphatidylcholine
DOPC Dioleoylphosphatidylcholine
DOPE Dioleoylphosphatidylethanolamine
DMPE Dimyristoylphosphatidylethanolamine
DPPE Dipalmitoylphosphatidylethanolamine
CHEMS Cholesterolhemisuccinate
Chol-C3 Cholesterolhemimalonate
Chol-C5 Cholesterolhemiglutarate
Chol-C6 Cholesterolhemiadipate
DGS or DG-Succ Diacylglycerolhemisuccinate (unspecified membrane anchor)
DOGS or DOG-Succ Dioleoylglycerolhemisuccinate
DMGS or DMG-Succ Dimyristoylglycerolhemisuccinate
DPGS or DPG-Succ Dipalmitoylglycerolhemisuccinate
DSGS or DSG-Succ Distearoylglycerolhemisuccinate
POGS or POG-Succ Palmitoyloleoylglycerolhemisuccinate
DOGM Dioleoylglycerolhemimalonate
DOGG Dioleoylglycerolhemiglutarate
DOGA Dioleoylglycerolhemiadipate
DMGM Dimyristoylglycerolhemimalonate
DMGG Dimyristoylglycerolhemiglutarate
DMGA Dimyristoylglycerolhemiadipate
DOAS 4-{(1,2-Dioleoyl-ethyl)amino}-4-oxobutanoic acid
DOAM 4-{(1,2-Dioleoyl-ethyl)amino}-4-oxopropanoic acid
DOAG 4-{(1,2-Dioleoyl-ethyl)amino}-4-oxopentanoic acid
DOAA 4-{(1,2-Dioleoyl-ethyl)amino}-4-oxohexanoic acid
DMAS 4-{(1,2-Dimyristoyl-ethyl)amino}-4-oxobutanoic acid
DMAM 4-{(1,2-Dimyristoyl-ethyl)amino}-4-oxopropanoic acid
DMAG 4-{(1,2-Dimyristoyl-ethyl)amino}-4-oxopentanoic acid
DMAA 4-{(1,2-Dimyristoyl-ethyl)amino}-4-oxohexanoic acid
DOS 5,6-Dioleoyl-hexanoic acid
DOM 4,5-Dioleoyl-pentanoic acid
DOG 6,7-Dioleoyl-heptanoic acid
DOA 7,8-Dioleoyl-octanoic acid
DMS 5,6-Dimyristoyl-hexanoic acid
DMM 4,5-Dimyristoyl-pentanoic acid
DMG 6,7-Dimyristoyl-heptanoic acid
DMA 7,8-Dioleoyl-octanoic acid
DOPS Dioleoylphosphatidylserine
DPPS Dipalmitoylphosphatidylserine
DOPG Dioleoylphosphatidylglycerol
DPPG Dipalmitoylphosphatidylglycerol
Chol-SO4 Cholesterol sulphate
DOPA Dioleoylphosphatidic acid
SDS Sodium dodecyl sulphate
CHIM Cholesterol-(3-imidazol-1-yl propyl)carbamate DDAB Dimethyldioctadecylammonium bromide
DOTAP, DMTAP, DPTAP, DSTAP: 1,2-Diacyl-3-Trimethylammonium-Propane
DODAP, DMDAP, DPDAP, DSDAP: 1,2-Diacyl-3-Dimethylammonium-Propane
DOEPC, DMEPC, DPEPC, DSEPC: 1,2-Diacyl-sn-Glycero-3-Ethylphosphocholine
DOTMA N-[1-(2,3-dioleyloxy)propyl]-N,N,N-trimethyl ammonium chloride
DOTIM 1-[2-(oleoyloxy)ethyl]-2-oleyl-3-(2-hydroxyethyl) imidazolinium chloride
TMAG N-(a-trimethylammonioacetyl)-didodecyl-D-glutamate chloride
BCAT O-(2R-1,2-di-O-(19Z,99Z-octadecadienyl)-glycerol)-N-(bis-2-aminoethyl) carbamate
DODAC Dioleyldimethylammonium chloride
DORIE 1,2-dioleoyl-3-dimethyl-hydroxyethyl ammonium bromide
DMRIE 1,2-dimyristoyl-3-dimethyl-hydroxyethyl ammonium bromide
DOSC 1,2-dioleoyl-3-succinyl-sn-glycerol choline ester
DORI 1,2-dioleoyloxypropyl-3-dimethylhydroxyethylammonium chloride
DHMHAC N,N-di-n-hexadecyl-N, Ndihydroxyethylammoniumbromide
DHDEAB N,N-di-n-hexadecyl-N-methyl,N-(2-hydroxyethyl) ammonium chloride
DMHMAC N,N-myristyl-N-(1-hydroxyprop-2-yl)-N-methylammoniumchloride
DOTB 1,2-dioleoyl-3-(4'-trimethylammonio)butanoyl-sn-glycerol
SAINT lipids Synthetic Amphiphiles INTerdisciplinary
DPIM, DOIM 4,(2,3-bis-acyloxy-propyl)-1-methyl-1H-imidazole (unspecified membrane anchor)
DPAPy 2,3-bis-palmitoyl-propyl-pyridin-4-yl-amine
DC-Chol 3b-[N—(N9,N9-dimethylaminoethane)carbamoyl]cholesterol
TC-Chol 3b-[N—(N9,N9-trimethylaminoethane)carbamoyl]cholesterol
DAC-Chol 3b(N—(N,N'-Dimethylaminoethan)-carbamoyl)cholesterol
PipC2Chol 4{N-2-ethylamino[(3'-cholesteryl) carbamoyl]} piperazine
MoC2Chol {N-2-ethylamino[(3'-cholesteryl) carbamoyl]} morpholine
MoC3Chol {N-2-propylamino[(3'-cholesteryl) carbamoyl]} morpholine
N-methyl-PipChol N-methyl{4-N-amino[(3'-cholesteryl) carbamoyl]}piperazine
PyrroC2Chol {N-2-ethylamino[(3'-cholesteryl) carbamoyl]} pyrrolidine
PipeC2Chol {N-2-ethylamino[(3'-cholesteryl) carbamoyl]} piperidine
ImC3Chol {N-2-propylamino[(3'-cholesteryl) carbamoyl]} imidazole
PyC2Chol {N-2-ethylamino[(3'-cholesteryl) carbamoyl]} pyridine
CTAB Cetyltrimethylammonium bromide
NeoPhectin™ cationic cardiolipins (e.g. [1,3-Bis-(1,2-bis-tetradecyloxy-propyl-3-dimethylethoxyammoniumbromide)-propane-2-ol]
HistChol N-Histidinyl-Cholesterol-hemisuccinate
MoChol 4-(2-Aminoethyl)-Morpholino-Cholesterol-hemisuccinate:

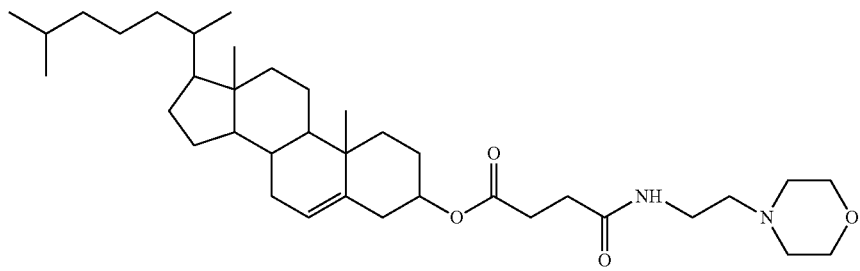 [SMILES: CC(C)CCCC(C)C1CCC2C3CC=C4CC(OC(=O)CCC(=O)NCCN5CCOCC5)CCC4(C)C3CCC12C]

HisChol Histaminyl-Cholesterolhemisuccinate:

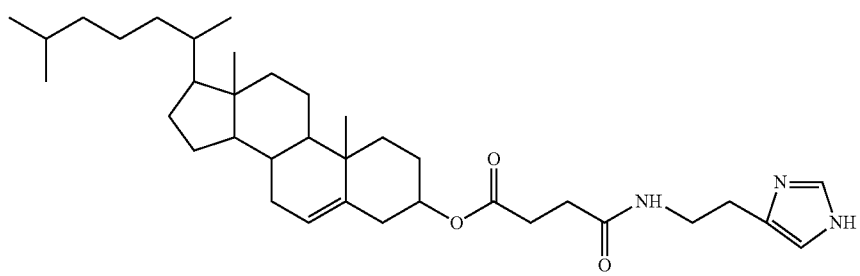 [SMILES: CC(C)CCCC(C)C1CCC2C3CC=C4CC(OC(=O)CCC(=O)NCCc5c[nH]cn5)CCC4(C)C3CCC12C]

| 17 | 18 |
|---|---|
| DmC4Mo2 4-(2-Aminoethyl)-Morpholino-Cholesterol-2,3-dimethylhemisuccinate | C4Mo4 4-(2-Aminobutyl)-Morpholino-Cholesterol-hemisuccinate |

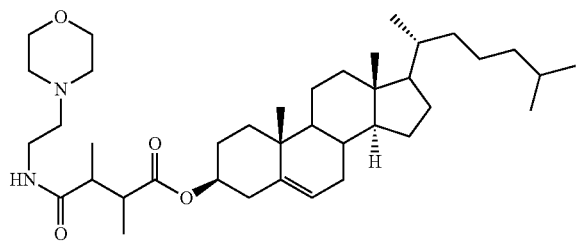 [SMILES: CC(C)CCC[C@@H](C)C1CC[C@H]2C3CC=C4C[C@@H](OC(=O)C(C)C(C)C(=O)NCCN5CCOCC5)CC[C@]4(C)C3CC[C@]12C]

DmC3Mo2 4-(2-Aminoethyl)-Morpholino-Cholesterol-2,2-dimethylhemimalonate

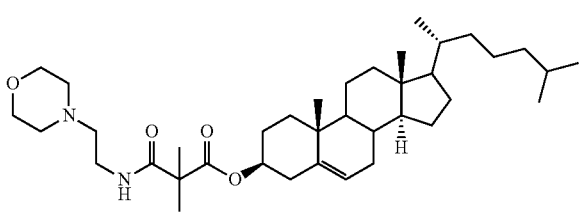 [SMILES: CC(C)CCC[C@@H](C)C1CC[C@H]2C3CC=C4C[C@@H](OC(=O)C(C)(C)C(=O)NCCN5CCOCC5)CC[C@]4(C)C3CC[C@]12C]

C5Mo2 4-(2-Aminoethyl)-Morpholino-Cholesterol-hemi-glutarate

C3Mo2 4-(2-Aminoethyl)-Morpholino-Cholesterol-hemi-malonate

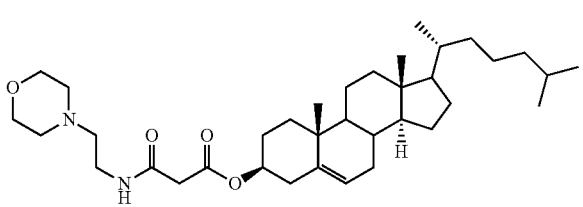 [SMILES: CC(C)CCC[C@@H](C)C1CC[C@H]2C3CC=C4C[C@@H](OC(=O)CC(=O)NCCN5CCOCC5)CC[C@]4(C)C3CC[C@]12C]

C6Mo2 4-(2-Aminoethyl)-Morpholino-Cholesterol-hemiadipate

C3Mo3 4-(2-Aminopropyl)-Morpholino-Cholesterol-hemi-malonate

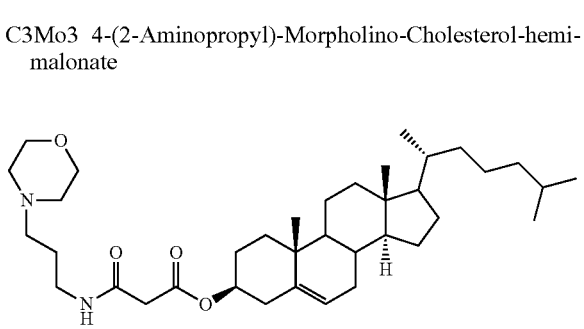

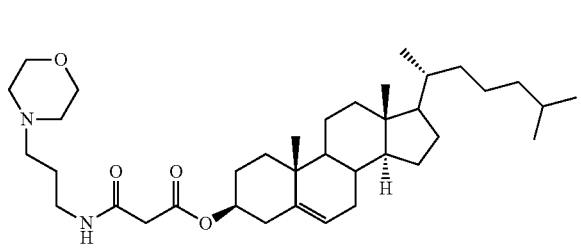 [SMILES: CC(C)CCC[C@@H](C)C1CC[C@H]2C3CC=C4C[C@@H](OC(=O)CC(=O)NCCCN5CCOCC5)CC[C@]4(C)C3CC[C@]12C]

C8Mo2 4-(2-Aminoethyl)-Morpholino-Cholesterol-hemiadipate

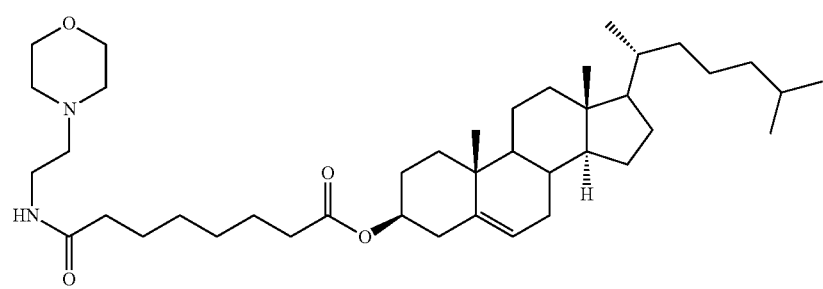 [SMILES: CC(C)CCC[C@@H](C)C1CC[C@H]2C3CC=C4C[C@@H](OC(=O)CCCCCCC(=O)NCCN5CCOCC5)CC[C@]4(C)C3CC[C@]12C]

Molecular Volumes

Lipid shape theory is built on a shape balance between the hydrophobic part and the polar head-group of a given amphiphile rather than on absolute values for the two molecular portions. In accordance with the present invention, κ is the volume ratio between the polar and apolar section of a lipid.

κ=molecular volume (head)/molecular volume (tail)

Various different ways are available to those skilled in the art to calculate molecular volumes and alternative methods and sources are discussed for example in Connolly, M. J. Am. Chem. Soc. (1985) 107, 1118-1124 and the references therein or are given at: http://www.ccl.net/cca/documents/molecular-modeling/node5.html Molecular volume is commonly calculated by assigning a value called a van der Waals radius, $r^i_{vdW}$, to each atom type in such a way that the sum of these quantities for a given atom pair, i and j, is equal to their closest possible distance (dij):

$$r^i_{vdW} + r^j_{vdW} = d_{ij}$$

Many different tables of "best" van der Waals radii exist, even though the values for corresponding atoms coming from different authors are similar. In geometric terms, the van der Waals radius may be imagined as a spherical "shield" surrounding the atom, and the closest distance between two non-bonded atoms is when their respective shields touch. However, the shields of covalently bonded atoms intersect since bond lengths are shorter than the sum of the van der Waals radii partaking atoms. A molecular van der Waals surface, also called a van der Waals envelope, is composed of the spheres for individual atoms with their intersecting sections removed.

For a single molecule (i.e., molecule for which there is a path between any two atoms along covalent bonds), the van der Waals envelope is a closed surface, and hence, it contains volume. This volume is called the molecular volume, or van der Waals volume and is usually given in $Å^3$. The straightforward way of calculating molecular volume on a computer is by numerical integration.

In some embodiments, molecular volumes for lipid molecules and the respective head and tail fragments may be calculated using DS Viewer Pro 5.0 (Accelrys Inc., San Diego, Calif.) and volumes within the respective van der Waals radii were calculated.

Typical membrane fragments are 1,2-diacyl-ethyleneglycols that represent the hydrophobic section for common phospholipids, leaving the 3' carbon atom of the original glycerol with the phosphocholine head-group. The same fragment is also found in the common cationic lipid DOTAP and its derivatives but also in diacylglycerols with other polar head-groups such as dimyristoylglycerol hemisuccinate and the like.

For the cholesterol derivatives, the entire sterol, but not the 3' oxygene, is defined as the hydrophobic section and the head-group being complementary to that.

Likewise, for cationic or anionic alkyl derivatives the polar head-group is defined as the polar fragment involving the C1 carbon of the alkyl chain. Consequently, the residual chain with n−1 carbon atoms represents the hydrophobic apolar part.

Molecular volumes depend on the constants used for the calculations and may be affected by the conformation of the molecule. Typical values obtained for the hydrophobic apolar fragments are and were used for further calculations:

TABLE 1

| Membrane fragment | Volume in $Å^3$ |
|---|---|
| di-lauroylethyleneglycol | 356 |
| di-myristoylethyleneglycol | 407 |
| di-palmitoylethyleneglycol | 458 |
| di-stearoylethyleneglycol | 509 |
| di-oleoylethyleneglycol | 501 |
| Palmitoyl-oleoylethyleneglycol | 478 |
| di-phytanoylethylenglycol | 566 |
| di-oleylethyleneglycol (e.g., in DOTMA) | 495 |
| di-palmitylethylenglycol | 452 |
| Didoceyl-D-glutamate (e.g., in TMAG) | 395 |
| Cholesteryl | 334 |
| C11 hydrophobic part in lauryl derivatives | 132 |
| C13 hydrophobic part in myristyl derivatives | 158 |
| C15 hydrophobic part in palmityl derivatives | 184 |
| C17 hydrophobic part in stearyl derivatives | 210 |
| C17 hydrophobic part in oleyl derivatives | 208 |
| Sphingomyelin/Ceramide backbone | 467 |

Molecular volumes for most counter-anions were derived the same way, but for Na+ or K+ the strongly bound hydration sphere is taken into account. The following values were used for further calculations:

TABLE 2

| Counterion | Volume in $Å^3$ | |
|---|---|---|
| Acetate⁻ | 40 | |
| Citrate⁻ | 121 | |
| Phosphate²⁻ | 49 | |
| Chloride⁻ | 21 | |
| Formiate⁻ | 29 | |
| $PF_6^-$ | 51 | |
| Methylsulfate⁻ | 64 | |
| Trifluoroacetate⁻ | 56 | |
| Barbituric acid | 79 | |
| Pyrophosphate⁴⁻ | 88 | |
| Sodium⁺ | 65[1] to 88[2] | Hydrated radii are 2, 5A and 2, 76A, respectively |
| Potassium⁺ | 24[1] to 52[2] | Hydrated radii are 1, 8A and 2, 32A, respectively |
| Lithium⁺ | 164[2] | |
| Imidazolium⁺ | 52 | |
| Morpholinium⁺ | 69 | |
| Tris(hydroxymethyl)-aminoethan⁺ | 91 | |
| Tris(hydroxyethyl)-aminoethan⁺ | 130 | |
| Bis(hydroxymethyl)-aminoethan⁺ | 74 | |
| Hydroxymethyl-aminoethan⁺ | 50 | |
| Bis(hydroxymethyl)hydroxyethyl-aminoethan⁺ | 107 | |
| Bis(hydroxyethyl)hydroxymethyl-aminoethan⁺ | 123 | |
| Triethylamine⁺ | 92 | |
| Diethyl-hydroxyethyl-amine⁺ | 100 | |
| Arginine⁺ | 135 | |
| Glucoronic acid⁻ | 129 | |
| Malonic acid⁻ | 66 | |

TABLE 2-continued

| Counterion | Volume in Å³ |
|---|---|
| Tartaric acid⁻ | 97 |
| Glucosamine⁺ | 129 |

[1] Gerald H. Pollack: Cells, Gels and the Engines of Life, Ebner and Sons Publishers, 2001
[2] Hypertext transfer protocol://www.bbc.co.uk/dna/h2g2/A1002709#footnote1

The charged polar head-groups have different representations and the molecular volumes are given below for some individual members of this group. These values were used for further calculations:

TABLE 3

| | Volume in Å³ | pK (calculated/measured) |
|---|---|---|
| Polar head-group (anions) | | |
| Hemisuccinate (e.g., in CHEMS) | 76 | |
| Hemisuccinate (e.g., in diacylglycerols) | 87 | |
| 2,3 dimethylhemisuccinate (e.g., esterified to diacylglycerols) | 117 | |
| Hemimalonate (e.g., esterified to cholesterol) | 78 | |
| Hemiadipate (e.g., esterified to diacylglycerols) | 115 | |
| Sulfate (e.g., in cholesteryl sulfate) | 50 | |
| Methylsulfate (e.g., SDS) | 64 | |
| Carboxyl (e.g., in alkyl carboxylic acids) | 42 | |
| Methylphosphate (e.g., in Cetylphosphate, phosphatidic acid) | 63 | |
| Phosphoglycerol | 115 | |
| Phosphoserin | 118 | |
| Polar head-groups (cations) | | |
| Trimethylammoniummethyl (e.g., in cetyltrimethylammonium, DOTAP and others) | 67 | |
| Dimethylammonium-dimethyl (e.g., in DODAC) | 66 | |
| Trimethyl-hydroxyethyl ammonium (e.g., in DORIE) | 88 | |
| Dimethyl-di-hydroxyethyl ammonium (e.g., in DHDEAB) | 108 | |
| N-(1-hydroxyprop-2-yl)-N-trimethyl ammonium (e.g., in DMHMAC) | 102 | |
| 4-trimethylammonio-butenoic acid methylester (e.g., in DOTB) | 128 | |
| 1-Methyl-4-choline-succinic acid diester (e.g., in DOSC) | 157 | |
| Methylimidazol (e.g., in DOIM or DPIM) | 60 | |
| 3-imidazol-1-yl-propyl carbamate (e.g., in CHIM) | 121 | |
| 2-(4-Imidazolyl)ethylamine hemisuccinate (e.g., in HisChol) | 148 | |
| N-Morpholino ethylamine hemisuccinate (e.g., in MoChol) | 166 | |
| N-Methylmorpholin | 81 | |
| Methylamine (e.g., in Stearylamine) | 30 | |
| Ethylphosphocholine (e.g., in DOEPC) | 161 | |
| 1-[2-Carboxyethyl]2-methyl-3-(2-hydroxyethyl)imidazolinium (e.g., in DOTIM) | 157 | |
| N-(a-trimethylammonioacetyl) (e.g., in TMAG) | 94 | |
| Pyridin-4-methylamine (e.g., in DPAPy) | 83 | |
| N-Methyl-pyridin (e.g., in SAINT-2) | 87 | |
| N-Methyl-4-carboxy-pyridine (e.g., in SAINT esters) | 110 | |
| N-Methyl-3,5-dicarboxy-pyridine (e.g., in SAINT diesters) | 145 | |
| Piperazine 4-N-aminoethyl carbamoyl | 130 | |
| (dimethyl)-aminoethyl carbamoyl (e.g., in DC-Chol) | 99 | |
| (trimethyl)-aminoethyl carbamoyl (e.g., in TC-Chol) | 113 | |
| N-Methyl-tris(hydroxymethyl)aminomethane | 104 | |
| N-Methyl-bis(hydroxymethyl)aminomethane | 83.5 | |
| N-Methyl-mono(hydroxymethyl)aminomethane | 61.8 | |
| Polar head-groups (neutral or zwitterionic) | | |
| Phosphocholine | 133 | |
| Phosphoethanolamine | 97 | |

It is possible to use other methods to determine molecular volumes for the lipids. Also, some parameters such as the exact split-point between membrane tail and polar head; number of water molecules in the hydration cage or the van der Waals radii can be varied without affecting the general applicability of the model. With the same understanding more subtle changes in the molecular volumes may be disregarded, in particular those arising from the dissociation of protons or from conformational changes. In some embodiments the molecular volumes recited in Tables 2 and 3 above may be used in the methods of the present invention.

The counterions fall into the same category of sizes than the actual polar head-groups. As such, it has been found that the addition or withdrawal of counterions from lipid polar regions has a substantial effect on the total head-group size and in consequence on the head/tail balance κ. As an example, the CHEMS sodium salt has a head-group size of 141 Å³ which is reduced to 76 Å³ in the undissociated form at pH 4. κ varies between 0.42 and 0.23, respectively. CHEMS does form a lamellar phase at pH 7.5 and higher but adopts a hexagonal phase at low pH.

Other lipids with known phase behaviour can be used to select κ values for discrimination between the lamellar and hexagonal phase; an example is given in Table 4 below. PE head-groups can form an intramolecular ring structure with hydrogen bonding between the terminal amino group and the oxygen in the phosphoester group (betaine structure) (e.g. Pohle et al., J. Mol. Struct., 408/409, (1997), 273-277). PC head-groups are sterically hindered and instead recruit counterions to their respective charged groups.

TABLE 4

| Lipid or mixture | κ | Phase behaviour |
|---|---|---|
| POPC | 0.46 | Lamellar |
| DOPE | 0.19 | Hexagonal | pH Induced Changes of Molecular Volumes in Amphoteric Lipid Mixtures

In a first model, in contradistinction to the present invention no lipid salt formation occurs between charged anionic and cationic lipids. This reflects the assumptions of Li and Schick (Biophys. J., 2001, 80, 1703-1711) and might be the case for lipids that are sterically hindered to form lipid salts (independent ion model).

The lipid species in the membrane comprise undissociated anions and cations as well as the dissociated anions and cations, the latter being complexed with their respective counterions. The $\kappa$ value for such a mixture is assumed to be the weighted sum of its components:

$$\kappa = \kappa(\text{anion}^0) * c(\text{anion}^0) + \kappa(\text{cation}^0) * c(\text{cation}^0) + \kappa(\text{anion}^-) * c(\text{anion}^-) + \kappa(\text{cation}^+) * c(\text{cation}^+); \quad (1)$$

wherein $\text{anion}^0$ or $\text{cation}^0$ denotes the uncharged species and $\text{anion}^-$ or $\text{cation}^+$ denotes the respective charged species; and wherein c herein denotes concentration.

The amounts of the individual species present under such assumption can be calculated from known equilibrium constants K for the acid or base dissociation:

$$c(\text{anion}^-) = c(\text{anion}^{tot})/(c_{H+}/K+1) \quad (2)$$

$$c(\text{anion}^0) = c(\text{anion}^{tot}) - c(\text{anion}^-) \quad (3)$$

$$c(\text{cation}^+) = c(\text{cation}^{tot})/(K/c_{H+}+1) \quad (4)$$

$$c(\text{cation}^0) = c(\text{cation}^{tot}) - c(\text{cation}^+); \quad (5)$$

wherein $\text{anion}^0$ is the undissociated anion, $\text{anion}^-$ the negatively charged molecule and $\text{anion}^{tot}$ the total concentration of the respective anion. Cations follow the same nomenclature and $c_{H+}$ and K describe the proton concentration and the equilibrium constant for the acid or base, respectively.

However, taking possible interaction between a cationic and anionic amphiphile into account in accordance with the invention, the lipid salt occurs as a fifth species in the mixture:

$$\kappa = \kappa(\text{anion}^0) * c(\text{anion}^0) + \kappa(\text{cation}^0) * c(\text{cation}^0) + \kappa(\text{anion}^-) * c(\text{anion}^-) + \kappa(\text{cation}^+) * c(\text{cation}^+) + \kappa(\text{salt}) * c(\text{salt}) \quad (6)$$

In a lipid salt, the cationic amphiphile serves as a counterion to the anionic amphiphile and vice versa thus displacing the small counterions like sodium or phosphate from the head-group. The lipid salt is net uncharged and its geometry has to be assumed to be the sum of both parts without the small counterions. Therefore:

$$\kappa(\text{salt}) = (v_{head}(\text{cation}) + v_{head}(\text{anion}))/(v_{apolar}(\text{cation}) + v_{apolar}(\text{anion})) \quad (7)$$

Salt formation is limited by the charged amphiphile that is present in the lowest concentration:

$$c(\text{salt}) = \text{MIN}(c(\text{cation}^+); c(\text{anion}^-)) \quad (8)$$

Salt formation between the two charged amphiphiles is assumed to be complete within this model, but of course, an incomplete salt formation may be assumed. The following calculations further reflect the fact that the salt comprises two lipid molecules. It is of course possible to assume further some membrane contraction upon lipid salt formation and to put a different weight on the contribution of k(salt).

Model Calculations

To achieve amphoteric character of a lipid mix, at least one of the lipid ions needs to be a pH-sensitive, weak acid or base ("chargeable"). A detailed disclosure is found in WO 02/066012 the contents of which are incorporated herein by reference. Being different in character, three basic systems are possible and are analysed here:

"Amphoter I" strong cation and weak anion,
"Amphoter II" weak cation and weak anion,
"Amphoter III" weak cation and strong anion.

Amphoter I Systems

Amphoter I systems need an excess of the pH-sensitive anion to achieve amphoteric character. At pH 7 to 8 the anionic lipid is fully charged and salt formation occurs until all cationic lipids are consumed. In an example with 70 mol. % anionic lipid and 30 mol. % cationic lipid, all cationic lipid and a corresponding 30 mol. % of the anionic lipid would exist as lipid salt while 40 mol. % of the anionic lipid is unbound and recruits its counterion to the head-group.

Starting from neutral conditions, a reduction of the pH discharges the anionic lipid, the $\kappa$ value becomes smaller owing to loss of the counterion and reaches a minimum when the portion of still-charged anionic lipid is equal to the amount of cationic lipid. Therefore, $\kappa$ is minimal at the isoelectric point of the amphoteric lipid mixture. If the pH is further lowered, an increasingly smaller portion of the anionic lipid remains charged. This means dissociation of the lipid salt and recruitment of counterions, now to the cationic lipid liberated from the lipid salt.

The left panel in FIG. 1 of the accompanying drawings illustrates the complex behaviour of $\kappa$ in dependence from pH and the amount of anionic lipid in the mixture. A "valley of fusogenicity" appears, and any amphoteric mixture having more than 55 mol. % and less than 85 mol. % anionic lipid is expected to fuse under slightly acidic conditions but to be stable both at neutrality and under more acidic conditions.

Amphoter I mixtures with less than 50 mol. % anionic lipid are no longer amphoteric since the anion can modulate, but not overcompensate, the charge on the cationic lipid. These mixtures might undergo a pH-dependent fusion, but do not provide a second stable phase at low pH. A 1:1 complex adopts a lamellar phase only at low pH and undergoes fusion at neutrality.

The parameters used for the calculations illustrated in FIG. 1 are given in Table 5 below; volumes in Å$^3$.

TABLE 5

| | |
|---|---|
| Anion head volume | 70 |
| Anion tail volume | 400 |
| Anion pK | 5 |
| Cation head volume | 70 |
| Cation tail volume | 400 |
| Cation pK | 15 |
| Counterion+ | 70 |
| Counterion− | 70 |

Amphoter II Systems

Figure 2:
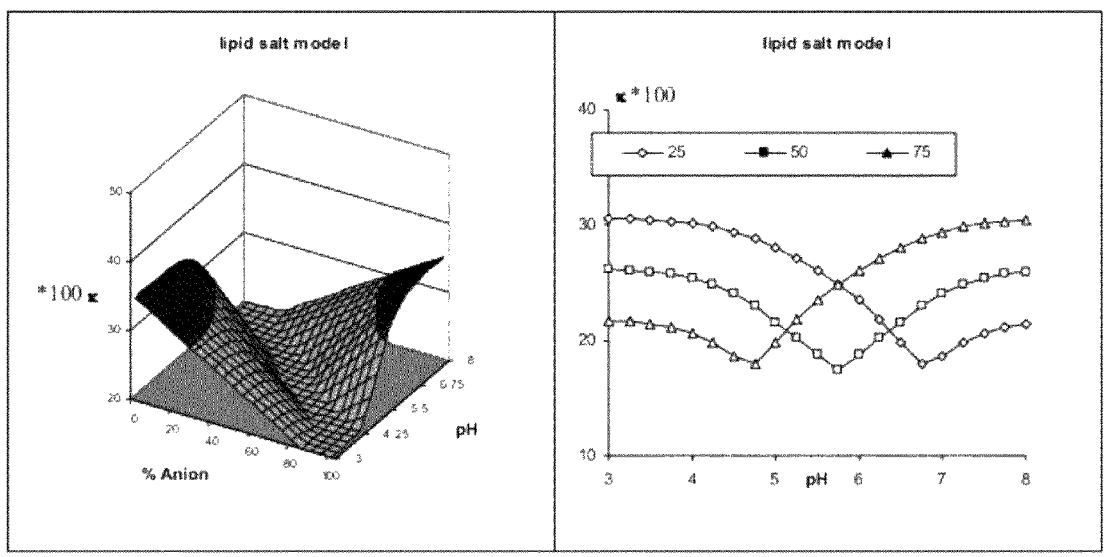

Amphoter II systems have the distinct advantage to be amphoteric over the entire range of anion:cation ratios and no charge overcompensation for the strong ion is needed as in Amphoter I or Amphoter III systems. A calculation for a model system is shown in FIG. 2.

The parameters used for the calculation are given in Table 6 below; all volumes in Å$^3$.

TABLE 6

| | |
|---|---|
| Anion head volume | 70 |
| Anion tail volume | 400 |
| Anion pK | 5 |
| Cation head volume | 70 |
| Cation tail volume | 400 |
| Cation pK | 6.5 |

TABLE 6-continued

| | |
|---|---|
| Counterion+ volume | 70 |
| Counterion− volume | 70 |

Again, the lipid salt model predicts stable states at neutral to slightly alkaline pH but also at slightly acidic pH and a pronounced valley of instability or fusogenicity in between.

In contrast to amphoter I systems, fusogenic states can be reached across a wide range of different lipid ratios between the anionic and cationic components. That is, the valley of fusogenicity extends across a wider range of anion/cation ratios, allowing a greater degree of control over the pH at which a given system is fusogenic.

Amphoter III Mixtures

Figure 3:
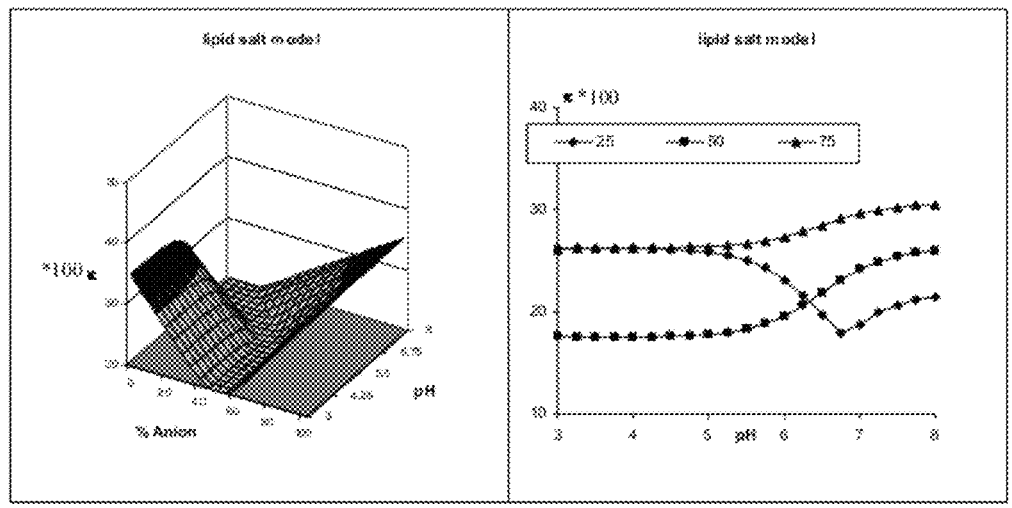
FIG. 3 is a graphical representation of the calculation of κ for different ratios between anionic and cationic model lipids in amphoter III systems. Left panel: Surface plot for κ in response to pH and percentage of anionic lipid. Right panel: Detailed analysis of the pH response for selected amounts of anionic lipids.

Amphoter III mixtures comprising a stable anion and a pH-sensitive cation cannot form lipid salts at neutral pH, since little to no charged cationic lipid exists at this pH. It needs ongoing acidification to first create the cation which then may undergo salt formation. Calculation for a model system is shown in FIG. 3.

The parameters used for the calculation are given in Table 7 below; all volumes in $Å^3$.

TABLE 7

| | |
|---|---|
| Anion head volume | 70 |
| Anion tail volume | 400 |
| Anion pK | 1 |
| Cation head volume | 70 |
| Cation tail volume | 400 |
| Cation pK | 6.5 |
| Counterion+ volume | 70 |
| Counterion− volume | 70 |

As can be seen from FIGS. 1 and 3, amphoter III systems behave like the mirror image of amphoter I systems. They provide a valley of fusogenicity as long as the weak lipid ion is present in excess and over-compensates the constant charge on the opposite ion. In contrast to amphoter I systems the pH for fusion locates higher than the pK of the pH-sensitive lipid ion.

Figure 4:
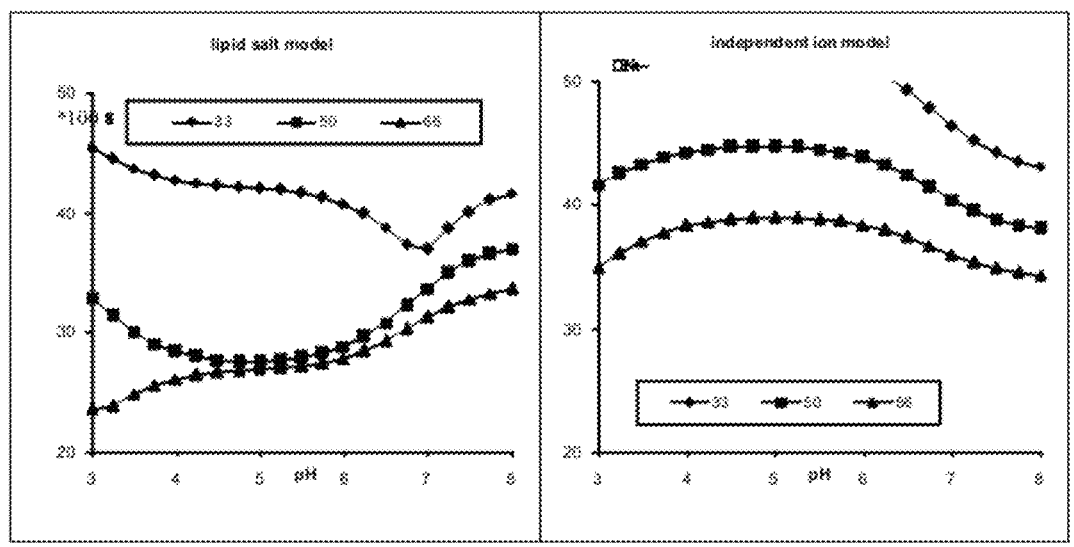
FIG. 4: is a graphical representation of the calculation of κ for different ratios between anionic and cationic model lipids in amphoter III systems. Left panel: Salt bridge model; Right panel: independent ion model.

Experimental evidence for the fusion valley is given in the Examples 1 to 4 and provides confirmation for the central hypothesis of lipid salt formation in amphoteric liposomes. The examples also provide two closely related amphoter III systems (MoChol/POPG and MoChol/DOPA) where fusion is only observed in one of the two, namely MoChol/DOPA. This may be due to steric hindrance, as the protonated tertiary nitrogen in MoChol is situated at the lower end of the morpholino ring and is therefore not easily accessible. In addition, the phosphate in POPG sits right at the lipid/water interface and is protected with a glycerol towards the water phase. In contrast, the phosphate group in DOPA is easily accessible. The model described above can be used to describe both situations, if lipid salt formation is optionally removed from the model building assumptions (equations (1) to (5) above only). A comparison between the two scenarios is shown in FIG. 4. The parameters used for the calculation of FIG. 4 are given in Table 8 below, DOPA and MoChol in $Na/H_2PO_4$ were used as model compounds; and volumes are expressed as $Å^3$.

TABLE 8

| | |
|---|---|
| Anion head volume | 63 |
| Anion tail volume | 501 |
| Anion pK | 3 |
| Cation head volume | 166 |
| Cation tail volume | 334 |
| Cation pK | 6.5 |
| Counterion+ volume | 65 |
| Counterion− volume | 49 |

Whereas the lipid salt model predicts fusion with lower pH, a deletion of salt formation leads to a system where an increase of κ is observed when the cationic lipid becomes protonated. If at all, such situation leads to an even more lamellar and eventually to a micellar state of the membrane. However, the limit for micelle formation has not been determined within the context of this model.

The monoanionic state of DOPA (pKa 1=3, pKa 2=8) was used for the model since DOPA exists as a mono-anion when MoChol becomes ionised (pKa=6.5). The model predicts little or no fusogenicity at 33 mol. % anion, valley type fusion behaviour at 50 mol. % anion and monophasic fusion behaviour at 66 mol. % and more of the anion. The entire complexity of the model is reflected in the practical behaviour of the membrane as illustrated in Example 4 below.

The algorithm according to the present invention allows prediction of fusion behaviour of a wide range of amphoteric lipid mixtures. The prediction rules are derived from a simple geometrical description of the interacting lipids and are independent from the actual chemical representation of the molecules. As such, existing and novel lipid combinations can be easily tested by those skilled in the art, and the intended fusion behaviour can be predicted in a rational way. The following key parameters may illustrate such selection process, but other priorities might be set dependent on the respective goals of the application.

1. κ of the Lipid Salt

κ of the lipid salt is calculated in equation (7) above and may suitably be lower than 0.34 or 0.35 to predict reasonably a fusogenic hexagonal phase. In some embodiments κ may be lower than 0.3; preferably lower than 0.25. κ(salt) is low when the combined polar head-groups are small and the combined hydrophobic portions are large. The preferred sum of head-group volumes is about 300 $Å^3$ or smaller; in a more preferred embodiment this volume is smaller than 220 $Å^3$, and an even more preferred value is smaller than 170 $Å^3$. According to the selection made above, preferred sums for the tail group volumes are larger than 650 $Å^3$ and may be as large as about 1000 $Å^3$, wherein combinations of proper head and tail groups are governed by the preferred k(salt) values.

2. Amplitude of Change (d(κ)/d(pH))

Figure 5:
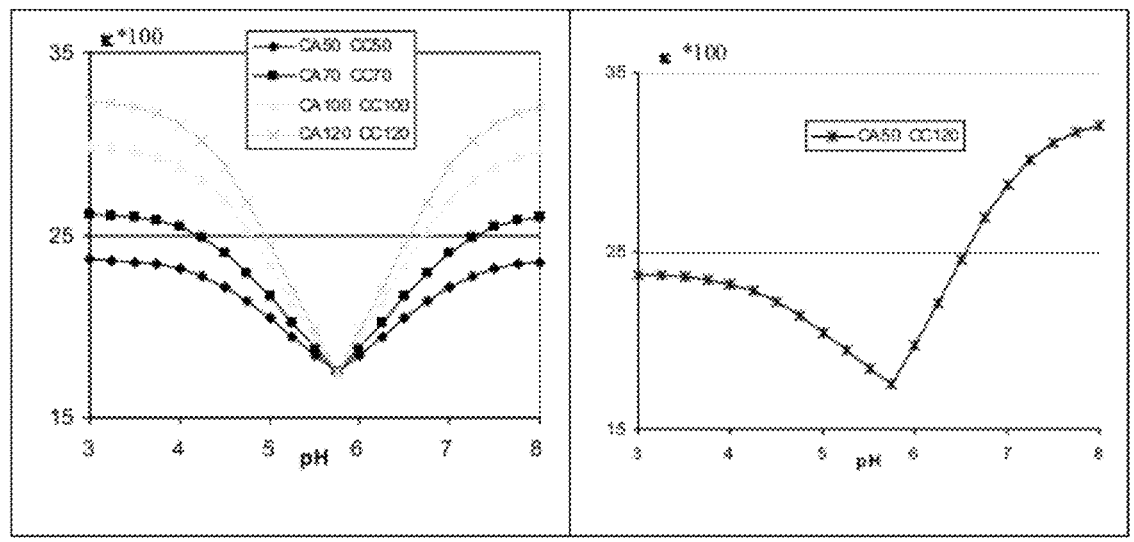
FIG. 5 shows the stabilisation of the anionic or cationic state of an amphoter II mixture through various counterion sizes. Left panel: Analysis for equal counterion sizes. Right panel: exclusive stabilisation of the anionic state through larger cationic counterions. CA—counter-anion; CC—counter-cation; the numbers in the legend indicate molecular volumes in $Å^3$

In a preferred embodiment of the present invention, a lipid salt with a low value for κ is stabilised below or above its isoelectric point by recruitment of counterions. In a preferred embodiment of the invention larger counterions are used to stabilise either the cationic or the anionic state of the amphoteric lipid mixture. FIG. 5 illustrates such dependence from counterions size for an amphoter II system. The parameters used for the calculation of FIG. 5 are given in Table 9 below.

TABLE 9

| | |
|---|---|
| Anion head volume | 70 |
| Anion tail volume | 400 |
| Anion pK | 5 |
| Cation head volume | 70 |
| Cation tail volume | 400 |
| Cation pK | 6.5 |

TABLE 9-continued

| | |
|---|---|
| Counterion+ | See FIG. 5 |
| Counterion− | See FIG. 5 |

It becomes apparent from the right panel of FIG. 5 that such stabilisation may be asymmetric, e.g., providing rather limited stabilisation for the cationic phase and more stabilisation of the anionic phase of the amphoteric lipid mix. Also, counterions that do not naturally exist in physiological body fluid may be used to improve stability during storage; exchange of such storage ions with the sodium ions present in the body fluids may be advantageous for discharging the cargo from the liposomes in vivo. The selection of proper ion volumes for the individual or common stabilisation of a lipid phase is therefore a preferred application of the present invention. Such stabilisation is of particular use for the manufacturing and storage of amphoteric liposomes.

In some embodiments of the present invention larger counter-cations are used to stabilise the amphoteric liposomes at neutral conditions. In a preferred embodiment such counter-cations have a molecular volume of 50 Å$^3$ or more, in a more preferred embodiment this volume exceeds 75 Å$^3$ and said neutral pH is between pH 7 and pH 8, more preferred about the physiological pH of 7.4.

If amphoteric liposomes are produced for pharmaceutical purposes, compatibility of the used ions with the application route needs to be obeyed. Suitable counter-cations can be selected from Table 2 above describing the ion sizes. Preferred counter-cations for pharmaceutical compositions are sodium or the respective ionized forms of tris(hydroxymethyl)aminomethane, tris-hydroxyethylaminomethane, triethylamine, arginine, in particular L-arginine and the like.

In an embodiment of the invention the amphoteric liposomes may be manufactured at a low pH in their cationic state. Under these conditions, the liposomes can bind polyanions such as proteins, peptides or nucleic acids, whether as large plasmids or smaller oligonucleotides. Such binding is useful for improvement of the encapsulation efficacy of said materials into the amphoteric liposomes.

It is advantageous to use a lipid phase with a low κ at acidic pH. Selection of large counter-anions facilitates stabilisation of said lipid phase, e.g., for the production of such liposomes and the encapsulation of cargo under these conditions.

Suitable large counter-anions have a molecular volume larger than 50 Å$^3$, preferred large counterions have a molecular volume larger than 75 Å$^3$. Suitable counter-anions can be selected from Table 2 above. Preferred counter-anions are citrate, pyrophosphate, barbiturate, methyl sulphate and the like. After having contacted the lipid phase with the cargo to be encapsulated under acidic conditions, the liposomes are than neutralized and non-encapsulated cargo can optionally be removed. Typically, non-encapsulated cargo detaches from the lipid membrane since both carry the same charge under neutral conditions. The amphoteric liposomes are negatively charged above their isoelectric point, e.g., at a pH between 7 and 8 and the cargo molecules exist as polyanions at such a pH. This is in particular the case with nucleic acids that carry one negative charge per nucleobase. Such liposomes can undergo effective destabilisation when exposed to the low pH in combination with a smaller counter-anion. This is for example the case after systemic administration and cellular uptake and endocytosis of such liposomes. Chloride or phosphate are the most common counter-anions in the body fluids of animals, be it any animal, a mammal or humans. Phosphate, but even more so chloride, are small counterions with little or no hydration shell and molecular volumes <60 Å$^3$.

Figure 6:
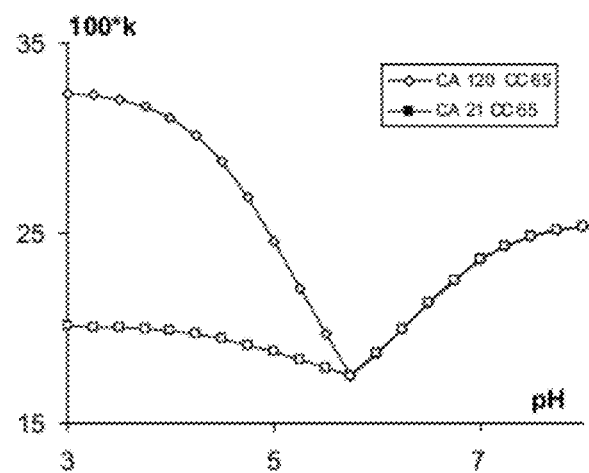
FIG. 6 illustrates the asymmetric stabilisation of a cationic amphoter II lipid phase through various counter-anions. During production, the cationic lipid phase is stabilised with larger anions (CA120). Liposomes are adjusted to a neutral pH and the buffer composition is changed for a smaller counter-anion (CA21). Liposomes that now encounter acidic pH are prone to fusion since the lipid phase has much lower values of κ. CA—counter-anion; CC—counter-cation; the numbers in the legend indicate molecular volumes in $Å^3$.

FIG. 6 illustrates a cycle of liposome generation and use which illustrates selective stabilisation and destabilisation of the lipid phase under acidic conditions through asymmetric counterion use. The parameters used for the calculation of FIG. 6 are given in Table 10 below; volumes in Å$^3$.

TABLE 10

| | |
|---|---|
| Anion head volume | 70 |
| Anion tail volume | 400 |
| Anion pK | 5 |
| Cation head volume | 70 |
| Cation tail volume | 400 |
| Cation pK | 6.5 |
| Counterion+ | See FIG. 6 |
| Counterion− | See FIG. 6 |

3. Isoelectric Point

A mathematical description for the isoelectric point of amphoteric liposomes is been given in the WO 02/066012. In accordance with the present invention, the isoelectric point of the amphoteric liposomes can be adjusted to a wide range of conditions, and there is sufficient chemical representation for individual lipids with different pK dissociation constants that allows the skilled artisan to select useful components and combinations for the making of amphoteric liposomes. In addition, the isoelectric point for a given amphoteric lipid composition can be easily tuned through the molar ratio between the anionic and the cationic lipid as presented in Hafez et al., Biophys. J., 79, (2000), 1438-1446.

4. Relationship Between κ(Lipid Salt) and Counterions

Figure 7:
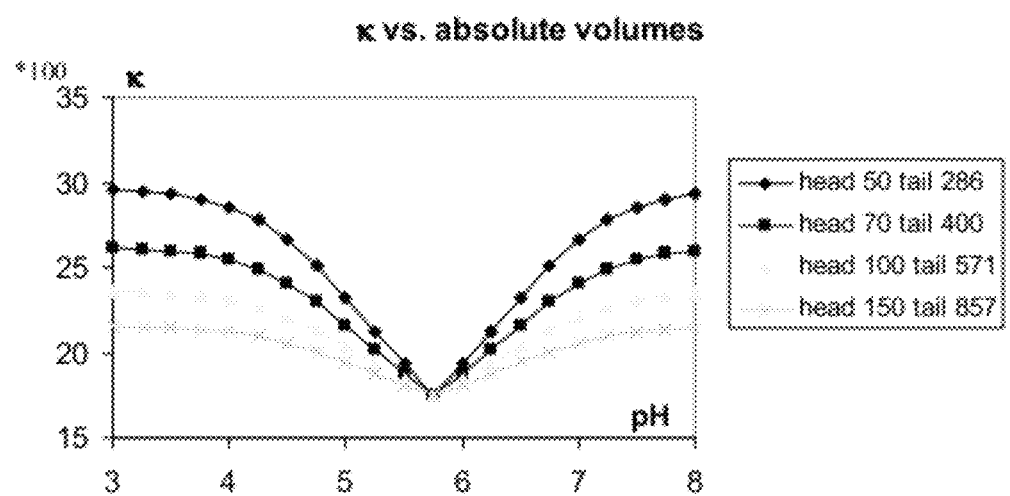
FIG. 7 illustrates the impact of absolute molecular volumes for given values of κ and counterion size. κ was adjusted to 0.175 for the cationic and anionic lipid in an amphoter II system, but the absolute lipid size was varied; the numbers in the legend indicate molecular head and tail volumes for both the cationic and anionic lipid in $Å^3$.

Preferred values for κ and counterion size have been given above. In addition to these criteria, the absolute molecular volume of a lipid molecule is of importance. For large absolute volumes the relative impact of the counterion binding becomes smaller. This is illustrated in FIG. 7 for lipids with identical κ, but different absolute volumes. Other parameters used for the calculation of FIG. 7 are given in Table 11 below; volumes in Å$^3$.

TABLE 11

| | |
|---|---|
| Anion head volume | see legend in FIG. 7 |
| Anion tail volume | see legend in FIG. 7 |
| Anion pK | 5 |
| Cation head volume | see legend in FIG. 7 |
| Cation tail volume | see legend in FIG. 7 |
| Cation pK | 6.5 |
| Counterion+ volume | 70 |
| Counterion− volume | 70 |

In a preferred embodiment of the present invention the absolute molecular volumes for the lipids are small, e.g., <1000 Å$^3$ for the combined volumes of an anionic and cationic lipid. More preferred are lipid pairs with about 700 Å$^3$ molecular volume.

Figure 8:
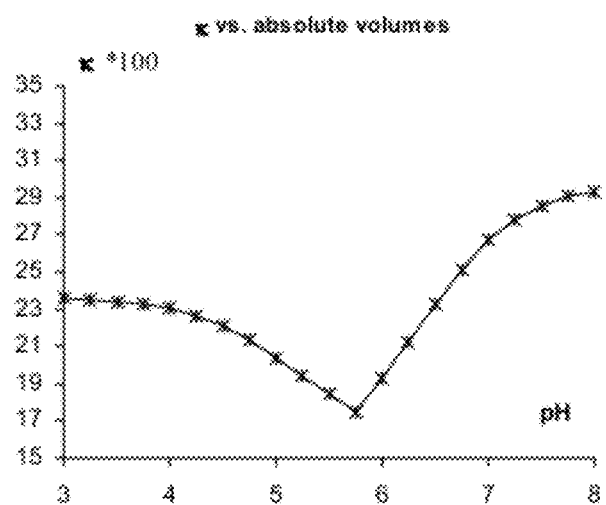
FIG. 8 illustrates the impact of absolute molecular volumes for given values of κ and counterion size. κ was adjusted to 0.175 for the cationic and anionic lipid in an amphoter II system, but the anionic lipid had a smaller molecular volume than the cationic lipid.

As was the case for counterions of different volumes, asymmetric stability of a cationic and anionic lipid phase can also be achieved by selection of lipids with different absolute molecular volumes, even if said lipids have equal κ values. The example in FIG. 8 illustrates such a design variant, where a smaller anionic lipid leads to selective destabilisation under acidic conditions. Parameters used for the calculation of FIG. 8 are given in Table 12 below; volumes in Å$^3$.

TABLE 12

| | |
|---|---|
| Anion head volume | 50 |
| Anion tail volume | 286 |
| Anion pK | 5 |
| Cation head volume | 100 |
| Cation tail volume | 571 |
| Cation pK | 6.5 |
| Counterion+ volume | 70 |
| Counterion− volume | 70 |

Figure 19A:
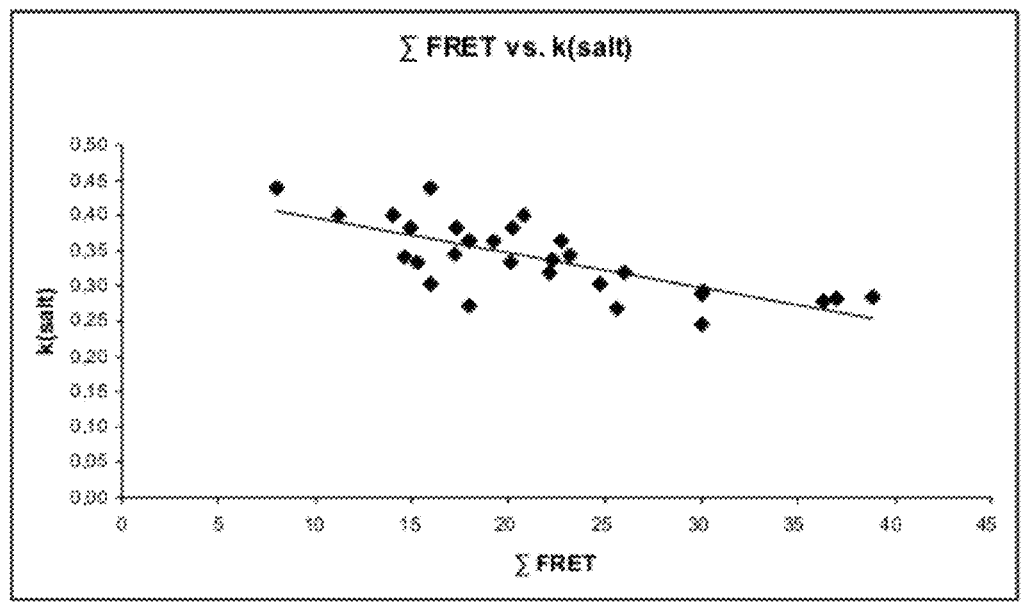
FIG. 19a shows the inverse correlation between fusion intensity (expressed as ΣFRET in the matrix C/A=0.33-3 vs. pH) and k(salt) for amphoter II systems, being formed from cholesterol based pH sensitive cationic lipids (excepting DmC4Mo2) and different pH sensitive anionic lipids.
Figure 19B:
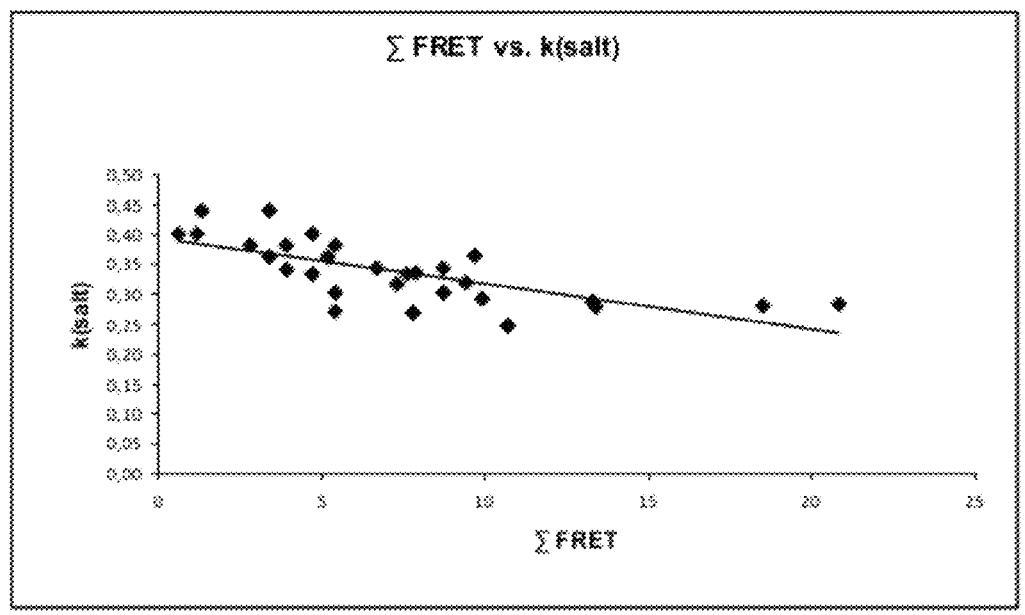
FIG. 19b shows the inverse correlation between fusion intensity (expressed as ΣFRET in the matrix C/A=0.7-1.5 vs. pH) and k(salt) for amphoter II systems, being formed from cholesterol based pH sensitive cationic lipids (excepting DmC4Mo2) and different pH sensitive anionic lipids.
Figure 19C:
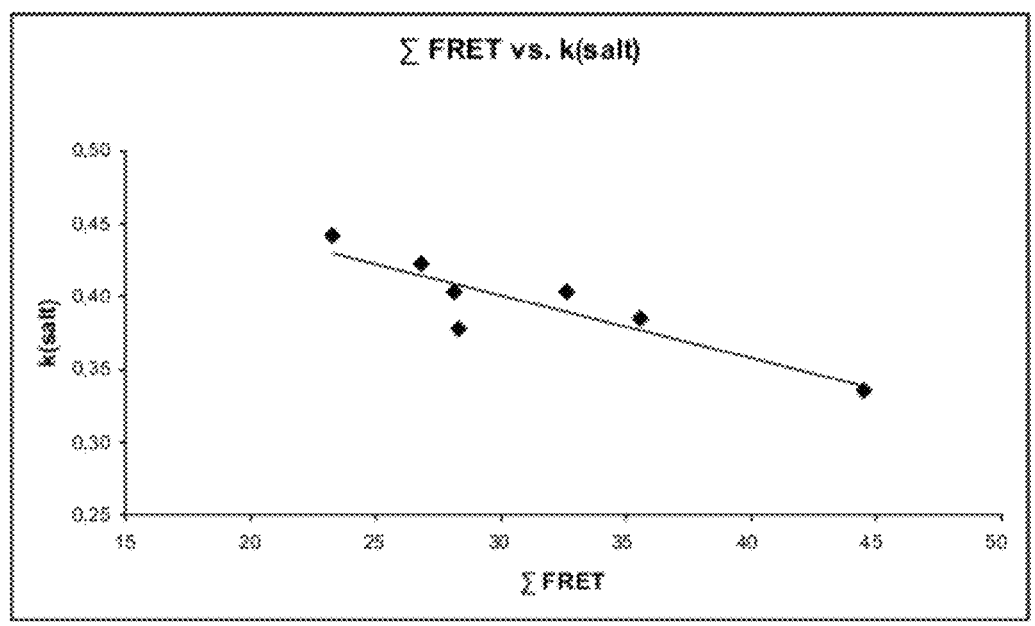
FIG. 19c illustrates the inverse correlation between fusion intensity (expressed as ΣFRET in the matrix C/A=0.33-3 vs. pH) and k(salt) for amphoter II systems comprising the cationic lipid DmC4Mo2 in combination with different anionic pH sensitive lipids.
Figure 20:
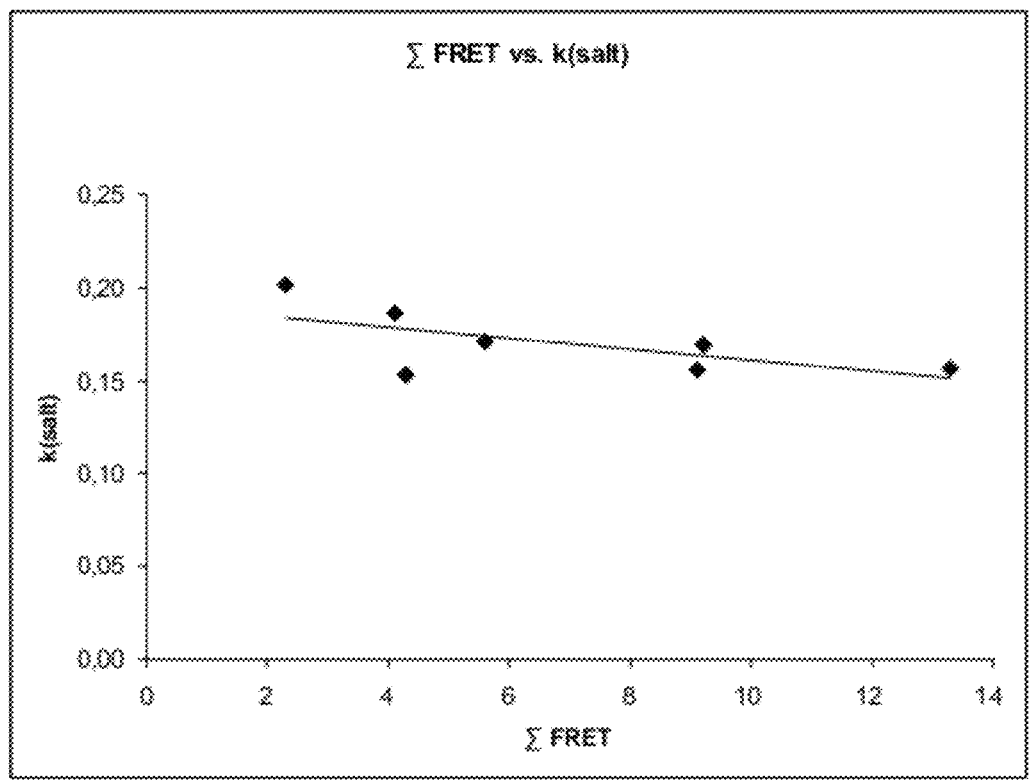
FIG. 20 shows inverse correlation between fusion intensity (expressed as ΣFRET in the matrix C/A=0.4-0.75 vs. pH) and k(salt) for amphoter I systems comprising DOTAP or DODAP and various pH sensitive anions.
Figure 21A:
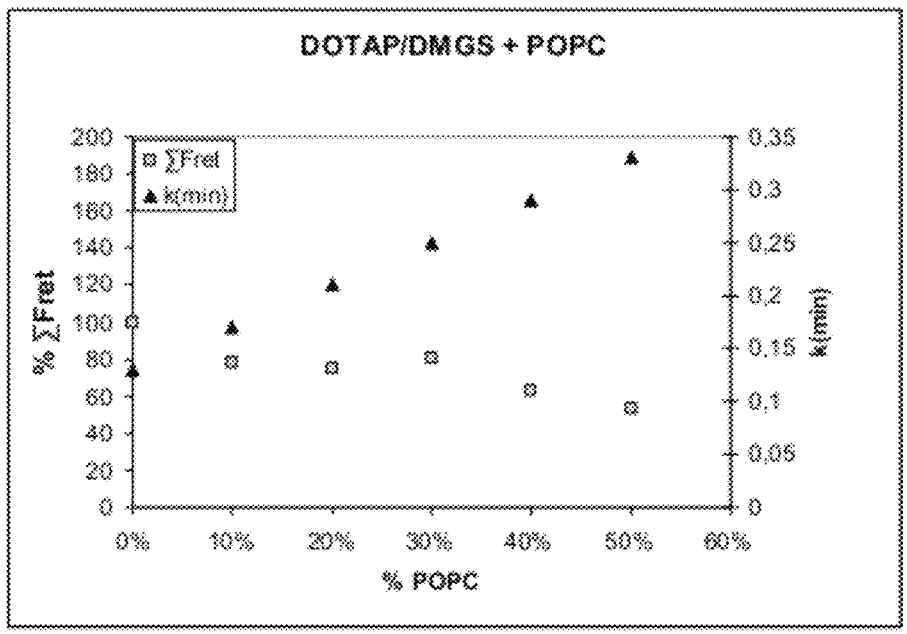
FIGS. 21a and 21b show plots of the intensity of fusion (expressed as % ΣFRET in the matrix C/A=0.17-0.75 for DOTAP/DMGS; C/A=0.33-3 for MoChol/DOGS vs. pH) for liposomes from DOTAP/DMGS or MoChol/DOGS against k(min) for mixtures with 0%-50% POPC. The reference k(min) was modelled for C/A=0.66 (DOTAP/DMGS) or C/A=1 (MoChol/DOGS). The % ΣFRET for 0% POPC is set to 100.
Figure 21B:
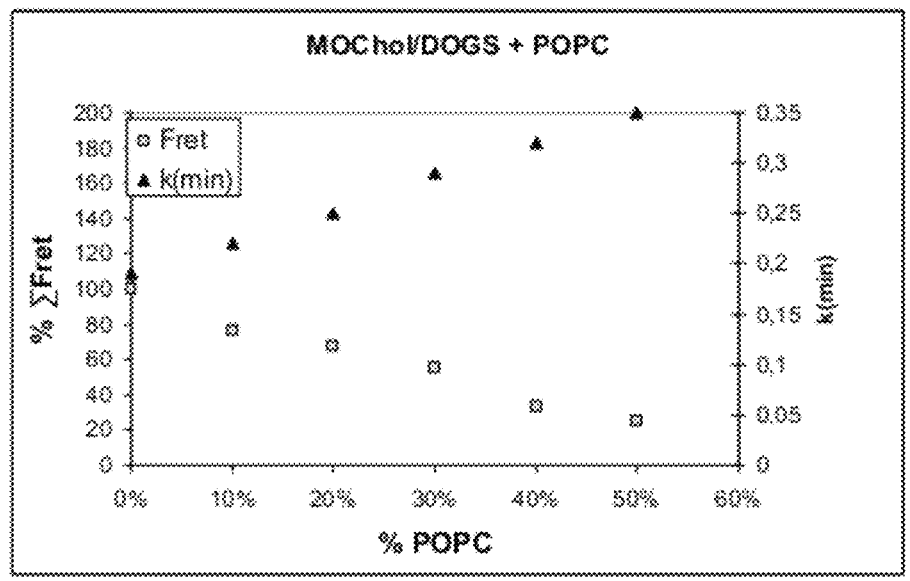
Figure 22A:
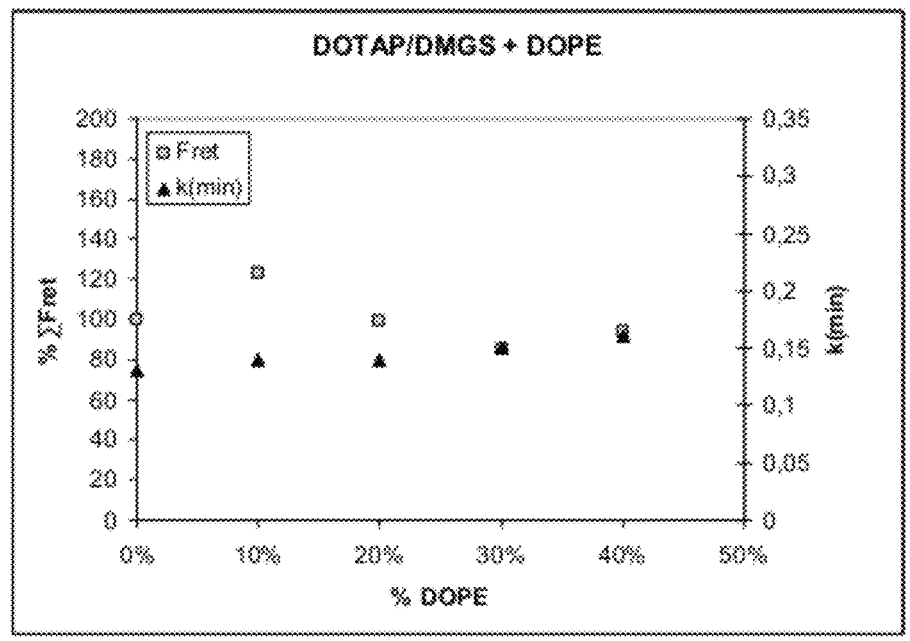
FIGS. 22a and 22b show plots of the intensity of fusion (expressed as % ΣFRET in the matrix C/A=0.17-0.75 for DOTAP/DMGS; C/A=0.33-3 for MoChol/DOGS vs. pH) for liposomes from DOTAP/DMGS or MoChol/DOGS against k(min) for mixtures with 0%-50% DOPE. The reference k(min) was modelled for C/A=0.66 (DOTAP/DMGS) or C/A=1 (MoChol/DOGS). The % ΣFRET for 0% DOPE is set to 100.
Figure 22B:
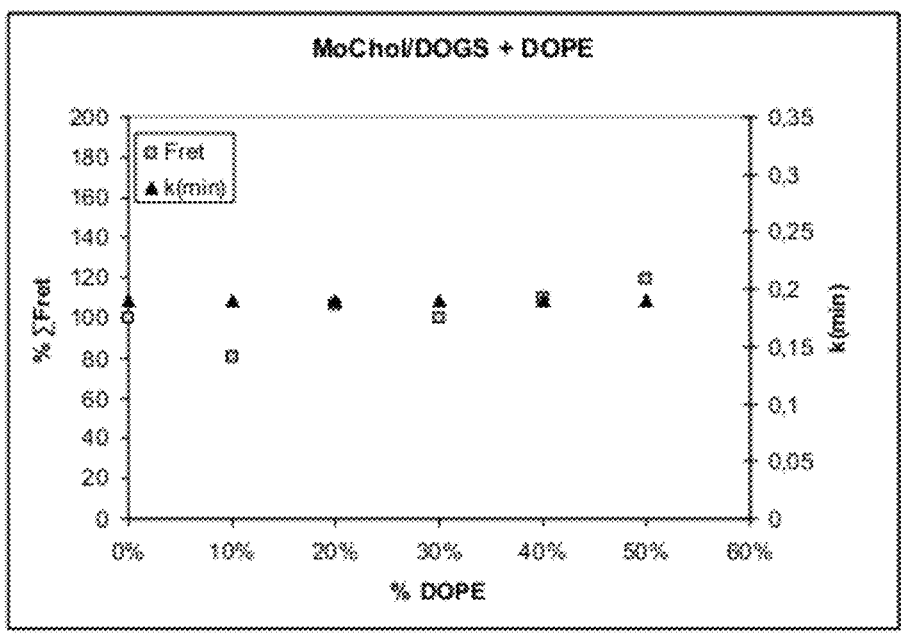
Figure 23A:
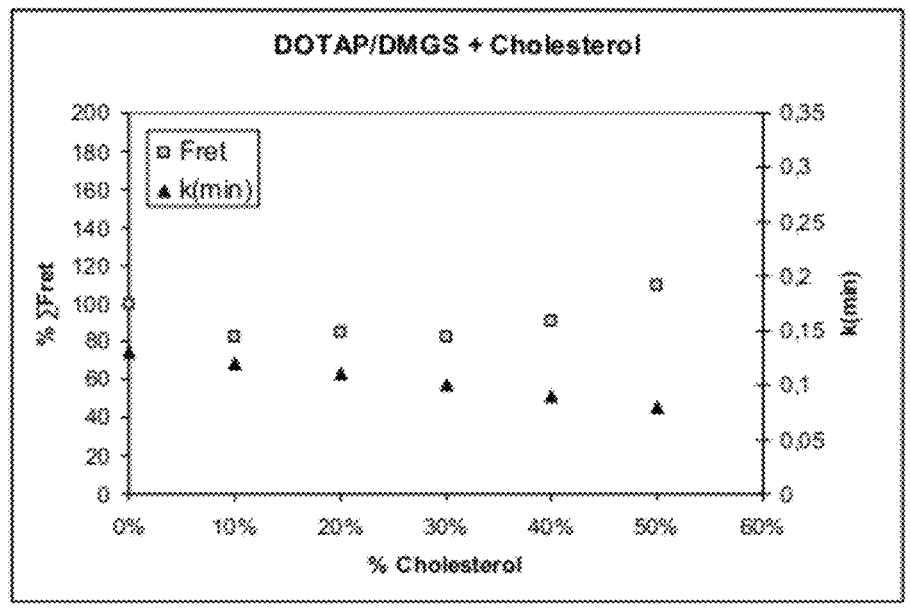
FIGS. 23a and 23b show plots of the intensity of fusion (expressed as % ΣFRET in the matrix C/A=0.17-0.75 for DOTAP/DMGS; C/A=0.33-3 for MoChol/DOGS vs. pH) for liposomes from DOTAP/DMGS or MoChol/DOGS against k(min) for mixtures with 0%-50% cholesterol. The reference k(min) was modelled for C/A=0.66(DOTAP/DMGS) or C/A=1 (MoChol/DOGS). The % ΣFRET for 0% cholesterol is set to 100.
Figure 23B:
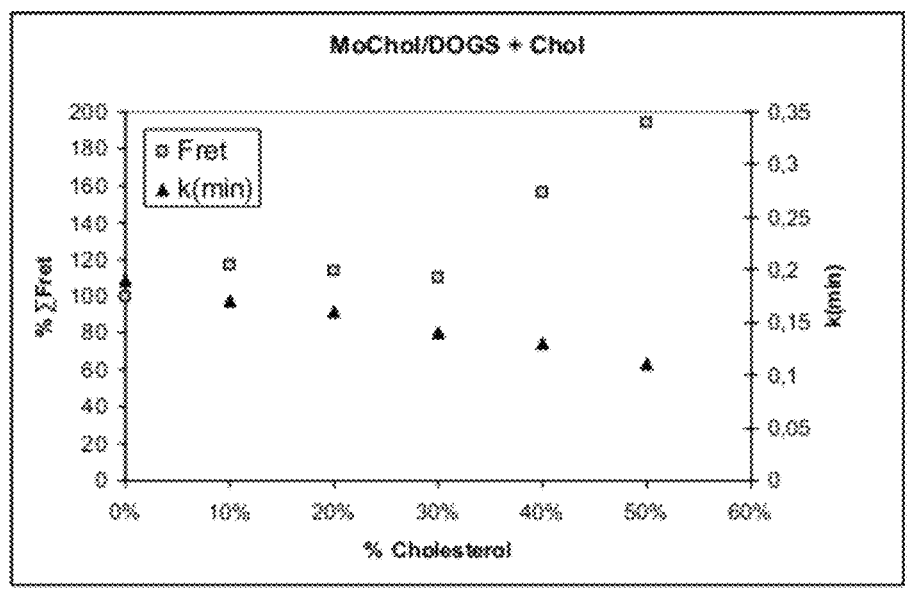
Figure 24A:
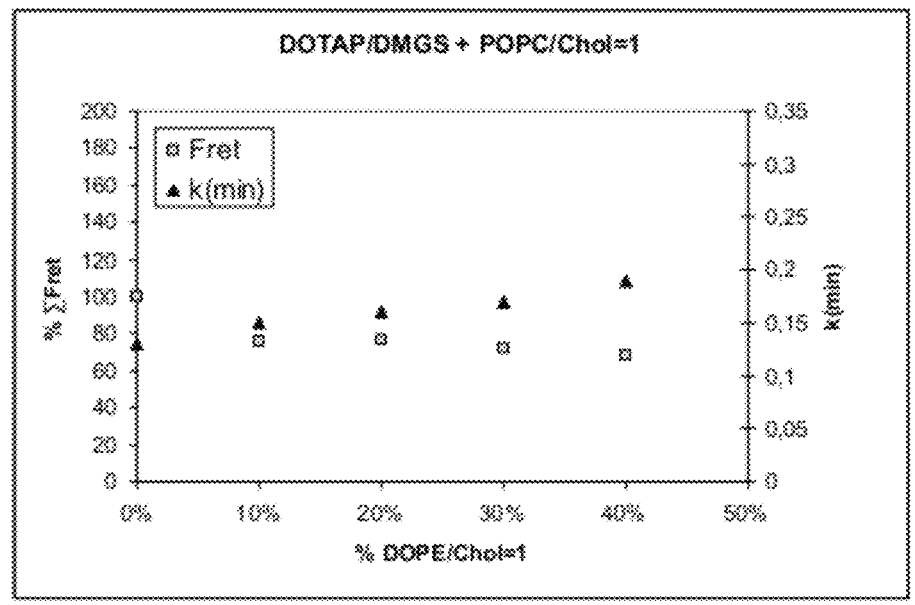
FIGS. 24a and 24b show plots of the intensity of fusion (expressed as % ΣFRET in the matrix C/A=0.17-0.75 for DOTAP/DMGS; C/A=0.33-3 for MoChol/DOGS vs. pH) for liposomes from DOTAP/DMGS or MoChol/DOGS against k(min) for mixtures with 0%-50% of a mixture POPC/cholesterol 1:1. The reference k(min) was modelled for C/A=0.66 (DOTAP/DMGS) or C/A=1 (MoChol/DOGS). The % ΣFRET for 0% POPC/cholesterol is set to 100.
Figure 24B:
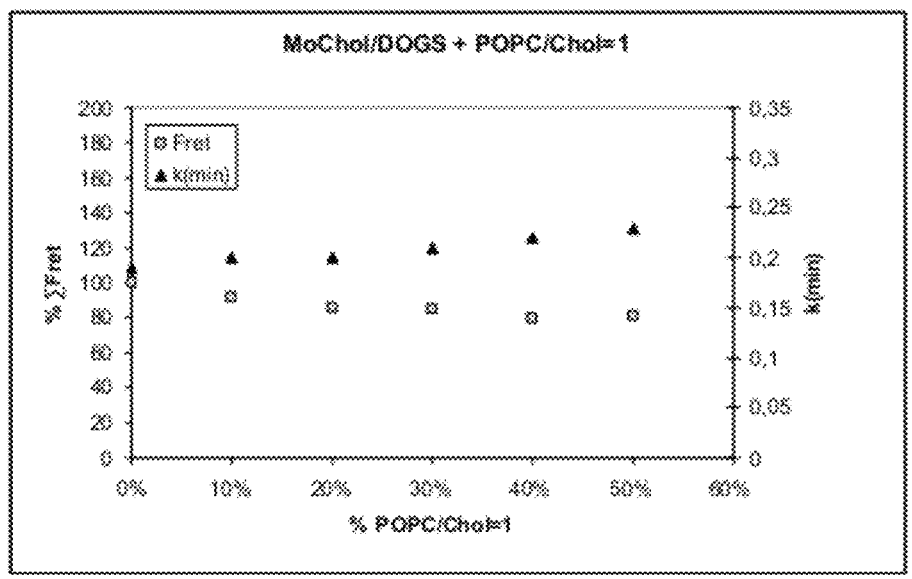
Figure 26:
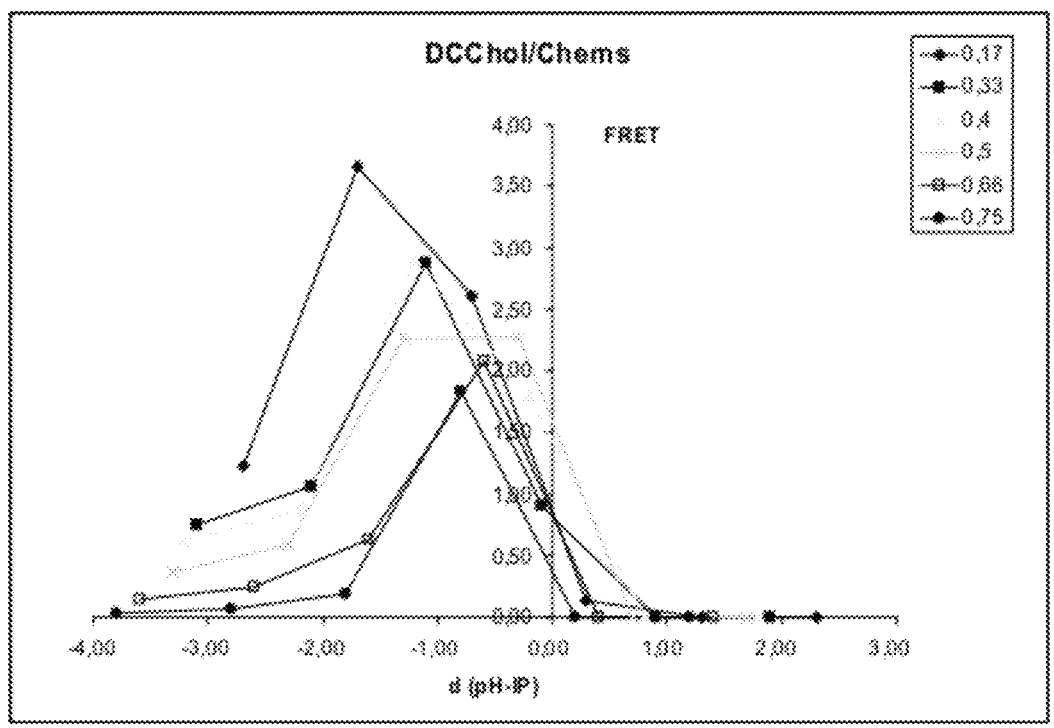
FIG. 26 shows the correlation between the fusion zone and the isoelectric point of liposomes comprising DC-Chol/Chems. d(pH-IP) is the difference between the pH for which FRET was measured and the isoelectric point for the appropriate C/A ratio.

The algorithm presented above according to the invention therefore provides structure-activity relationships between lipid chemistry and stability of the resulting membrane, in particular in response to the pH of the environment. Experimental data further illustrate the invention and justify the model predictions. There is clear evidence for the following:

1. Amphoteric liposomes form stable bilayers at neutral pH, but are fusogenic at intermediate pH. Some amphoteric liposomes form bistable liposomes that exist in a stable phase at low and neutral pHs, but undergo fusion at intermediate pHs. Examples 2, 3, 5 and 6 and corresponding FIGS. 10, 11, 12 and 13 show this for different amphoteric systems and lipid geometries, e.g., lipids with dialkyl- or cholesterol- or monoalkyl membrane anchors.
2. The intensity of fusion may be augmented or diminished through the use of counterions of different size, as shown in Examples 8 and 9 and the corresponding FIGS. 16 and 17.
3. κ(salt) correlates inversely with the fusion intensity of different amphoteric systems. This means that systems with a lower κ(salt) show enhanced fusion. Experimental evidence is given in Examples 12 and 13. FIGS. 19a and 19b show an inverse correlation between fusion intensity (expressed as ΣFRET) and κ(salt) for a large number of amphoter II systems, said systems being formed from cholesterol based pH sensitive cationic lipids and pH sensitive anionic lipids. FIG. 19c illustrates such a plot for the cationic lipid DmC4Mo2 in combination with different anionic pH sensitive lipids. Likewise, FIG. 20 shows such an inverse correlation for amphoter I systems comprising DOTAP or DODAP and various pH sensitive anions. A clear correlation between the value of κ(salt) and the fusogenicity of the amphoteric systems becomes apparent from these experiments.
4. The model also applies to amphoteric lipid mixtures further comprising neutral lipids and the quantitative impact of such admixtures is shown in Examples 15 and corresponding FIGS. 21 to 24. A relation between κ(neutral lipid admixture) and κ(min) is implicit in the model predictions and further described below. In brief, the inclusion of neutral lipids may decrease the fusion intensity of a given amphoteric system whenever κ(neutral) is higher than κ(min). FIGS. 21a,b and 24a,b demonstrate this experimentally. The opposite case can also be found, as demonstrated in the FIGS. 23a,b. Eventually, some systems are less affected by the introduction of neutral lipids, as shown in FIGS. 22a,b. Since experimental optimisation of systems with a higher number of components becomes increasingly difficult and laborious, numerical predictability according to the invention becomes even more important and allows rapid and efficacious prediction.
5. The model predicts fusion around the isoelectric point of the lipid mixture. Such correlation can be demonstrated in the experiment and is analyzed in FIG. 26.

The data provided above show a high degree of predictability from model calculations. The algorithm, starting from molecular volume considerations and rather long range interactions of electrical charges, does not reflect steric fit or misfit of the components; it also does not take phase transition temperatures and the associated molecular movements into account which might occur in isolated cases. In some cases impaired fusion behaviour (e.g. between MoChol and POPG, but not MoChol and DOPA as described above) or enhanced fusion behaviour can be observed (e.g. DmC4Mo2 and various anionic lipids). In cases for which an enhanced fusion behaviour is observed κ(salt) of the lipid salt may be higher than 0.35, but less than 0.45.

Following is an assessment of liposomal fusion for a wide range of amphoteric systems and selected preferred systems for further practical use.

The quantitative structure-activity relationships taught by this invention facilitate in silico screening and support rational selection and optimization. Such screening may be used on its own or in combination with empirical verification, e.g., by the inclusion of selected data points within a series of lipid homologues. The following sections comprise:

Section I: In silico screening of amphoteric systems

Section II: In silico screening of amphoteric systems, further comprising neutral lipids Section III: Experimental screening of amphoteric systems Section IV: Experimental screening of amphoteric systems, further comprising neutral lipids.

Section I: in Silico Screening of Amphoteric Lipids

The present invention enables the selection of amphoteric liposomes for a number of technical purposes. A more detailed analysis is given below of the use of such amphoteric liposomes in pharmaceutical applications. Amongst such pharmaceutical applications, parenteral administration and direct administration into the blood stream of a human or non-human animal, preferably a mammal, is of particular importance. Amphoteric liposomes have specific applicability inter alia in the intracellular delivery of cargo molecules. As described above, during uptake into the cells, liposomes are exposed to an acidic environment in the endosome or lysosome of cells. Destabilisation of the lipid phase, e.g., by enhanced fusogenicity is known to facilitate endosome escape and intracellular delivery. It is possible that other environments of low pH will also trigger said fusion, e.g., the low pH conditions found in tumors or at sites of inflammation.

Amphoteric liposomes according to the present invention with a preferred low value of κ(salt) have been found to respond advantageously to acidification by destabilisation or formation of a fusogenic phase as intended.

To be stable under storage conditions or while in the blood stream, a certain difference between κ(total) at neutral pH and κ(salt) is necessary. In preferred embodiments, such difference, referred to herein as dκ(pH8), may be greater than or to equal 0.08. As noted above, κ(salt) is the dominant predictor for fusogenicity, whereas dκ(pH8)>=0.08 is a necessary, but not sufficient condition. A scoring of selected systems was done using 1/κ(salt) as a metric. High values indicate systems with good fusion and sufficient stability amplitude.

The difference between κ(salt) and κ(total) for acidic conditions is of less importance, since an unstable lipid phase under acidic conditions does not interfere with cellular uptake. In addition, methods to stabilise such lipid phase for production have been described above.

The analysis is sensitive to counter-cation size and the proportion of anionic lipid in the mixture. As mentioned above, larger counter-cations make the selection less stringent, since this parameter directly improves the dκ(pH8) which means that systems with a low amplitude become more functional. It also means that systems with a low κ(salt) can be stabilized sufficiently to yield a stable phase at neutral pH. Although resulting in a more or less stringent selection, the counter-cation size does not change the observed overall pattern of selected systems. This fact effectively compensates the variability of counter-cation sizes that can be found in the literature.

Amphoteric lipid systems with lipid head-group sizes between 40 and 190 $Å^3$ and lipid hydrophobic tail sizes of 340, 410 or 500 $Å^3$ have been analyzed in the presence of a counter-cation, specifically sodium (65 $Å^3$). The counter-anion is of less relevance for the presented screen, since the ion (1) does not participate in the lipid salt and (2) does essentially not bind to the membrane at pH8.

The following in silico screens of amphoter I and amphoter II and III systems provide a more general and experimentally unbiased selection of fusogenic amphoteric liposomes. The calculations allow one skilled in the art to deduce amphiphiles with preferred head and tail sizes and subsequently to identify improved amphoteric lipid mixtures.

The following selections were made according to κ(salt) <0.34 and dκ(pH 8)<=0.08 and identified limits for preferred lipid systems. Other limits for selection can be used, allowing a broader or narrower search for amphoteric lipid systems as desired.

Amphoter I Systems

For amphoter I systems, full dissociation of the anionic amphiphile was assumed at pH 8. A library of 324 amphoter I lipid systems having a C/A=0.5 was constructed and preferred lipid systems having κ(salt)<0.34 and dκ(pH 8)<=0.08 were selected from the entire population.

TABLE 13

Highly functional amphoter I systems (C/A = 0.5, k(salt) < 0.34, dk(pH8) >= 0.08), values represent 1/k(salt)

| Anion | | | Cation head | | | | | | | | | | | | | | | | | |
|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | | | | | | | | | | | | | | | | | | |
| 70 | 340 | 0.21 | | | | | | | 6.82 | | | | | | 7.64 | | | | | |
| 100 | 340 | 0.29 | 4.86 | | | | | | 5.36 | 4.41 | | | | | 6.00 | 4.94 | 4.20 | | | |
| 130 | 340 | 0.38 | 4.00 | 3.40 | | | | | 4.41 | 3.75 | 3.26 | | | | 4.94 | 4.20 | 3.65 | 3.23 | | |
| 160 | 340 | 0.47 | 3.40 | 2.96 | | | | | 3.75 | 3.26 | | | | | 4.20 | 3.65 | 3.23 | | | |
| 190 | 340 | 0.56 | 2.96 | | | | | | 3.26 | | | | | | 3.65 | 3.23 | | | | |
| 40 | 410 | 0.10 | | | | | | | | | | | | | | | | | | |
| 70 | 410 | 0.17 | | | | | | | | | | | | | | | | | | |
| 100 | 410 | 0.24 | | | | | | | | | | | | | 6.50 | | | | | |
| 130 | 410 | 0.32 | 4.41 | | | | | | 4.82 | | | | | | 5.35 | 4.55 | | | | |
| 160 | 410 | 0.39 | 3.75 | 3.26 | | | | | 4.10 | 3.57 | | | | | 4.55 | 3.96 | 3.50 | | | |
| 190 | 410 | 0.46 | 3.26 | | | | | | 3.57 | 3.15 | | | | | 3.96 | 3.50 | 3.14 | | | |
| 40 | 500 | 0.08 | | | | | | | | | | | | | | | | | | |
| 70 | 500 | 0.14 | | | | | | | | | | | | | | | | | | |
| 100 | 500 | 0.20 | | | | | | | | | | | | | | | | | | |
| 130 | 500 | 0.26 | | | | | | | | | | | | | | | | | | |
| 160 | 500 | 0.32 | | | | | | | | | | | | | 5.00 | | | | | |
| 190 | 500 | 0.38 | | | | | | | 3.96 | | | | | | 4.35 | 3.85 | | | | |

The table shows the positively screened systems and further reveals consistent patterns for such systems within specific combinations of lipid tail groups.

The effect of the lipid anion content in amphoter I systems is somewhat more complex. First of all, a lower presence of lipid anion (e.g. C/A 0.666 or 60 mol %) results in a more stringent selection, this is due to the smaller amplitude of such systems. Accordingly, the presence of higher amounts of lipid anion results in a less stringent selection. Results for the respective calculations are presented below.

TABLE 14

Highly functional amphoter I systems (C/A = 0.666, k(salt) < 0.34, dk(pH8) >= 0.08), values represent 1/k(salt)

| Anion | | | Cation head | | | | | | | | | | | | | | | | | |
|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | | | | | | | | | | | | | | | | | | |
| 70 | 340 | 0.21 | | | | | | | | | | | | | | | | | | |
| 100 | 340 | 0.29 | | | | | | | | | | | | | | | | | | |
| 130 | 340 | 0.38 | | | | | | | | | | | | | | | | | | |

TABLE 14-continued

Highly functional amphoter I systems (C/A = 0.666, k(salt) < 0.34, dk(pH8) >= 0.08), values represent 1/k(salt)

| Anion | | | Cation head 40 | 70 | 100 | 130 | 160 | 190 | 40 | 70 | 100 | 130 | 160 | 190 | 40 | 70 | 100 | 130 | 160 | 190 |
|---|---|---|---|---|---|---|---|---|---|---|---|---|---|---|---|---|---|---|---|---|
| | | | tail 340 | 340 | 340 | 340 | 340 | 340 | 410 | 410 | 410 | 410 | 410 | 410 | 500 | 500 | 500 | 500 | 500 | 500 |
| head | tail | k | k 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 160 | 340 | 0.47 | | | | | | | | | | | | | 4.20 | | | | | |
| 190 | 340 | 0.56 | 2.96 | | | | | | 3.26 | | | | | | 3.65 | 3.23 | | | | |
| 40 | 410 | 0.10 | | | | | | | | | | | | | | | | | | |
| 70 | 410 | 0.17 | | | | | | | | | | | | | | | | | | |
| 100 | 410 | 0.24 | | | | | | | | | | | | | | | | | | |
| 130 | 410 | 0.32 | | | | | | | | | | | | | | | | | | |
| 160 | 410 | 0.39 | | | | | | | | | | | | | | | | | | |
| 190 | 410 | 0.46 | | | | | | | | | | | | | | | | | | |
| 40 | 500 | 0.08 | | | | | | | | | | | | | | | | | | |
| 70 | 500 | 0.14 | | | | | | | | | | | | | | | | | | |
| 100 | 500 | 0.20 | | | | | | | | | | | | | | | | | | |
| 130 | 500 | 0.26 | | | | | | | | | | | | | | | | | | |
| 160 | 500 | 0.32 | | | | | | | | | | | | | | | | | | |
| 190 | 500 | 0.38 | | | | | | | | | | | | | | | | | | |

The presence of lower amounts of the anionic lipids results in selection pressure towards sterol based lipid anions with large head groups in combination with cationic lipids of any tail size, provided that these lipids have a minimal head group with a molecular volume between 40 and 70 $Å^3$.

Presence of higher amounts of the anionic lipid lifts said selection pressure and makes the composition more promiscuous in general. It also shifts the optimum size for the lipid anion head group towards moderate values between 100 and 130 $Å^3$ as shown in the table below.

TABLE 15

Highly functional amphoter I systems (C/A = 0.333, k(salt) < 0.34, dk(pH8) >= 0.08), values represent 1/k(salt)

| Anion | | | Cation head 40 | 70 | 100 | 130 | 160 | 190 | 40 | 70 | 100 | 130 | 160 | 190 | 40 | 70 | 100 | 130 | 160 | 190 |
|---|---|---|---|---|---|---|---|---|---|---|---|---|---|---|---|---|---|---|---|---|
| | | | tail 340 | 340 | 340 | 340 | 340 | 340 | 410 | 410 | 410 | 410 | 410 | 410 | 500 | 500 | 500 | 500 | 500 | 500 |
| head | tail | k | k 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | 8.50 | | | | | | 9.38 | 6.82 | | | | | 10.50 | 7.64 | | | | |
| 70 | 340 | 0.21 | 6.18 | 4.86 | | | | | 6.82 | 5.36 | 4.41 | | | | 7.64 | 6.00 | 4.94 | | | |
| 100 | 340 | 0.29 | 4.86 | 4.00 | 3.40 | | | | 5.36 | 4.41 | 3.75 | 3.26 | | | 6.00 | 4.94 | 4.20 | 3.65 | 3.23 | |
| 130 | 340 | 0.38 | 4.00 | 3.40 | 2.96 | | | | 4.41 | 3.75 | 3.26 | | | | 4.94 | 4.20 | 3.65 | 3.23 | | |
| 160 | 340 | 0.47 | 3.40 | 2.96 | | | | | 3.75 | 3.26 | | | | | 4.20 | 3.65 | 3.23 | | | |
| 190 | 340 | 0.56 | 2.96 | | | | | | 3.26 | | | | | | 3.65 | 3.23 | | | | |
| 40 | 410 | 0.10 | | | | | | | | | | | | | 11.38 | | | | | |
| 70 | 410 | 0.17 | 6.82 | | | | | | 7.45 | | | | | | 8.27 | 6.50 | | | | |
| 100 | 410 | 0.24 | 5.36 | 4.41 | | | | | 5.86 | 4.82 | | | | | 6.50 | 5.35 | 4.55 | | | |
| 130 | 410 | 0.32 | 4.41 | 3.75 | 3.26 | | | | 4.82 | 4.10 | 3.57 | | | | 5.35 | 4.55 | 3.96 | 3.50 | | |
| 160 | 410 | 0.39 | 3.75 | 3.26 | | | | | 4.10 | 3.57 | 3.15 | | | | 4.55 | 3.96 | 3.50 | 3.14 | | |
| 190 | 410 | 0.46 | 3.26 | | | | | | 3.57 | 3.15 | | | | | 3.96 | 3.50 | 3.14 | | | |
| 40 | 500 | 0.08 | | | | | | | | | | | | | | | | | | |
| 70 | 500 | 0.14 | | | | | | | | | | | | | | | | | | |
| 100 | 500 | 0.20 | 6.00 | | | | | | 6.50 | | | | | | 7.14 | | | | | |
| 130 | 500 | 0.26 | 4.94 | | | | | | 5.35 | 4.55 | | | | | 5.88 | 5.00 | | | | |
| 160 | 500 | 0.32 | 4.20 | 3.65 | | | | | 4.55 | 3.96 | 3.50 | | | | 5.00 | 4.35 | 3.85 | | | |
| 190 | 500 | 0.38 | 3.65 | 3.23 | | | | | 3.96 | 3.50 | 3.14 | | | | 4.35 | 3.85 | 3.45 | 3.13 | | |

Preferred amphoter I systems may rapidly be identified with the procedures described above, said systems being characterized by
κ(salt) being smaller than 0.34
dκ(pH8) being greater than 0.08
More preferred systems have
smaller lipid anion tail groups with a molecular volume smaller than 420 Å$^3$, selected from the group of sterols or dimyristoylethylenglycols, most preferred this group is a sterol Amphoter II and III systems For amphoter II systems, full dissociation of the anionic amphiphile was assumed at pH 8 and essentially no dissociation of the cationic amphiphile was assumed at this pH. Such selections also apply to amphoter III systems, as long as they contain 50% or less of the anionic amphiphile.

First, a library of 324 amphoter II lipid systems having a C/A=3 was constructed and preferred lipid systems having κ(salt)<0.34 and dκ(pH 8)<=0.08 were selected from this population.

TABLE 16

Highly functional amphoter II systems (C/A = 3, k(salt) < 0.34, dk(pH8) >= 0.08), values represent 1/k(salt)

| anion | | | cation head | | | | | | | | | | | | | | | | | |
|---|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | tail | | | | | | | | | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | k | | | | | | | | | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | | | 4.86 | 4.00 | 3.40 | 2.96 | | | | 4.41 | 3.75 | 3.26 | | | | | | 3.65 |
| 70 | 340 | 0.21 | | | | 3.40 | 2.96 | | | | | | 3.26 | | | | | | | |
| 100 | 340 | 0.29 | | | | | | | | | | | | | | | | | | |
| 130 | 340 | 0.38 | | | | | | | | | | | | | | | | | | |
| 160 | 340 | 0.47 | | | | | | | | | | | | | | | | | | |
| 190 | 340 | 0.56 | | | | | | | | | | | | | | | | | | |
| 40 | 410 | 0.10 | | | 5.36 | 4.41 | 3.75 | 3.26 | | | | 4.82 | 4.10 | 3.57 | | | | | 4.55 | 3.96 |
| 70 | 410 | 0.17 | | | | 3.75 | 3.26 | | | | | | 3.57 | 3.15 | | | | | | 3.50 |
| 100 | 410 | 0.24 | | | | 3.26 | | | | | | | | | | | | | | |
| 130 | 410 | 0.32 | | | | | | | | | | | | | | | | | | |
| 160 | 410 | 0.39 | | | | | | | | | | | | | | | | | | |
| 190 | 410 | 0.46 | | | | | | | | | | | | | | | | | | |
| 40 | 500 | 0.08 | | | 6.00 | 4.94 | 4.20 | 3.65 | | | 6.50 | 5.35 | 4.55 | 3.96 | | | | | 5.00 | 4.35 |
| 70 | 500 | 0.14 | | | 4.94 | 4.20 | 3.65 | 3.23 | | | | 4.55 | 3.96 | 3.50 | | | | | | 3.85 |
| 100 | 500 | 0.20 | | | | 3.65 | 3.23 | | | | | | 3.50 | 3.14 | | | | | | |
| 130 | 500 | 0.26 | | | | | | | | | | | | | | | | | | |
| 160 | 500 | 0.32 | | | | | | | | | | | | | | | | | | |
| 190 | 500 | 0.38 | | | | | | | | | | | | | | | | | | |

In another embodiment, the more preferred systems have
anionic head groups with a molecular volume between 70 Å$^3$ and 190 Å$^3$, said groups are selected from but not limited to hemimalonates, hemisuccinates, hemiglutarates, hemiadipates, cyclohexanoic diacids, glucuronic acids and homologues thereof.
cationic head groups with small molecular volume between 40 and 100 Å$^3$, most preferred between 40 and 70 Å$^3$, said groups being selected from but not limited to methylamine, dimethylamine, trimethylamines, tetramethylammonium salts, N-methylpyridinium salts, trimethyl-hydroxyethylammonium salts, N-a trimethylammoniumacetyl salts, dimethylaminoethylcarbamates, N-Methyl-mono(hydroxymethyl)aminomethane, N-Methyl-bis(hydroxymethyl)aminomethane and homologues thereof.

The most preferred amphoter I systems have low κ(salt) and high dκ(pH8) values in the presence of higher amounts of the lipid cation, thus facilitating better binding and encapsulation of polyanionic cargo molecules such as oligonucleotides. These systems have
a sterol based lipid anion with a polar head group that is larger than 130 Å$^3$, most preferred about 160 to 190 Å$^3$
a dioleoylglycerol based lipid cation with polar head group that is smaller than 100 Å$^3$, most preferred smaller than 70 Å$^3$.

Preferred cation-rich amphoter II (or amphoter III) systems can rapidly be identified with the procedures described above, said systems being characterized by
k(salt) being smaller than 0.34
dk(pH8) being greater than 0.08
lipid cation tail groups with a molecular volume smaller than 420 Å$^3$, selected from the group of sterols or dimyristoylethylenglycols, most preferred this group is a sterol
lipid anion tail groups with a molecular volume larger than 400 Å$^3$, selected from the groups of diacylethylenglycols, most preferred dipalmitoyl-distearoyl-palmitoyloleoyl- or dioleoylethylenglycols.
In another embodiment, the more preferred systems have
cationic head groups with a molecular volume between 70 Å$^3$ and 160 Å$^3$, selected from but not limited to morpholines, propylimidazols, 3-imidazol-1-yl-propyl carbamates, piperazine 4-N-aminoethyl carbamoyls, 2-(4-Imidazolyl)ethylamine hemisuccinates, 1-[2-carboxyethyl] 2-methyl-3-(2-hydroxyethyl) imidazolinium salts, ethylphosphocholines, N-Morpholino ethylamine hemisuccinates, 1-Methyl-4-choline-succinic acid diesters and homologues of said compounds.
anionic head groups with small molecular volume between 40 and 100 Å$^3$, most preferred between 40 and 70 Å$^3$, said groups being selected from but not limited to hemimalonates, hemisuccinates, hemiglutarates and homologues thereof.

Amphoter II systems with about equimolar C/A have more complex selection patterns, but include the aforementioned cation-rich systems. Said systems therefore facilitate tuning of the isoelectric point without loosing functionality. Table 17 below presents systems that were selected in accordance with the criteria presented above:

TABLE 17

Highly functional amphoter II systems (C/A = 1, k(salt) < 0.34, dk(pH8) >= 0.08), values represent 1/k(salt)

| anion | | | \multicolumn{18}{c}{cation head} | | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | 8.50 | 6.18 | 4.86 | 4.00 | 3.40 | 2.96 | 9.38 | 6.82 | 5.36 | 4.41 | 3.75 | | 10.50 | 7.64 | 6.00 | 4.94 | | |
| 70 | 340 | 0.21 | 6.18 | 4.86 | 4.00 | 3.40 | 2.96 | | 6.82 | 5.36 | 4.41 | 3.75 | 3.26 | | 7.64 | 6.00 | 4.94 | 4.20 | 3.65 | |
| 100 | 340 | 0.29 | 4.86 | 4.00 | 3.40 | 2.96 | | | 5.36 | 4.41 | 3.75 | 3.26 | | | 6.00 | 4.94 | 4.20 | 3.65 | 3.23 | |
| 130 | 340 | 0.38 | 4.00 | 3.40 | 2.96 | | | | 4.41 | 3.75 | 3.26 | | | | 4.94 | 4.20 | 3.65 | 3.23 | | |
| 160 | 340 | 0.47 | 3.40 | 2.96 | | | | | 3.75 | 3.26 | | | | | 4.20 | 3.65 | 3.23 | | | |
| 190 | 340 | 0.56 | 2.96 | | | | | | 3.26 | | | | | | 3.65 | 3.23 | | | | |
| 40 | 410 | 0.10 | 9.38 | 6.82 | 5.36 | 4.41 | 3.75 | 3.26 | | | | | | | 11.38 | | | | | |
| 70 | 410 | 0.17 | | 5.36 | 4.41 | 3.75 | 3.26 | | | | | | | | 8.27 | 6.50 | | | | |
| 100 | 410 | 0.24 | | | 3.75 | 3.26 | | | | | | | | | 6.50 | 5.35 | 4.55 | | | |
| 130 | 410 | 0.32 | | | | | | | | | | | | | 5.35 | 4.55 | 3.96 | 3.50 | | |
| 160 | 410 | 0.39 | | | | | | | | | | | | | 4.55 | 3.96 | 3.50 | 3.14 | | |
| 190 | 410 | 0.46 | | | | | | | | | | | | | 3.96 | 3.50 | 3.14 | | | |
| 40 | 500 | 0.08 | | | 6.00 | 4.94 | 4.20 | 3.65 | | | | | | | 4.55 | 3.96 | | | | |
| 70 | 500 | 0.14 | | | | 4.20 | 3.65 | 3.23 | | | | | | | | 3.50 | | | | |
| 100 | 500 | 0.20 | | | | 3.65 | 3.23 | | | | | | | | | | | | | |
| 130 | 500 | 0.26 | | | | | | | | | | | | | | | | | | |
| 160 | 500 | 0.32 | | | | | | | | | | | | | | | | | | |
| 190 | 500 | 0.38 | | | | | | | | | | | | | | | | | | |

In addition to the selection criteria used for cation-rich amphoter II system, the amphoter II (C/A=1) systems display a preference for
 lipid anion tail groups with a molecular volume smaller than 420 $Å^3$, selected from the group of sterols or dimyristoylethylenglycols, most preferred this group is a sterol The anion-rich amphoter II systems are the least demanding ones, as far as structural constraints are concerned. However, this structural freedom comes at the cost of limited encapsulation efficiency for important cargo types, such polyanions, in particular oligonucleotides. The selection screen was applied to amphoter II system with C/A=0.5 and results in the following pattern:

TABLE 18

Highly functional amphoter II systems (C/A = 0.5, k(salt) < 0.34, dk(pH8) >= 0.08), values represent 1/k(salt)

| anion | | | \multicolumn{18}{c}{cation head} | | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | 8.50 | 6.18 | 4.86 | 4.00 | | | 9.38 | 6.82 | 5.36 | 4.41 | | | 10.50 | 7.64 | 6.00 | 4.94 | | |
| 70 | 340 | 0.21 | 6.18 | 4.86 | 4.00 | 3.40 | 2.96 | | 6.82 | 5.36 | 4.41 | 3.75 | 3.26 | | 7.64 | 6.00 | 4.94 | 4.20 | 3.65 | 3.23 |
| 100 | 340 | 0.29 | 4.86 | 4.00 | 3.40 | 2.96 | | | 5.36 | 4.41 | 3.75 | 3.26 | | | 6.00 | 4.94 | 4.20 | 3.65 | 3.23 | |
| 130 | 340 | 0.38 | 4.00 | 3.40 | 2.96 | | | | 4.41 | 3.75 | 3.26 | | | | 4.94 | 4.20 | 3.65 | 3.23 | | |
| 160 | 340 | 0.47 | 3.40 | 2.96 | | | | | 3.75 | 3.26 | | | | | 4.20 | 3.65 | 3.23 | | | |
| 190 | 340 | 0.56 | 2.96 | | | | | | 3.26 | | | | | | 3.65 | 3.23 | | | | |
| 40 | 410 | 0.10 | 9.38 | 6.82 | 5.36 | | | | 10.25 | 7.45 | 5.86 | | | | 11.38 | 8.27 | 6.50 | | | |
| 70 | 410 | 0.17 | 6.82 | 5.36 | 4.41 | 3.75 | | | 7.45 | 5.86 | 4.82 | 4.10 | | | 8.27 | 6.50 | 5.35 | 4.55 | | |
| 100 | 410 | 0.24 | 5.36 | 4.41 | 3.75 | 3.26 | | | 5.86 | 4.82 | 4.10 | 3.57 | 3.15 | | 6.50 | 5.35 | 4.55 | 3.96 | 3.50 | |
| 130 | 410 | 0.32 | 4.41 | 3.75 | 3.26 | | | | 4.82 | 4.10 | 3.57 | 3.15 | | | 5.35 | 4.55 | 3.96 | 3.50 | 3.14 | |
| 160 | 410 | 0.39 | 3.75 | 3.26 | | | | | 4.10 | 3.57 | 3.15 | | | | 4.55 | 3.96 | 3.50 | 3.14 | | |
| 190 | 410 | 0.46 | 3.26 | | | | | | 3.57 | 3.15 | | | | | 3.96 | 3.50 | 3.14 | | | |
| 40 | 500 | 0.08 | 10.50 | | | | | | 11.38 | | | | | | 12.50 | | | | | |

TABLE 18-continued

Highly functional amphoter II systems (C/A = 0.5, k(salt) < 0.34, dk(pH8) >= 0.08), values represent 1/k(salt)

| | | | cation head | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | anion | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 70 | 500 | 0.14 | 7.64 | 6.00 | | | | | 8.27 | 6.50 | | | | | 9.09 | 7.14 | | | | |
| 100 | 500 | 0.20 | 6.00 | 4.94 | | | | | 6.50 | 5.35 | 4.55 | | | | 7.14 | 5.88 | 5.00 | | | |
| 130 | 500 | 0.26 | 4.94 | 4.20 | 3.65 | | | | 5.35 | 4.55 | 3.96 | | | | 5.88 | 5.00 | 4.35 | 3.85 | | |
| 160 | 500 | 0.32 | 4.20 | 3.65 | 3.23 | | | | 4.55 | 3.96 | 3.50 | 3.14 | | | 5.00 | 4.35 | 3.85 | 3.45 | 3.13 | |
| 190 | 500 | 0.38 | 3.65 | 3.23 | | | | | 3.96 | 3.50 | 3.14 | | | | 4.35 | 3.85 | 3.45 | 3.13 | | |

Amphoter II systems with anion excess have a preference for
  cation head groups with a molecular volume of less than 130 $Å^3$, preferred less than 100 $Å^3$, being selected from but not limited to imidazols, methylimidazols, ethylimidazols, morpholins, methylmorpholins, ethylmorphlins, N-Methyl-tris(hydroxymethyl)aminomethanes, 3-imidazol-1-yl-propyl carbamates, piperazine 4-N-aminoethyl carbamoyls, N-Methyl-mono(hydroxymethyl)aminomethanes, N-Methyl-bis(hydroxymethyl) aminomethanes and homologues thereof.
  anionic head groups with a molecular volume of less than 130 $Å^3$, preferred about 70 $Å^3$ or less, being selected from but not limited to hemimalonates, hemisuccinates, hemiglutarates, hemiadipates, cyclohexanoic diacids and homologues thereof.

With more lipid anions in the mixture, the pattern of positively selected candidates resembles this of the amphoter I systems. However, the latter ones are somewhat compromised in their dk(pH8) values as the constant formation of the lipid salt reduces this amplitude.

Section II: in Silico Screening of Amphoteric Systems, Further Comprising Neutral Lipids The algorithm taught by this invention also facilitates quantitative predictions to be made on the effect of neutral lipid admixtures to amphoteric lipid systems. Such admixtures may result in improved stability of the liposome; they might further result in better resistance against serum proteins or enhanced uptake into cells. Optimization of amphoteric systems is a challenging task on its own, owing to the large number of useful components. This task becomes even more complicated with the addition of further components and rational approaches are urgently needed.

The methodology developed in the previous sections above was therefore applied to more complex systems including neutral lipid components. With respect to the main parameters k(salt) and dk(pH8), the addition of neutral lipids may result in
  an increase of k(min) if k(neutral) is higher than k(salt) and vice versa, said increase being proportional to the amount of neutral lipid added.
  a compression of the system amplitude dk(pH8) by addition of any neutral lipid, since these lipids do not change their geometry upon changes in the pH.

Still, even the more complex systems need a certain k(min) to achieve fusion and a certain dk(pH8) to maintain stability. The corresponding values from section 1 have been used for the analysis presented here, which are k(min) being the functional equivalent to k(salt), said k(min)<0.34 and dk(pH8)>0.08.

Amphoter I Systems Further Comprising Neutral Lipids

Libraries of amphoter I systems (C/A=0.333) were constructed as described previously and highly functional systems were selected using k(min)<0.34 and dk(pH8)>0.08 as criteria. Fitness of the selected systems is presented as 1/k(min) in the table below for the addition of 30% cholesterol to the library.

TABLE 19

Highly functional amphoter I systems comprising 30% cholesterol. (C/A = 0.333, k(min) < 0.34 and dk(pH8) > 0.08, values represent 1/k(min)

| | | | Cation head | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | Anion | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | | | | | | | | | | | | | | | | | | |
| 70 | 340 | 0.21 | 8.06 | | | | | | 8.81 | | | | | | 9.76 | 7.85 | | | | |
| 100 | 340 | 0.29 | 6.46 | 5.38 | | | | | 7.07 | 5.90 | | | | | 7.85 | 6.56 | 5.63 | | | |
| 130 | 340 | 0.38 | 5.38 | 4.62 | 4.04 | | | | 5.90 | 5.06 | 4.44 | | | | 6.56 | 5.63 | 4.94 | 4.40 | | |
| 160 | 340 | 0.47 | 4.62 | 4.04 | 3.59 | 3.23 | | | 5.06 | 4.44 | 3.95 | 3.55 | 3.23 | | 5.63 | 4.94 | 4.40 | 3.96 | 3.60 | 3.31 |
| 190 | 340 | 0.56 | 4.04 | 3.59 | 3.23 | | | | 4.44 | 3.95 | 3.55 | 3.23 | 2.96 | | 4.94 | 4.40 | 3.96 | 3.60 | 3.31 | 3.05 |
| 40 | 410 | 0.10 | | | | | | | | | | | | | | | | | | |

TABLE 19-continued

Highly functional amphoter I systems comprising 30% cholesterol. (C/A = 0.333, k(min) < 0.34 and dk(pH8) > 0.08, values represent 1/k(min))

| | | | Cation head | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | Anion | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 70 | 410 | 0.17 | | | | | | | | | | | | | | | | | | |
| 100 | 410 | 0.24 | | | | | | | 7.67 | | | | | | 8.44 | | | | | |
| 130 | 410 | 0.32 | 5.90 | | | | | | 6.41 | 5.51 | | | | | 7.06 | 6.07 | | | | |
| 160 | 410 | 0.39 | 5.06 | 4.44 | | | | | 5.51 | 4.83 | 4.30 | | | | 6.07 | 5.33 | 4.74 | 4.28 | | |
| 190 | 410 | 0.46 | 4.44 | 3.95 | 3.55 | | | | 4.83 | 4.30 | 3.87 | 3.52 | | | 5.33 | 4.74 | 4.28 | 3.89 | 3.57 | |
| 40 | 500 | 0.08 | | | | | | | | | | | | | | | | | | |
| 70 | 500 | 0.14 | | | | | | | | | | | | | | | | | | |
| 100 | 500 | 0.20 | | | | | | | | | | | | | | | | | | |
| 130 | 500 | 0.26 | | | | | | | | | | | | | | | | | | |
| 160 | 500 | 0.32 | | | | | | | 6.07 | | | | | | 6.63 | | | | | |
| 190 | 500 | 0.38 | 4.94 | | | | | | 5.33 | | | | | | 5.82 | 5.19 | | | | |

In comparison with the data presented for the corresponding amphoter I library from section I, the addition of cholesterol results in a somewhat different selection that is more biased towards anionic lipids with large headgroups, while maintaining other features like the preference of amphoter I for cholesterol or dimyristoylglycol as tail regions for the anionic lipids.

Addition of a strongly lamellar lipid such as POPC or DOPC results in more stringent selection without qualitative impact on the selection rules presented before.

Amphoter II Systems Further Comprising Neutral Lipids

Libraries of cation-rich amphoter II systems (C/A=3) were constructed as described previously and highly functional systems were selected using k(min)<0.34 and dk(pH8)>0.08 as criteria. Fitness of the selected systems is presented as 1/k(min) in Table 20 below for the addition of 30% cholesterol to the library.

TABLE 20

Highly functional amphoter II systems comprising 30% cholesterol. (C/A = 3, k(min) < 0.34 and dk(pH8) > 0.08, values represent 1/k(min))

| | | | cation head | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | anion | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | | | | 4.62 | 4.04 | | | | | | | | | | | 4.44 | | |
| 70 | 340 | 0.21 | | | | | 3.59 | | | | | | | | | | | | | |
| 100 | 340 | 0.29 | | | | | | | | | | | | | | | | | | |
| 130 | 340 | 0.38 | | | | | | | | | | | | | | | | | | |
| 160 | 340 | 0.47 | | | | | | | | | | | | | | | | | | |
| 190 | 340 | 0.56 | | | | | | | | | | | | | | | | | | |
| 40 | 410 | 0.10 | | | | 5.90 | 5.06 | 4.44 | | | | | | | | | | 4.83 | | |
| 70 | 410 | 0.17 | | | | | 4.44 | 3.95 | | | | | | | | | | | | |
| 100 | 410 | 0.24 | | | | | | 3.55 | | | | | | | | | | | | |
| 130 | 410 | 0.32 | | | | | | | | | | | | | | | | | | |
| 160 | 410 | 0.39 | | | | | | | | | | | | | | | | | | |
| 190 | 410 | 0.46 | | | | | | | | | | | | | | | | | | |
| 40 | 500 | 0.08 | | | | 6.56 | 5.63 | 4.94 | | | | | | | | | | 6.07 | 5.33 | |
| 70 | 500 | 0.14 | | | | 5.63 | 4.94 | 4.40 | | | | | | | | | | | 4.74 | |
| 100 | 500 | 0.20 | | | | | 4.40 | 3.96 | | | | | | | | | | | | |
| 130 | 500 | 0.26 | | | | | | 3.60 | | | | | | | | | | | | |
| 160 | 500 | 0.32 | | | | | | 3.31 | | | | | | | | | | | | |
| 190 | 500 | 0.38 | | | | | | | | | | | | | | | | | | |

In comparison with the data presented for the corresponding cation-rich amphoter II library from section I, the addition of cholesterol results in a somewhat different selection that is substantially biased towards cationic lipids with large headgroups, while maintaining other features like the preference of amphoter I for large tails regions such as dimyristoylglycol or dioleoylglycol for the anionic lipids.

Addition of a lamellar lipid such as POPC or DOPC results in more stringent selection without qualitative impact on the selection rules presented before.

Libraries of equilibrated amphoter II systems (C/A=1) were also constructed and introduced into the selection scheme in the presence of 30% cholesterol in this the library.

TABLE 21

Highly functional amphoter II systems comprising 30% cholesterol. (C/A = 1, k(min) < 0.34 and dk(pH8) > 0.08, values represent 1/k(min))

| anion | | | cation head | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | | | | | | | | | | | | | | | | | | |
| 70 | 340 | 0.21 | | | | | | | | | | | | | | | | | | |
| 100 | 340 | 0.29 | | | | | | | | | | | | | 7.85 | | | | | |
| 130 | 340 | 0.38 | | | | | | | | | | | | | 6.56 | 5.63 | | | | |
| 160 | 340 | 0.47 | | | | | | | | | | | | | 5.63 | 4.94 | 4.40 | 3.96 | | |
| 190 | 340 | 0.56 | | | | | | 4.44 | | | | | | | 4.94 | 4.40 | 3.96 | 3.60 | 3.31 | |
| 40 | 410 | 0.10 | | | | | | | | | | | | | | | | | | |
| 70 | 410 | 0.17 | | | | | | | | | | | | | | | | | | |
| 100 | 410 | 0.24 | | | | | | | | | | | | | | | | | | |
| 130 | 410 | 0.32 | | | | | | | | | | | | | | | | | | |
| 160 | 410 | 0.39 | | | | | | | | | | | | | | | | | | |
| 190 | 410 | 0.46 | | | | | | | | | | | | | | | | | | |
| 40 | 500 | 0.08 | | | | | | | | | | | | | | | | | | |
| 70 | 500 | 0.14 | | | | | | | | | | | | | | | | | | |
| 100 | 500 | 0.20 | | | | | | | | | | | | | | | | | | |
| 130 | 500 | 0.26 | | | | | | | | | | | | | | | | | | |
| 160 | 500 | 0.32 | | | | | | | | | | | | | | | | | | |
| 190 | 500 | 0.38 | | | | | | | | | | | | | | | | | | |

While the corresponding amphoter II library (C/A=1) from section I had numerous positive systems, the addition of 30% cholesterol resulted in a very stringent selection. This is counterintuitive to the addition of a lipid that promotes fusion and illustrates the impact of dk(pH8) as a selection criterium. A close group can be identified comprising:

sterol based lipid anions with head group volumes greater than 100 $A^3$ diacylgylcol based cations with head group volumes smaller than 160 $A^3$, more preferred smaller than 70 $A^3$ In this group, the addition of a lamellar lipid such as POPC or DOPC had similar impact than the addition of cholesterol.

Libraries of anion-rich amphoter II systems (C/A=0.33) were also constructed and introduced into the selection scheme in the presence of 30% cholesterol in this the library.

TABLE 22

Highly functional amphoter II systems comprising 30% cholesterol. (C/A = 0.333, k(min) < 0.34 and dk(pH8) > 0.08, values represent 1/k(min))

| anion | | | cation head | | | | | | | | | | | | | | | | | |
|---|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 40 | 340 | 0.12 | 10.74 | 8.06 | | | | | 11.70 | 8.81 | | | | | 12.91 | 9.76 | 7.85 | | | |
| 70 | 340 | 0.21 | 8.06 | 6.46 | 5.38 | | | | 8.81 | 7.07 | 5.90 | | | | 9.76 | 7.85 | 6.56 | 5.63 | | |
| 100 | 340 | 0.29 | 6.46 | 5.38 | 4.62 | 4.04 | | | 7.07 | 5.90 | 5.06 | 4.44 | 3.95 | | 7.85 | 6.56 | 5.63 | 4.94 | 4.40 | |
| 130 | 340 | 0.38 | 5.38 | 4.62 | 4.04 | 3.59 | 3.23 | | 5.90 | 5.06 | 4.44 | 3.95 | 3.55 | 3.23 | 6.56 | 5.63 | 4.94 | 4.40 | 3.96 | 3.60 |
| 160 | 340 | 0.47 | 4.62 | 4.04 | 3.59 | 3.23 | 2.94 | | 5.06 | 4.44 | 3.95 | 3.55 | 3.23 | 2.96 | 5.63 | 4.94 | 4.40 | 3.96 | 3.60 | 3.31 |
| 190 | 340 | 0.56 | 4.04 | 3.59 | 3.23 | 2.94 | | | 4.44 | 3.95 | 3.55 | 3.23 | 2.96 | | 4.94 | 4.40 | 3.96 | 3.60 | 3.31 | 3.05 |
| 40 | 410 | 0.10 | 11.70 | | | | | | 12.64 | | | | | | 13.82 | | | | | |
| 70 | 410 | 0.17 | 8.81 | | | | | | 9.55 | 7.67 | | | | | 10.48 | 8.44 | | | | |
| 100 | 410 | 0.24 | 7.07 | 5.90 | | | | | 7.67 | 6.41 | 5.51 | | | | 8.44 | 7.06 | 6.07 | | | |
| 130 | 410 | 0.32 | 5.90 | 5.06 | 4.44 | | | | 6.41 | 5.51 | 4.83 | 4.30 | | | 7.06 | 6.07 | 5.33 | 4.74 | 4.28 | |
| 160 | 410 | 0.39 | 5.06 | 4.44 | 3.95 | 3.55 | | | 5.51 | 4.83 | 4.30 | 3.87 | 3.52 | | 6.07 | 5.33 | 4.74 | 4.28 | 3.89 | 3.57 |
| 190 | 410 | 0.46 | 4.44 | 3.95 | 3.55 | 3.23 | 2.96 | | 4.83 | 4.30 | 3.87 | 3.52 | 3.23 | 2.98 | 5.33 | 4.74 | 4.28 | 3.89 | 3.57 | 3.30 |
| 40 | 500 | 0.08 | | | | | | | | | | | | | | | | | | |
| 70 | 500 | 0.14 | | | | | | | | | | | | | | | | | | |
| 100 | 500 | 0.20 | | | | | | | 8.44 | | | | | | 9.19 | | | | | |
| 130 | 500 | 0.26 | 6.56 | | | | | | 7.06 | 6.07 | | | | | 7.70 | 6.63 | | | | |

TABLE 22-continued

Highly functional amphoter II systems comprising 30% cholesterol. (C/A = 0.333, k(min) < 0.34 and dk(pH8) > 0.08, values represent 1/k(min)

| | | | cation head | | | | | | | | | | | | | | | | |
|---|---|---|---|---|---|---|---|---|---|---|---|---|---|---|---|---|---|---|---|
| | | | 40 | 70 | 100 | 130 | 160 | 190 | 40 | 70 | 100 | 130 | 160 | 190 | 40 | 70 | 100 | 130 | 160 | 190 |
| | | | | | | | | | | | tail | | | | | | | | | |
| | | | 340 | 340 | 340 | 340 | 340 | 340 | 410 | 410 | 410 | 410 | 410 | 410 | 500 | 500 | 500 | 500 | 500 | 500 |
| | anion | | | | | | | | | | k | | | | | | | | | |
| head | tail | k | 0.12 | 0.21 | 0.29 | 0.38 | 0.47 | 0.56 | 0.10 | 0.17 | 0.24 | 0.32 | 0.39 | 0.46 | 0.08 | 0.14 | 0.20 | 0.26 | 0.32 | 0.38 |
| 160 | 500 | 0.32 | 5.63 | 4.94 | | | | | 6.07 | 5.33 | | | | | 6.63 | 5.82 | 5.19 | | | |
| 190 | 500 | 0.38 | 4.94 | 4.40 | | | | | 5.33 | 4.74 | 4.28 | | | | 5.82 | 5.19 | 4.68 | 4.26 | | |

Here, some bias of the positive candidates towards larger anion head groups can be observed. However, this needs to be interpreted carefully since the fusion activity is always improving in the presence of small anionic headgroups.

Addition of lamellar lipids such as POPC or DOPC imply more stringent selection criteria in comparison to the systems in section I, but do not qualitatively change the pattern of positive candidates.

Section III: Experimental Screen of Amphoteric Lipid Systems

The fusogenicity of different amphoteric liposome mixtures comprising charged amphiphiles can be investigated using lipid fusion assays, particle growth or other methods known in the art, thereby allowing the identification of preferred mixtures. Lipid mixing can be tested with fluorescence resonance energy transfer (FRET), and experimental details are described in Example 11 wherein the fusion of amphoteric lipid mixtures was monitored within a pH range of between pH 2.5 and pH 7.5.

Amphoter I Systems Comprising Charged Amphiphiles Only

Amphoter I systems are characterized by a stable cation in combination with an excess of a chargeable anion. Preferred amphoter I systems solely comprising charged amphiphiles form stable lamellar phases at pH 7 to pH 8 and fuse between pH 3 to pH 6, preferably between pH 4 to pH 6. Within a given amphoter I system fusion was monitored for different ratios of cationic to anionic lipid (C/A ratio, always <1).

Amphoter I systems that are stable at pH 7 to pH 8 and fuse between pH 3 to pH 6, preferably between pH 4 to pH 6 may be formed from mixtures of one or more cationic amphiphiles selected from DOTAP, DMTAP, DPTAP, DSTAP, POTAP, DDAB, DODAC, DOEPC, DMEPC, DPEPC, DSEPC, POEPC, DC-Chol, TC-Chol, DAC-Chol, DODAP, DMTAP, DPDAP, DSDAP, PODAP, N-methyl-PipChol, CTAB, DOTMA with one or more anionic amphiphile selected from diacylglycerol succinates, e.g. DOGS, DMGS, POGS; diacylglycerolmalonates, e.g. DOGM or DMGM; diacylglycerolglutarates, e.g. DOGG, DMGG; diacylglyceroladipates, e.g. DOGA, DMGA; 4-{(1,2-Diacyl-ethyl)amino}-4-oxo acids, e.g. DOAS, DOAM, DOAG, DOAA, DMAS, DMAM, DMAG, DMAA; Diacyl-alkanoic acids, e.g. DOS, DOM, DOG, DOA, DMS, DMM, DMG, DMA; Chems and derivatives thereof, e.g. Chol-C3, Chol-C5 or Chol-C6; fatty acids.

In one embodiment of the invention, the cationic amphiphiles are selected from DODAP, DOTAP, N-methyl-PipChol, DDAB, DOEPC, DC-Chol, DAC-Chol or TC-Chol and combined with anionic amphiphiles selected from Chems, DMGS, DMGM, DMGG, DMGA, DMAS, DMAM, DMAG, DMAA, DOGS, DOGM, DOGG, DOGA, DOAS, DOAM, DOAG, DOAA, DMS, DMM, DMG, DMA, DOS, DOM, DOG, DOA, Chol-C3, Chol-C5 or Chol-C6.

In some embodiments of the invention the following amphoter I mixtures are preferred which comprise charged amphiphiles only, are stable at pH 7 to pH 8 and fuse between pH 3 to pH 6, preferably between pH 4 to pH 6 (Table 23):

TABLE 23

| Cation | Anion | C/A (molar ratio) |
|---|---|---|
| DODAP | DMGS | >0-<1 |
| DODAP | DOGS | >0-<1 |
| DODAP | Chems | >0-<1 |
| DOTAP | OA | >0-0.33 |
| N-methyl-PipChol | DMGS | >0-<1 |
| N-methyl-PipChol | DOGS | >0-<1 |
| N-methyl-PipChol | Chems | >0-<1 |
| DDAB | DMGS | >0-0.5 |
| DDAB | DOGS | >0-0.5 |
| DOEPC | DMGS | >0-0.5 |
| DOEPC | DOGS | >0-0.5 |
| DOEPC | Chems | >0-0.5 |
| DC-Chol | DOGS | >0-<1 |
| DOTAP | DMGS | >0-0.5 |
| DC-Chol | DMGS | >0-<1 |
| DC-Chol | Chems | >0-<1 |
| CTAB | DMGS | >0-0.5 |
| TC-Chol | DMGS | >0-0.67 |
| TC-Chol | DOGS | >0-0.67 |
| TC-Chol | Chems | >0-0.67 |
| DOTAP | Chol-C3 | ≥0.5-0.67 |
| DOTAP | Chol-C5 | >0-0.4 |
| DOTAP | Chems | >0-0.4 |
| DOTAP | DOGS | >0-0.4 |
| DOTAP | Chol-C6 | >0-0.17 |
| DDAB | Chems | >0-0.17 |

Less preferred are amphoter I systems that are not stable at pH 7 to pH 8, for example the amphoter I systems DOTAP/stearic acid or DOTAP/oleic acid at C/A>0.33.

More versatile amphoter I systems of Table 23 are those that are fusogenic over a wide range of C/A ratios, thus allowing adjustment of the fusion pH without changing the chemistry of the system. Some versatile systems are fusogenic over C/A ratios that differ by ≥0.4, more versatile systems retain fusogenicity for C/A ratios that differ by >0.6 and some system are fusogenic over the entire range of C/A ratios. For example, the amphoter I system DDAB/DMGS shows fusion from C/A>0 to C/A=0.5. The range of C/A ratios for which this system is fusogenic is about 0.5.

Preferred amphoteric mixtures of Table 23 are fusogenic at higher C/A ratios, preferably at C/A≥0.4, and more preferably at C/A ratios ≥0.5, thus facilitating the encapsulation of higher amounts of polyanionic cargoes, such as nucleic acids.

In another embodiment of the invention, the amphoter I systems may form a second stable phase at an acidic pH of between pH 2 to pH 4 in addition to the aforementioned stable lamellar phase at pH 7 to pH 8. However, as described before a stable lamellar phase at low pH is not mandatory and, e.g., for the production of amphoteric liposomes and the encapsulation of cargo under acidic conditions large counter-anions may stabilize the lipid phase at this pH range.

Preferred fusogenic amphoter I systems comprising charged amphiphiles only and having stable lamellar phases at pH 7 to pH 8 and at pH 2 to pH 4 and fusing between pH 3 and pH 6, preferably between pH 4 and pH 6 may comprise the following specific mixtures (Table 24):

TABLE 24

| Cation | Anion | C/A (molar ratio) |
|---|---|---|
| DODAP | DMGS | ≥0.5-<1 |
| DOTAP | OA | 0.17 |
| N-methyl-PipChol | DMGS | ≥0.5-<1 |
| DDAB | DMGS | 0.5 |
| DOEPC | DMGS | ≥0.33-0.5 |
| DC-Chol | DOGS | ≥0.33-<1 |
| DOTAP | DMGS | ≥0.4-0.5 |
| DC-Chol | DMGS | ≥0.5-<1 |
| DC-Chol | Chems | ≥0.4-<1 |
| CTAB | DMGS | 0.5 |
| TC-Chol | DMGS | ≥0.4-0.67 |
| DOTAP | Chol-C3 | ≥0.5-0.67 |
| DOTAP | Chol-C5 | ≥0.33-0.4 |
| DOTAP | Chems | ≥0.33-0.4 |
| DOTAP | DOGS | >0-0.4 |
| DDAB | Chems | 0.17 |

Versatile amphoter I systems of Table 14 are fusogenic over a wide range of C/A ratios, preferably over a range of C/A ratios of ≥0.4, and more preferably over a range of C/A ratios of >0.6.

Furthermore, preferred are the amphoteric mixtures of Table 24 above that are fusogenic at higher C/A ratios, preferably at C/A ≥0.4, and more preferably at C/A ratios ≥0.5.

Amphoter II Systems Comprising Charged Amphiphiles Only

Amphoter II systems comprise chargeable anions and chargeable cations and have therefore the advantage of being amphoteric over the entire range of anion: cation ratios. No charge overcompensation for the strong ion is needed as in Amphoter I or Amphoter III systems.

Amphoter II systems that are stable at pH 7 to pH 8 and fuse between pH 3 to pH 6, preferably between pH 4 to pH 6 may include mixtures of one or more cationic amphiphiles selected from MoChol, HisChol, Chim, MoC3Chol, DmC4Mo2, DmC3Mo2, C3Mo2, C5Mo2, C6Mo2, C8Mo2, C4Mo4, DOIM or DPIM with one or more anionic amphiphile selected from diacylglycerol succinates, like DOGS, DMGS, POGS; diacylglycerolmalonates, like DOGM or DMGM; diacylglycerolglutarates, e.g. DOGG, DMGG; diacylglyceroladipates, e.g. DOGA, DMGA; 4-{(1, 2-Diacyl-ethyl)amino}-4-oxo acids, e.g. DOAS, DOAM, DOAG, DOAA, DMAS, DMAM, DMAG, DMAA; Diacyl-alkanoic acids, like DOS, DOM, DOG, Chems and derivatives thereof, e.g. Chol-C3, Chol-C5 or Chol-C6; fatty acids.

In one embodiment of the invention, the cationic amphiphiles are selected from MoChol, HisChol, Chim, MoC3Chol, DmC4Mo2, DmC3Mo2, C3Mo2, C5Mo2, C6Mo2, C8Mo2, C4Mo4, DOIM or DPIM and combined with anionic amphiphiles selected from Chems, DMGS, DMGM, DMGG, DMGA, DMAS, DMAM, DMAG, DMAA, DOGS, DOGM, DOGG, DOGA, DOAS, DOAM, DOAG, DOAA, DMS, DMM, DMG, DMA, DOS, DOM, DOG, DOA, Chol-C3, Chol-C5 or Chol-C6.

In some embodiments of the invention, amphoter II systems comprising charged amphiphiles only that are stable at pH 7 to pH 8 and fuse between pH 3 to pH 6, preferably between pH 4 to pH 6, are preferred (Table 25):

TABLE 25

| Cation | Anion | C/A (molar ratio) |
|---|---|---|
| DmC4Mo2 | DOGS | >0 |
| DmC4Mo2 | Chems | >0 |
| DmC4Mo2 | DMGS | >0 |
| DmC4Mo2 | Chol-C5 | >0-2 |
| DmC4Mo2 | Chol-C3 | ≥0.7 |
| DmC4Mo2 | Chol-C6 | >0-2 |
| Chim | DMGS | >0-2 |
| Chim | Chems | >0-1.5 |
| Chim | DOGS | >0-1 |
| HisChol | DOGS | >0-0.7 |
| HisChol | Chems | >0-0.7 |
| HisChol | DMGS | >0-0.7 |
| MoC3Chol | DOGS | >0-0.7 |
| MoC3Chol | Chems | >0-0.7 |
| MoC3Chol | DMGS | >0-0.7 |
| DmC3Mo2 | DOGS | >0-1.5 |
| DmC3Mo2 | Chems | >0-1 |
| DmC3Mo2 | DMGS | >0-1.5 |
| C3Mo2 | DOGS | >0-2 |
| C3Mo2 | Chems | >0-1 |
| C3Mo2 | DMGS | >0-2 |
| C3Mo3 | DOGS | >0-0.7 |
| C3Mo3 | Chems | >0-0.7 |
| C3Mo3 | DMGS | >0-0.7 |
| C4Mo4 | DOGS | >0-0.7 |
| C4Mo4 | Chems | >0-0.5 |
| C4Mo4 | DMGS | >0-0.7 |
| C5Mo2 | DOGS | >0-1 |
| C5Mo2 | Chems | >0-0.7 |
| C5Mo2 | DMGS | >0-1 |
| C6Mo2 | DOGS | >0-1 |
| C6Mo2 | Chems | >0-1 |
| C6Mo2 | DMGS | >0-1 |
| C8Mo2 | DOGS | >0-1 |
| C8Mo2 | Chems | >0-0.7 |
| C8Mo2 | DMGS | >0-1 |
| MoChol | DOGS | >0-1 |
| MoChol | Chems | >0-0.7 |
| MoChol | Chol-C3 | >0-0.7 |
| MoChol | Chol-C5 | >0-0.7 |
| MoChol | DMGS | >0-0.7 |
| MoChol | Chol-C6 | >0-0.5 |
| DOIM | DOGS | >0-0.7 |
| DOIM | Chems | >0-0.7 |
| DOIM | DMGS | >0-0.7 |

More versatile amphoter II systems of Table 25 are those that are fusogenic over a wide range of C/A ratios, thus allowing adjustment of the fusion pH without changing the chemistry of the system. Some versatile systems are fusogenic over C/A ratios that differ by ≥0.7, more versatile systems retain fusogenicity for C/A ratios that differ by ≥1 and some systems are fusogenic over the entire range of C/A ratios. For example, the amphoter I system DDAB/DMGS shows fusion from C/A>0 to C/A=0.5. The range of C/A ratios for which this system is fusogenic is about 0.5. For example, the mixture Chim/Chems may fuse between C/A>0 and C/A=1.5, resulting in a range of C/A ratios of >1.

Preferred amphoter II mixtures of Table 25 are fusogenic at higher C/A ratios, preferably at C/A≥0.7, and more preferably at C/A ratios≥1, thus facilitating the encapsulation of higher amounts of polyanionic cargoes such as nucleic acids.

In another embodiment of the invention, amphoter II systems may form a second stable phase at an acidic pH of between pH 2 and pH 4 in addition to the aforementioned stable lamellar phase at pH 7 to pH 8. However, as described before, a stable lamellar phase at low pH is not mandatory and, e.g., for the production of amphoteric liposomes and the encapsulation of cargo under acidic conditions, large counteranions may stabilize the lipid phase at this pH range.

Further preferred are the following fusogenic amphoter II systems comprising charged amphiphiles only and having both a stable lamellar phase at pH 7 to pH 8 and at pH 2 to pH 4 and fusing between pH 3 and pH 6, preferably between pH 4 and pH 6 (Table 26):

TABLE 26

| Cation | Anion | C/A (molar ratio) |
|---|---|---|
| DmC4Mo2 | DOGS | ≥0.7 |
| HisChol | DOGS | 0.7 |
| Chim | DMGS | ≥0.5-2 |
| DmC4Mo2 | Chol-C3 | ≥1.5 |
| DmC4Mo2 | Chems | ≥1 |
| Chim | Chems | ≥0.5-1.5 |
| Chim | DOGS | >0-1 |
| C3Mo2 | DOGS | ≥0.5-2 |
| DmC4Mo2 | DMGS | ≥1 |
| DmC4Mo2 | Chol-C5 | ≥1-2 |
| DmC3Mo2 | DOGS | >0-1.5 |
| MoC3Chol | DOGS | 0.7 |
| MoChol | DOGS | ≥0.5-1 |
| DmC4Mo2 | Chol-C6 | ≥0.5-2 |
| C3Mo2 | Chems | ≥0.7-1 |
| C8Mo2 | DOGS | >0-1 |
| HisChol | Chems | >0-0.7 |
| C5Mo2 | DOGS | >0-1 |
| C6Mo2 | Chems | ≥0.7-1 |
| C5Mo2 | Chems | 0.7 |
| C6Mo2 | DOGS | >0-1 |
| MoChol | Chems | ≥0.5-0.7 |
| C3Mo3 | Chems | ≥0.5-0.7 |
| DmC3Mo2 | Chems | ≥0.5-1 |
| MoChol | Chol-C3 | 0.7 |
| C8Mo2 | Chems | ≥0.5-0.7 |
| C3Mo3 | DOGS | >0-0.7 |
| C4Mo4 | DOGS | >0-0.7 |
| MoChol | Chol-C5 | ≥0.5-0.7 |
| MoChol | DMGS | ≥0.5-0.7 |
| C4Mo4 | Chems | 0.5 |
| DOIM | DOGS | >0-0.7 |
| MoChol | Chol-C6 | >0-0.5 |

Versatile amphoter II systems of Table 26 are fusogenic over a wide range of C/A ratios, preferably over a range of C/A ratios of ≥0.7, more preferably over a range C/A ratios of ≥1. Furthermore, preferred are the amphoteric mixtures of Table 26 that are fusogenic at higher C/A ratios, preferably at C/A ≥0.4, and more preferably at C/A ratios ≥0.5.

Amphoter III Systems of Solely Charged Amphiphiles

Amphoter III systems are characterized by a stable anion and a pH-sensitive cation. Thus amphoter III systems cannot form lipid salts at neutral pH, since little to no charged cationic lipid exists at this pH. Ongoing acidification is needed first to create the cation which then may undergo salt formation.

Amphoter III systems that are stable at pH 7 to pH 8 and fuse between pH 3 to pH 6, preferably between pH 4 to pH 6 may include mixtures of one or more cationic amphiphiles selected from MoChol, HisChol, Chim, MoC3Chol, DmC4Mo2, DmC3Mo2, C3Mo2, C5Mo2, C6Mo2, C8Mo2, C4Mo4, DOIM or DPIM with one or more anionic amphiphile selected from DOPA, DMPA, DPPA, POPA, DSPA, Chol-SO$_4$, DOPG, DMPG, DPPG, POPG, DSPG or DOPS, DMPS, DPPS, POPS and DSPS.

Less preferred are amphoter III systems which do not show fusion owing to steric hindrance. One example that has been described above is the amphoter III system MoChol/POPG.

Preferred amphoter III systems comprising charged amphiphiles only that are stable at pH 7 to pH 8 and fuse between pH 3 and pH 6, preferably between pH 4 and pH 6 include the following specific mixtures (Table 27):

TABLE 27

| Cation | Anion | C/A (molar ratio) |
|---|---|---|
| MoChol | DOPA | >1-1.5 |
| HisChol | DOPA | >1-2 |
| Chim | DOPS | >1-2 |

Among these amphoter III mixtures further preferred are the following mixtures having stable lamellar phase at pH 7 to pH 8 as well as stable phase at an acidic pH of between pH 2 and pH 4 (Table 28):

TABLE 28

| Cation | Anion | C/A (molar ratio) |
|---|---|---|
| MoChol | DOPA | >1-1.5 |
| HisChol | DOPA | 2 |
| Chim | DOPS | >1-2 |

Figure 9:
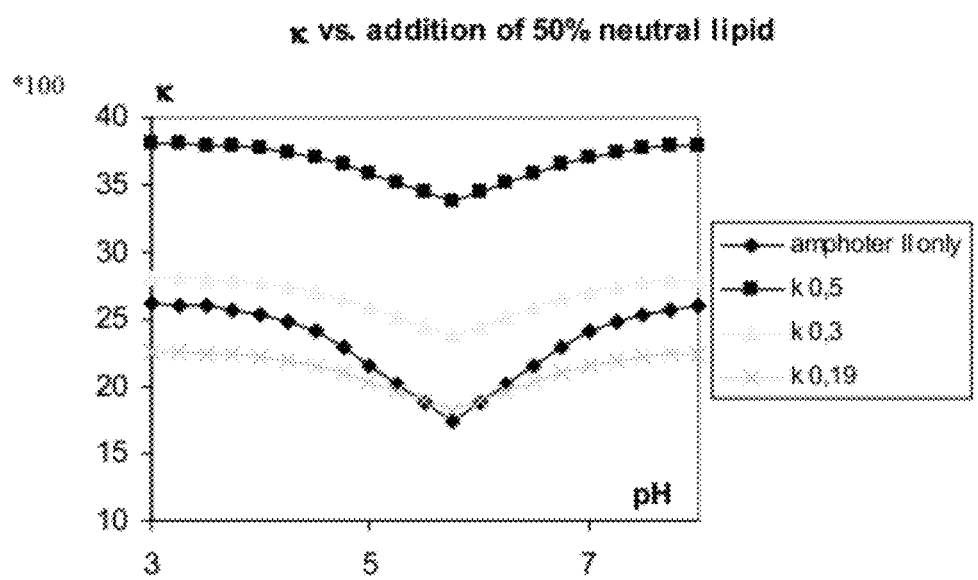
FIG. 9 is a graphical representation of the calculation for κ in response to external pH in amphoter II systems further comprising neutral lipids. 50% of neutral lipids were added to the system with the κ values given in the figure legend.

Section IV: Amphoteric Systems Further Comprising Neutral or Zwitterionic Lipids Neutral lipids comprise structures such as phosphatidylcholine, phosphatidyl ethanolamine, sphingolipids or cholesterol and the like. As these lipids do not have pH responsive elements that would react between pH 3 and 8, no changes in the molecular geometry occur in this range. Depending on the individual κ values of the neutral lipids, dilution of the bistable behaviour of the amphoteric lipid pair occurs and the steepness of d(κ)/d(pH) becomes smaller, as shown in FIG. 9. In addition, the curve in the phase diagram is shifted towards lower or higher values of κ, depending on the neutral lipid used for dilution of the charged lipids. The parameters used for the calculation of FIG. 9 are given in Table 29 below; volumes in Å$^3$.

TABLE 29

| | |
|---|---|
| Anion head volume | 70 |
| Anion tail volume | 400 |
| Anion pK | 5 |
| Cation head volume | 70 |
| Cation tail volume | 400 |
| Cation pK | 6.5 |
| Counterion+ volume | 70 |
| Counterion− volume | 70 |

FIG. 9 illustrates this behaviour for the addition of different neutral lipids with κ values of 0.5, 0.3 or 0.19, respectively, in combination with the amphoter II model system described above. The amplitude of the system is reduced from κ=0.089 to 0.044, while the minimum value follows the κ for the individual neutral components.

Thus, in some embodiments of the invention, 65 mol. % or less neutral lipids may be added to the salt forming charged lipids. More preferred are additions of 50 mol. % less and even more preferred are additions of 35 mol. % or less neutral lipid. The addition of neutral lipids may stabilise further the lipid bilayer, and preferred lipids for such purpose have higher κ values, e.g., κ>0.4 or even about 0.5. Typical examples of such lipids are the phosphatidylcholines with C14 to C18 alkyl chains in the hydrophobic region. As with most polar regions of lipids, the head-groups of phosphatidylcholines recruit counterions.

The addition of neutral lipids may also extend the zone of fusogenic behaviour and to this end neutral lipids with low values of κ may be employed. Such preferred lipids have κ values of 0.3 or less; more preferred lipids have κ values of about 0.2. Typical examples of such lipids are phosphatidylethanolamines. Phosphatidylethanolamines are assumed to form internal salt bridges (betaine structures) between the terminal amino group and the phosphate; therefore no counterions are recruited to the head-groups.

Phosphatidylethanolamines with C14 to C18 alkyl chains are preferred lipids to modulated the fusogenicity of the amphoteric liposomes.

Cholesterol is another example of a lipid having low κ and might therefore extend the fusogenic behaviour of an amphoteric lipid system.

It is of course possible to use mixtures of different neutral lipids to optimize the balance between fusogenicity and stability of such systems.

In practical terms, the presence of neutral lipids in the membrane of amphoteric liposomes has an effect on the fusogenicity of the liposomes and may, as predicted by the presented algorithm of the present invention, improve or impair the fusion of the liposomes. It is apparent from the algorithm, that the nature of such effect is largely dictated by the relation between k(salt) of the amphoteric system and k(neutral), the membrane constant of the neutral lipid or a mixture of neutral lipids. If, for example k(salt), is higher than k(neutral), then the addition of such neutral lipids may stimulate fusion or expand the width of the fusion zone. Of course, k(total) has to reach a certain minimum for this. In some embodiments, such minimum is smaller than 0.34 or 0.35, more preferred smaller than 0.3 and even more preferred such minimum is smaller than 0.25.

Figure 25:
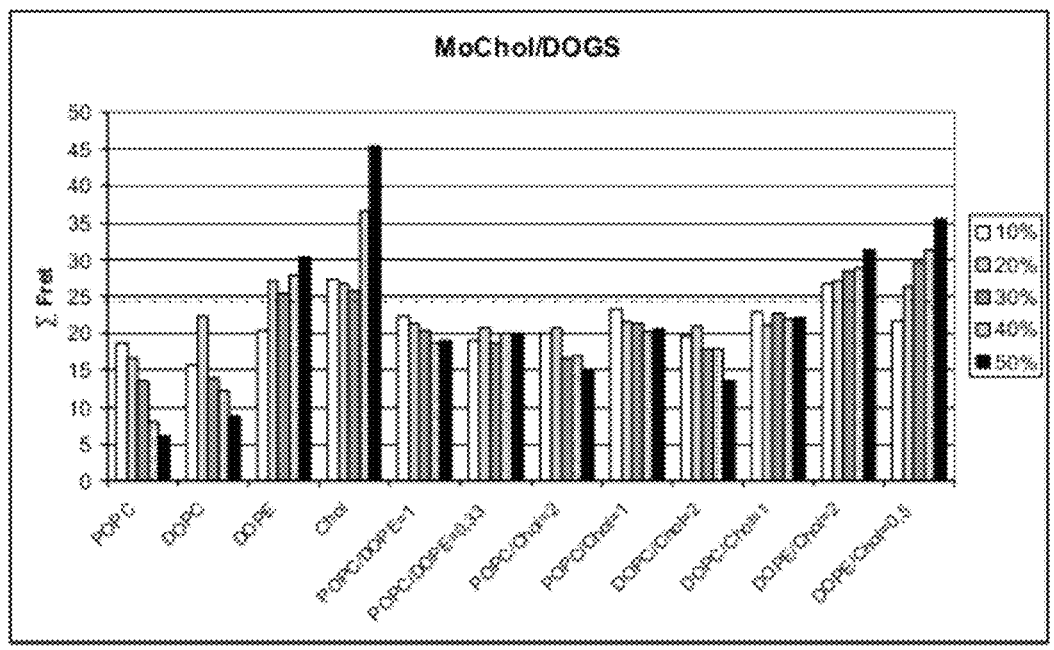
FIG. 25 shows the intensity of fusion (expressed as ΣFRET in the matrix C/A=0.33-3 vs. pH) of liposomes comprising MoChol/DOGS and 10%-50% of different neutral or zwitterionic lipids. The dotted line indicates the intensity of fusion of the liposomes with 0% neutral or zwitterionic lipid.

Experimental evidence is given in Example 15 and FIG. 25, where different neutral lipids in different amounts were mixed into the membrane of an amphoter II system (MoChol/DOGS). Furthermore, the influence of neutral lipids on the fusogenicity of other amphoteric systems was tested in Example 15.

Neutral lipids may also have impact on other characterisitcs of amphoteric liposomes, such as colloidal stability or stability in body fluids. For example, the use of amphoteric liposomes in pharmaceutical applications requires stability of the liposomes during storage and travelling through the bloodstream.

It becomes apparent that the presence of phosphatidylcholines as single neutral lipid in the membrane of amphoteric lipid mixtures lowers the fusability of amphoteric lipid mixtures. Phosphatidylcholines are zwitterionic lipids having high k values of >0.4.

In one embodiment of the invention less than 40 mol %, preferably less than 30 mol % and more preferably less than 20 mol % of neutral or zwitterionic lipids with k>0.4 as single neutral component are present in the amphoteric lipid mix. Such neutral or zwitterionic lipids include, but are not limited to, phosphatidylcholines, sphingomyelins or ceramides.

Cholesterol as neutral lipid has either no effect on the fusogenicity of amphoteric lipid systems or may even lead to an improvement in fusability. Similar behaviour was observed for the lipid DOPE. Cholesterol and phosphatidylethanolamines are neutral or zwitterionic lipids that have k values below 0.3 and adopt hexagonal phases.

In a further embodiment of the invention, cholesterol or phosphatidylethanolamines or a mix of both lipids may be present in the amphoteric lipid mix as single neutral or zwitterionic lipids. Preferably not more than 65 mol %, more preferably not more than 50 mol %, of these lipids is used as single neutral or zwitterionic lipids in the amphoteric liposomes. In other embodiments of the present invention, where cholesterol is essentially the only neutral lipid, cholesterol may comprise more than 80 mol % of the total neutral lipids of the amphoteric liposomes described herein. In another embodiment, cholesterol is the only neutral lipid in the amphoteric liposomes.

For optimising the balance between fusogenicity and stability it may be advantageous to use a mix of neutral or zwitterionic lipids as neutral component in the amphoteric liposomes.

In a still further embodiment of the invention a mixture of neutral lipids, such as phosphatidylcholines (PC), sphingomyelins or ceramides and phosphatidylethanolamines (PE) or a mixture of phosphatidylcholines (PC), sphingomyelins or ceramides and cholesterol (Chol) may be used as neutral components in the amphoteric liposomes. Preferably the ratio of PC/PE or PC/Chol is between 4 and 0.25, more preferably between 3 and 0.33. These neutral lipid mixes may be added to the salt-forming charged lipids in the amount 80 mol % or less, preferably 65 mol % or less. Most preferred are additions of 50 mol % or less.

It has also been found that neutral lipids may extend fusability to further C/A ratios as compared to mixture solely of charged amphiphiles. For example, the addition of 40 mol % POPC/DOPE=0.33 to a HisChol/DOGS mixture leads to an extension of the range of fusogenicity from C/A=>0-0.7 to C/A=>0-1. Similarly, the addition of 40 mol % cholesterol expands the C/A ratio of DOTAP/Chems for fusion to occur from C/A=>0-0.4 to C/A=>0-0.67.

In summary, the algorithm disclosed herein is suitable to describe phase transitions in amphoteric liposomes. Essential elements of the algorithm are (i) the lipid shape theory, (ii) the notion that counterions form part of the head-group volume and (iii) that lipid salt formation may occur in bilayers, leading to dissociation of the counterions. The simplicity of the algorithm makes it easy for the person skilled in the art to reproduce the calculations and adopt the system to the individual goals. It is possible to use other tools well-known to those skilled in the art than indicated to calculate molecular volumes. The qualitative prediction would not even change if molecular cross-sections were used instead of the volumes. Of course, one would have to re-calibrate the results in such a case.

As mentioned above, steric hindrance may interfere with salt formation in isolated cases. In such cases, the phase behaviour may differ substantially from what has been hereinbefore described. Most importantly, no dual stability at low and neutral pH is observed. Instead, a saddle of stability is observed for an intermediate pH with zones of instability to one or either side, depending on the type of amphoter system. Typical examples are included into the examples below.

The molecular volume calculations disclosed herein are silent on chain saturation in the hydrophobic parts. Use of unsaturated lipids may have specific advantages, since lipid membranes comprising such lipids have higher fluidity at ambient temperature which may improve fusion behaviour. It is also known that unsaturated lipids exert lateral pressure in the membrane, thus a correction factor can be inserted to reflect the apparent volume of these components. Such correction factor is higher than 1.

The algorithm of the present invention assumes the formation of lipid salts with a 1:1 stoichiometry between the two charged partners. It is possible to extend this concept to more complex situations, e.g., binding of multiple, monocharged lipids to a single other lipid with a plurality of charged groups. Binding of CHEMS, DOGS or oleic acid to amphiphilic derivatives of spermin may provide an example of this, but many other combinations exist. In another embodiment, the charged groups on the lipids might be more complex and comprise different charged groups, e.g., as in HistChol.

In such a case, 1:1 complexes might be formed with either other lipid anions or cations. Applying the concept of this invention to this example, counterion displacement can occur between the imidazolium cation and a separate lipid anion, e.g., CHEMS, DOGS or oleic acid anions; in addition, parallel counterion dissociation from the carboxyl of the histidine moiety may further support the formation of a hexagonal phase.

It will be apparent to those skilled in the art that such more complex arrangements of lipids put an extra burden on the steric compatibility of the interaction partners which may lead to lack of experimental success or mixed forms of possible interactions where not every possible binding site is engaged in salt formation.

The methods disclosed herein substantially reduce the number of variables involved with the optimisation of the system.

The present invention has been exemplified with various calculations in the detailed description. Further experimental work is described in the following examples. Examples are given with the understanding of further detailing certain aspects of practising the current invention. The examples by no means limit the scope of this disclosure.

EXAMPLES

Example 1

Preparation of Liposomes and pH-Dependent Fusion Experiment

Buffer System 100 mM sodium citrate and 200 mM sodium hydrogen phosphate were prepared as stock solutions and variable amounts of both solutions were mixed to adjust for the pH needed. CiP 7.0 as an example specifies a buffer from that series having a pH of 7.0 and is made from citrate and phosphate.

Liposome Production

Liposomes were formed from a dried lipid film. In brief, 20 µmol of the respective lipid composition was dissolved in 1 mL chloroform/methanol 3:1 and dried in vacuum using a rotary evaporator. The resulting film was hydrated for 45 min in 1 mL of CiP 8.0 with gentle agitation. The resulting liposome suspension was frozen, sonicated after thawing and eventually extruded through 200 nm polycarbonate filters.

pH-Jump Experiment

10 µl liposomes in CiP 8.0 were placed into a glass tube and mixed rapidly with 1 mL of CiP buffer of the pH needed. Samples were allowed to stand for 1 h at room temperature and 3 mL of 200 mM sodium hydrogen phosphate were rapidly mixed with the sample. Liposomes were analyzed for size using a MALVERN Zetasizer 3000HS and sizes were recorded as Z-average.

Example 2

Fusion of Amphoter I Lipid Mixtures

Figure 10:
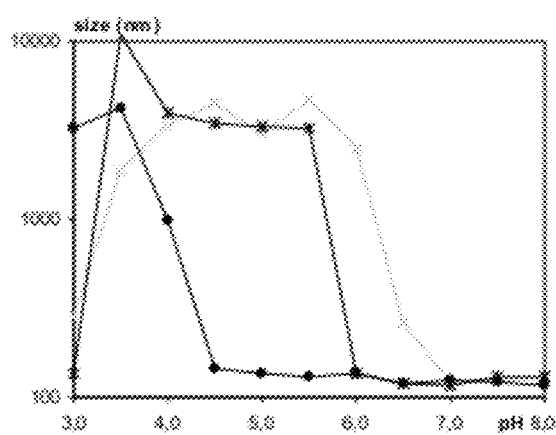
FIG. 10 shows the size of DOTAP/CHEMS liposomes after pH-jump in CiP buffer. DOTAP liposomes containing 66 mol. % CHEMS (crosses), 75 mol. % CHEMS (asterisks) or 100 mol. % CHEMS (dots) were produced at pH 8, jumped to the indicated pH and neutralized after one hour incubation at the lower pH. Size was measured at the end of the cycle.
Figure 11:
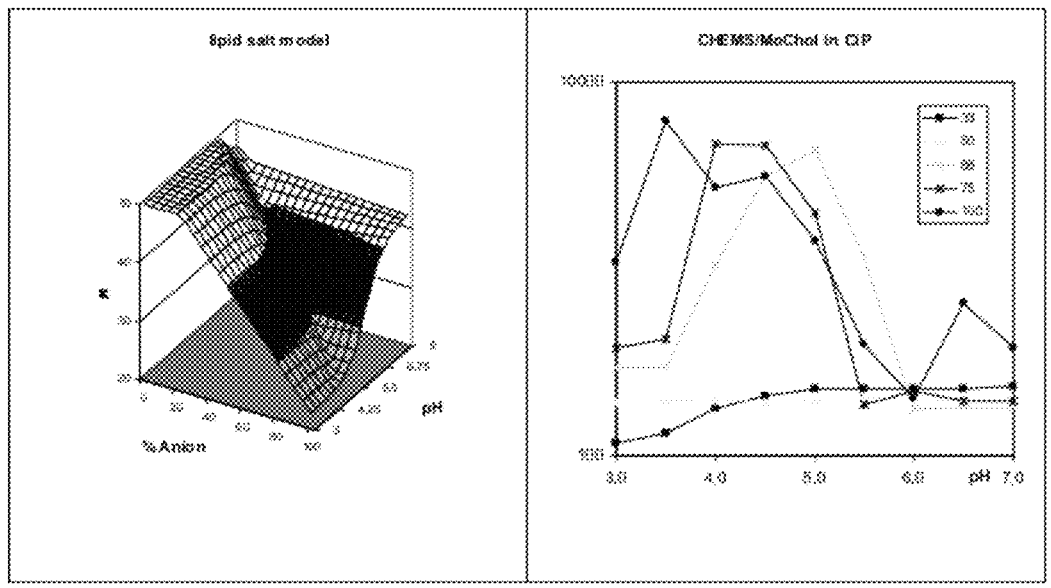
FIG. 11 shows the fusion behaviour of an amphoter II system comprising a MoCHol and CHEMS. Left—calculation of κ values for the system. Right—experimental fusion results after pH-jump of different mixtures of CHEMS and MoChol in CiP buffer. The percentage in the legend stands for the amount of CHEMS in the mixture.
Figure 12:
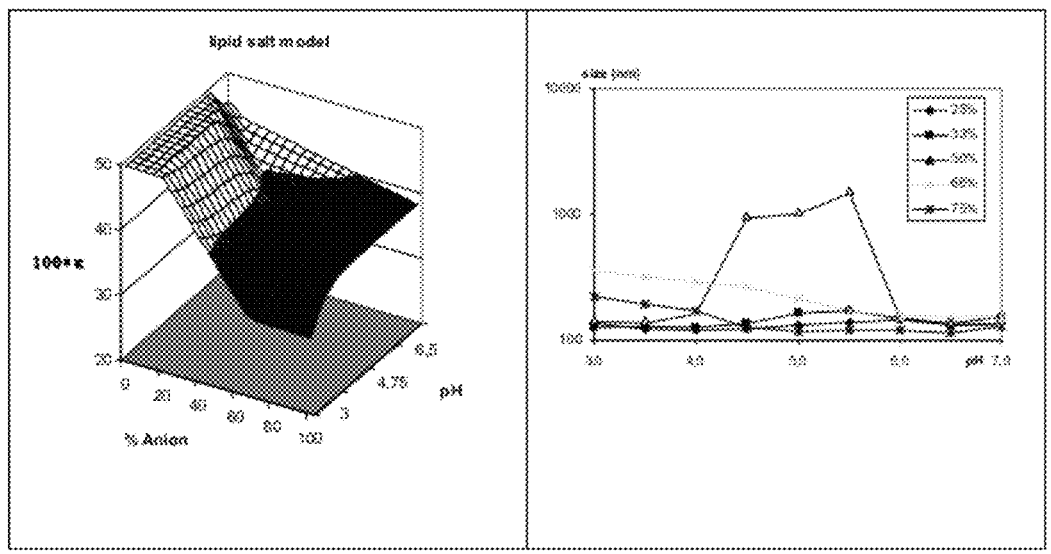
FIG. 12 shows the fusion behaviour of an amphoter III system comprising a MoCHol and DOPA. Left—calculation of κ values for the system. Right—experimental fusion results after pH-jump of different mixtures of DOPA and MoChol in CiP buffer. The percentage in the legend stands for the amount of DOPA in the mixture.

Liposomes were prepared from DOTAP and CHEMS in sodium citrate/sodium phosphate pH 8.0 (CiP 8.0) and small amounts were injected into a CiP buffer with a lower pH (see Example 1 for details). Any larger structures observed at the lower pH might be either due to aggregate formations and generation of multicentric honeycomb structures or such structures might result from genuine fusion. To separate between these two outcomes we readjusted the pH to neutrality using 200 mM sodium hydrogen phosphate. Electrostatic repulsion dissociates multicentric vesicles but not fusion products. The results are illustrated in FIG. 10.

As predicted in the mathematical salt bridge model, a valley of instability exists at slightly acidic conditions and fusion to larger particles was observed starting from pH 6.5. However, fast addition of the liposomes into low pH resulted in stabilisation of the particles as long as some DOTAP was present in the mixture. Liposomes from 100 mol. % CHEMS enter a fusogenic state below pH 4.5 and do not get stabilised at the lower pH.

Noteworthy, a 1:1 mixture of DOTAP/CHEMS cannot form liposomes in CiP 8.0 which is in good agreement with the mathematical model that predicts a non-lamellar phase for these parameters.

Example 3

Fusion of Amphoter II Systems

Liposomes were prepared from MoChol and CHEMS in sodium citrate/sodium phosphate pH 8.0 (CiP 8.0) and small amounts were injected into a CiP buffer with a lower pH (see Example 1 for details). Any larger structures observed at the lower pH might be either due to aggregate formations and generation of multicentric honeycomb structures or such structures might result from genuine fusion. To separate between these two outcomes we readjusted the pH to neutrality using 200 mM sodium hydrogen phosphate. Electrostatic repulsion dissociates multicentric vesicles but not fusion products.

Experimental evidence supports the salt bridge model. (See FIG. 11). The fusion zone is inclined towards high anion content due to the large head-group size of MoCHol Consequently, no fusion occurs with 33 mol. % or 50 mol. % CHEMS in the mixture, whereas mixtures containing 66 mol. % or 75 mol. % CHEMS undergo fusion when exposed to a pH between 4 and 6. As predicted, the onset of fusion is shifted to lower pH values with higher amounts of CHEMS. Again, 100 mol. % CHEMS is fusogenic with low pH but has no stable state at low pH.

The parameters used for the calculation are given in Table 30 below; CHEMS and MoChol in $Na/H_2PO_4$ were used as model compounds; all volumes in $Å^3$.

TABLE 30

| | |
|---|---|
| Anion head volume | 76 |
| Anion tail volume | 334 |
| Anion pK | 5.8 |
| Cation head volume | 166 |
| Cation tail volume | 371 |
| Cation pK | 6.5 |
| Counterion+ volume | 65 |
| Counterion− volume | 49 |

Example 4

Fusion in Amphoter III Systems with Steric Hindrance

Liposomes were prepared from POPG and MoChol in sodium citrate/sodium phosphate pH 8.0 (CiP 8.0) and small amounts were injected into a CiP buffer with a lower pH (see Example 1 for details). Any larger structures observed at the lower pH might be either due to aggregate formations and generation of multicentric honeycomb structures or such structures might result from genuine fusion. To separate between these two outcomes we readjusted the pH to neutrality using 200 mM sodium hydrogen phosphate. Electrostatic repulsion dissociates multicentric vesicles but not fusion products.

Experimental evidence supports only a situation where no salt bridge formation occurs. A mixture between MoChol and POPG does not undergo fusion in the pH-jump experiment (data not shown). This is quite possibly due to steric hindrance, as the protonated nitrogen in Mo-Chol is situated at the lower end of the morpholino ring and is therefore not easily accessible. In addition, the phosphate in POPG sits right at the lipid/water interface and is protected with a glycerol towards the water phase.

Example 5

Fusion in Amphoter III Systems, No Steric Hindrance

Amphoter III systems from POPG/MoChol do not undergo fusion (see Example 4 above). It was therefore questioned whether the removal of the protecting glycerol and exchange of POPG with DOPA would avoid such steric hindrance. In fact, such system undergoes fusion, as illustrated in the FIG. 12.

Details as per Example 1 above. The parameters used for the calculation are given in Table 31 below; DOPA and MoChol in $Na/H_2PO_4$ were used as model compounds, and volumes are expressed as $Å^3$.

TABLE 31

| | |
|---|---|
| Anion head volume | 63 |
| Anion tail volume | 501 |
| Anion pK | 3 |
| Cation head volume | 166 |
| Cation tail volume | 371 |
| Cation pK | 6.5 |
| Counterion+ volume | 65 |
| Counterion− volume | 49 |

The model calculation reflects the full complexity of the experimental fusion behaviour: no fusion for mixtures with less than 50% MoCHol, strong fusion for MoChol=DOPA and ongoing fusion with no stable phase under acidic conditions for mixtures with excess DOPA.

Example 6

Lipid Salt Formation with Monoalkyl Lipids

Figure 13:
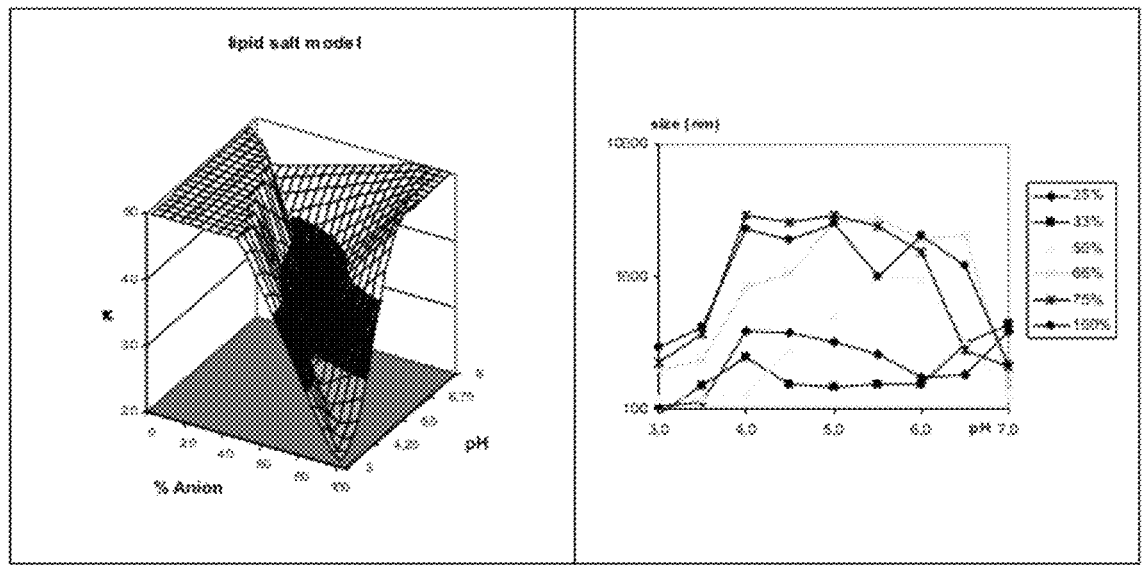
FIG. 13 shows the fusion behaviour of an amphoter II system comprising a monoalkyl lipid. Left—calculation of κ values for the system. Right—experimental fusion results after pH-jump of different mixtures of oleic acid and MoChol in CiP buffer. The percentage in the legend stands for the amount of oleic acid in the mixture.

Oleic acid was chosen as a known and popular pH-sensitive membrane component. As the lipid tail is relatively small in volume, any change in the head-group has more pronounced consequences for the membrane stability. As shown in FIG. 13, modelling predicts oleic acid to be a strong driver for fusion in an amphoter II system with MoChol. This is confirmed experimentally. Mixtures of oleic acid do form liposomes with Mo-Chol and particles rapidly undergo fusion when exposed to different conditions. As expected from the algorithm, the extent of fusion is limited for smaller amounts of OA in the mixture, but 50 mol. % of the anion results in the classic valley type fusion pattern. Since the fusion tendency is much stronger with OA, a bigger portion of that anion in the mix results in extensive fusion over a wide range of pH values. Still, mixtures can always be stabilised at low pH. Details as per Example 1.

TABLE 32

| | |
|---|---|
| MoChol head-group volume | 166 |
| MoChol tail volume | 371 |
| MoChol pK | 6.5 |
| Oleic acid head volume | 42 |
| Oleic acid tail volume | 208 |
| Oleic acid pK | 4.5 |
| Counterion citrate volume | 121 |
| Counterion sodium volume | 65 |

Example 7

Influence of Neutral Lipids

Figure 14:
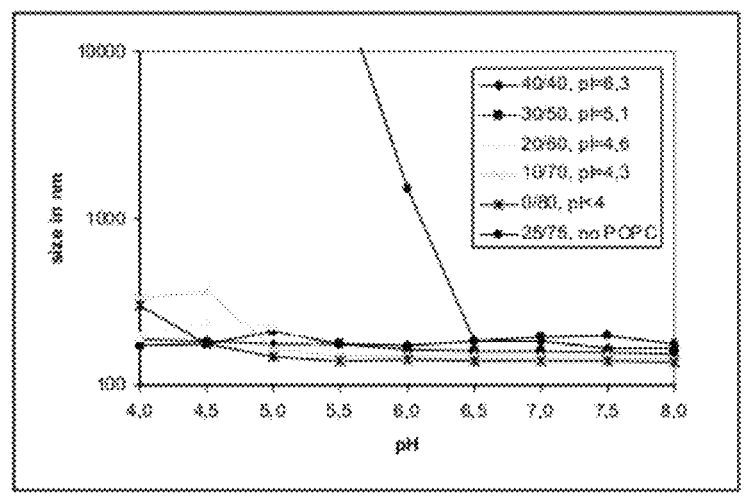
FIG. 14 illustrates fusion behaviour in the presence of POPC: Liposomes were produced at pH 7.5 and adjusted to acidic conditions to promote aggregation or fusion. Addition of 20 mol. % POPC greatly reduced the fusion tendency and liposomes were stable in size even at the lower pH. The composition in the legend represents the percentages for DOTAP and CHEMS; remainder is POPC. pI stands for the calculated isoelectric point of the mixture.

DOTAP and CHEMS were chosen as an amphoter I charged lipid pair and POPC ($κ{\sim}0.5$) was added as a neutral lipid. As expected, the pure mixture of the charged components undergoes aggregation or fusion at and below the isoelectric point. However, as shown in FIG. 14, the addition of only 20 mol. % POPC ameliorated such aggregation tendency to a great extent for all cation: anion ratios ranging from pure anion through to the 1:1 mixture that is no longer amphoteric.

Figure 15:
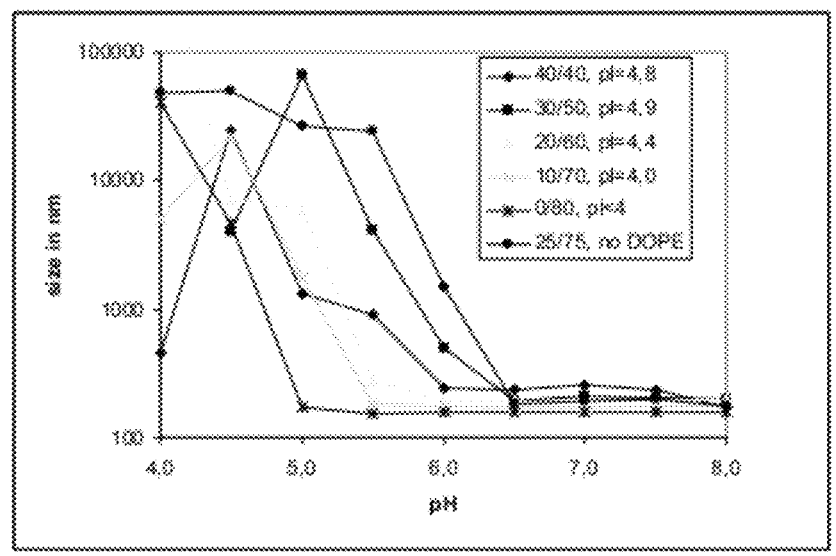
FIG. 15 illustrates fusion behaviour in the presence of DOPE: Liposomes were produced at pH 7.5 and adjusted to acidic conditions to promote aggregation or fusion. Addition of 20 mol. % DOPE maintains the fusion tendency of the amphoteric membrane. The composition in the legend represents the percentages for DOTAP and CHEMS; the remainder is DOPE. pI stands for the calculated isoelectric point of the mixture.

As shown in FIG. 15, the addition of the same amount of DOPE ($κ{\sim}0.19$) to the amphoter I mixture from DOTAP and CHEMS maintains the fusion behaviour independent of the ratio between DOTAP and CHEMS.

Example 8

Large Countercations can Reduce Fusion in Amphoter I Systems

In order to investigate the impact of different cations on the fusion behaviour of an amphoter I system, lipid films were prepared from 20 mol % DOTAP and 80 mol % CHEMS. A set of buffers was created starting from 20 mM citric acid and 40 mM phosphoric acid which were neutralized using KOH, NaOH, LiOH, Tris-(hydroxymethyl)aminomethane (TRIS, free base) or L-Arginine (free base).

Figure 16:
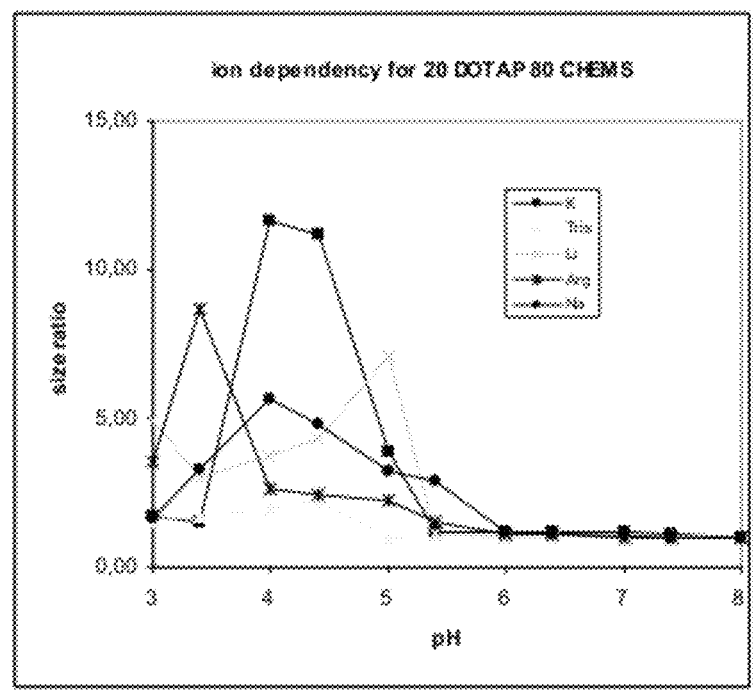
FIG. 16 shows the fusion behaviour of an amphoter I system comprising 20 mol % DOTAP and 80 mol % CHEMS in the presence of various countercations. The size ratio on the y-axis is used to normalize the liposome sizes to the value found at pH 8. All liposomes were within a 170 nm to 220 nm size range under these conditions.

The lipid films were hydrated at pH 8.0 and small amounts were injected into corresponding buffers with a lower pH (see Example 1 for details). After one hour incubation, the pH was readjusted to neutrality using the corresponding bases. The results are illustrated in FIG. 16.

As predicted in the model, fusion of liposomes from 20 mol % DOTAP and 80 mol % CHEMS can be observed around pH 4 to 5 as long as rather small countercations like potassium or sodium are used. Larger countercations like L-arginine or TRIS effectively stabilize the formulation and reduce or completely suppress fusion of the liposomes.

Example 9

Large Countercations can Reduce Fusion in Amphoter II Systems

In order to investigate the impact of different cations on the fusion behaviour of amphoter II systems, lipid films were prepared from 20 mol % MoCHOL and 80 mol % CHEMS. A set of buffers was created starting from 20 mM citric acid and 40 mM phosphoric acid which were neutralized using KOH, NaOH, LiOH, Tris-(hydroxymethyl)aminomethan (TRIS, free base) or L-Arginine (free base).

Figure 17:
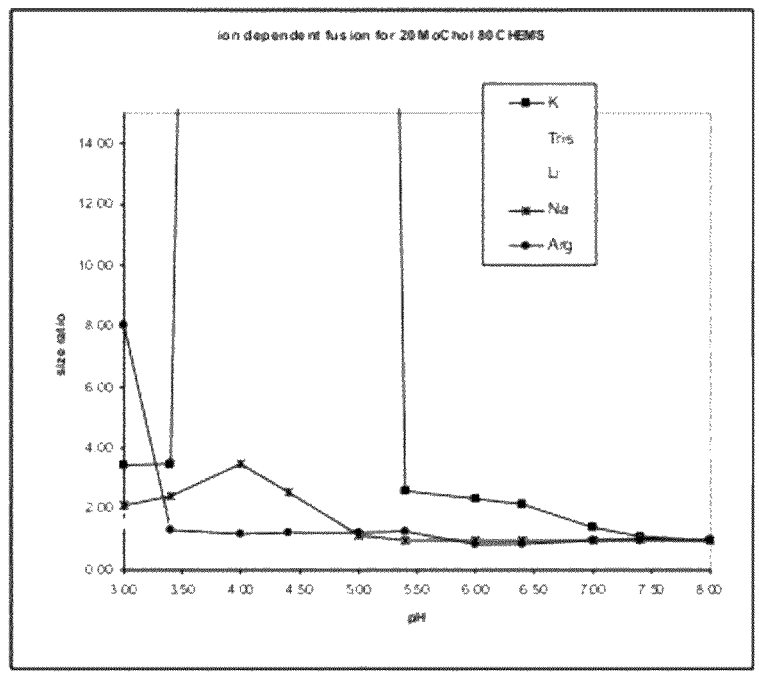
FIG. 17 shows the fusion behaviour of an amphoter II system comprising 20 mol % MoCHOL and 80 mol %, CHEMS in the presence of various countercations. The size ratio on the y-axis indicates liposome sizes after exposure to the pH values indicated on the x-axis and the values were normalized to a mock-treatment at pH 8. All liposomes sizes were between 140 and 300 nm under these conditions.

The lipid films were hydrated at pH 8.0 and small amounts were injected into corresponding buffers with a lower pH (see Example 1 for details). After one hour incubation, the pH was readjusted to neutrality using the corresponding bases. The results are illustrated in FIG. 17.

As predicted in the model, fusion of liposomes from 20 mol % MoChol and 80 mol % CHEMS can be observed between pH 3.5 to 4.5 as long as rather small countercations like potassium or sodium are used. Larger countercations like L-arginine or TRIS effectively stabilize the formulation and reduce or completely suppress fusion of the liposomes.

Example 10

Countercations have Little or No Effect on Fusion In Amphoter III Systems

In order to investigate the impact of different cations on the fusion behaviour of amphoter III systems, lipid films were prepared from 50 mol % MoCHOL and 50 mol % DOPA. A set of buffers was created starting from 20 mM citric acid and 40 mM phosphoric acid which were neutralized using KOH, NaOH, LiOH, Tris-(hydroxymethyl)aminomethan (TRIS, free base) or L-Arginine (free base).

Figure 18:
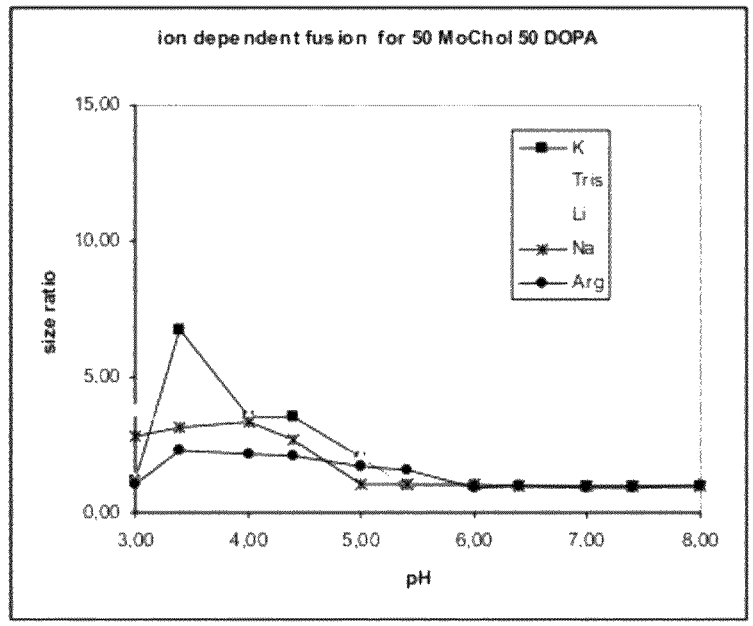
FIG. 18 shows the fusion behaviour of an amphoter III system comprising 50 mol % MoCHOL and 50 mol % DOPA in the presence of various countercations. The size ratio on the y-axis indicates liposome sizes after exposure to the pH values indicated on the x-axis and the values were normalized to a mock-treatment at pH 8. All liposomes sizes were between 220 and 260 nm under these conditions.

The lipid films were hydrated at pH 8.0 and small amounts were injected into corresponding buffers with a lower pH (see Example 1 for details). After one hour incubation, the pH was readjusted to neutrality using the corresponding bases. The results are illustrated in FIG. 18.

As predicted in the model, fusion of liposomes from 50 mol % MoChol and 50 mol % DOPA can be observed between pH 3.5 to 5 and there is little impact of the various cations on an amphoter III system. This is expected from the model, since MoCHOL and DOPA form a lipid salt at low pH conditions, thereby excluding countercations from the membrane. Consequently, once excluded from the lipid membrane, the countercations cannot contribute to membrane stability or instability.

Example 11

Fusion Assay Based on Fluorescence Resonance Energy Transfer (FRET)

To investigate the fusability of different amphoteric lipid mixtures a lipid mixing assay, based on FRET was used. Liposomes, single labelled with 0.6 mol % NBD-PE (N-(7-nitrobenz-2-oxa-1,3-diazol-4-yl)-1,2-dihexadecanoyl-sn-glycero-3-phosphoethanol-amine, triethylammonium salt) or Rhodamine-PE (Lissamine™ rhodamine B 1,2-dihexadecanoyl-sn-glycero-3-phosphoethanolamine, triethylammonium salt), respectively, were prepared to monitor lipid fusion through the appearance of a FRET signal.

Lipids were dissolved in isopropanol (final lipid concentration 16 mM) and mixed. Liposomes were produced by adding buffer (acetic acid 10 mM, phosphoric acid 10 mM, NaOH, pH 7.5) to the alcoholic lipid mix, resulting in a final lipid concentration of 1.95 mM and a final isopropanol concentration of 12.2%. For the preparation of the liposomes a liquid handling robot (Perkin Elmer, Multiprobe II Ex) was used. The NBD-labelled and Rh-labelled amphoteric liposomes were combined in a ratio 1:1 and subsequent diluted 1:1 with the buffer mentioned above. Finally small aliquots of this mixed sample were brought to decreasing specific pH (HAc 50 mM, Phosphoric acid 50 mM, NaOH, pH 7.5-2.5) and incubated at 37° C. for 2 h. Liposomes were diluted again 1:1 in this step.

Samples were measured for fluorescence using two sets of filters: NBD/Rhodamine:460/590 nm and NBD/NBD:460/530 nm. FRET as a signal for membrane fusion was expressed as the ratio of emission (590 nm)/emission (530 nm). A background of 0.4 indicates background fluorescence and was therefore subtracted from the FRET signals.

To discriminate between fusion and mere aggregation the suspension was neutralized to pH 7.5 and FRET signals were measured again. A possible interference of the remaining alcohol content of 3% on the fusion of the liposomes was excluded by pre-experiments.

Example 12

Fusion Assay of Amphoter I Lipid Mixtures Comprising Solely Charged Amphiphiles

Fusion assays were performed as described in Example 8. Lipid pairs as indicated in Table 33 were tested for fusion in cation/anion molar ratios (C/A ratio) of 0.17, 0.33, 0.40, 0.50, 0.67, 0.75 and pure anionic liposomes were prepared as controls.

Table 33 shows the lipid pairs tested in the experiment. For each lipid pair, the ranges of C/A ratios for which stability at pH 7 to pH 8 and fusion between pH 4 to pH 6 was observed are included in the table. In addition, for each lipid pair, the ranges of C/A ratios having a stable lamellar phase both at pH 7 to pH 8 and at pH 2 to pH 4 and fusion between pH 4 to pH 6 are shown.

The fusion can be expressed as Σ FRET, the sum of all measured FRET signals of the complete matrix C/A=0.17-0.75 vs. pH.

TABLE 33

| Cation | Anion | Σ FRET | Fusion Zone and stability at pH 8 to pH 7 C/A (molar ratio) | Fusion Zone and stablility at pH 8 to pH 7 and at pH 2 to pH 4 C/A (molar ratio) |
|---|---|---|---|---|
| DOTAP | CHEMS | 17 | >0-0.4 | ≧0.33-0.4 |
| DOTAP | Chol C3 | 20 | ≧0.5-0.67 | ≧0.5-0.67 |
| DOTAP | Chol C5 | 17 | >0-0.4 | ≧0.33-0.4 |
| DOTAP | Chol C6 | 12 | >0-0.17 | not stable at pH 2 to pH 4 |
| DOTAP | DMGS | 33 | >0-0.5 | ≧0.4-0.5 |
| DOTAP | DOGS | 17 | >0-0.4 | >0-0.4 |
| DOTAP | OA | ND | >0-0.33 | 0.17 |
| DOTAP | SA | ND | not stable at pH 7.5-6.5 | — |
| DC-Chol | Chems | 31 | >0-<1 | ≧0.4-<1 |
| DC-Chol | DMGS | 32 | >0-<1 | ≧0.5-<1 |
| DC-Chol | DOGS | 35 | >0-<1 | ≧0.33-<1 |
| TC-Chol | DMGS | 28 | >0-0.67 | ≧0.4-0.67 |
| DDAB | Chems | 6 | >0-0.17 | 0.17 |
| DDAB | DMGS | 35 | >0-0.5 | 0.5 |
| DODAP | DMGS | 42 | >0-<1 | ≧0.5-<1 |
| CTAB | DMGS | 29 | >0-0.5 | 0.5 |
| DOEPC | DMGS | 37 | >0-0.5 | ≧0.33-0.5 |
| Stearylamine | DOGS | ND | Not stable at pH 7.5-6.5 | — |
| N-methyl-PipChol | DMGS | 38 | >0-<1 | ≧0.5-<1 |

The following Tables 34 a-d show the fusion profiles for four selected amphoter I systems as matrix C/A vs. pH. In addition the fusion of liposomes of pure anionic lipid is shown (C/A=0). For example, it is known that liposomes of 100% Chems fuse at a pH of about 4.2 (Hafez et al, Biophys. J., 79, (2000), 1438-1446). This is confirmed by the present experiment. In addition the fusion profiles show the amphoter I mixtures having a stable lamellar phase both at pH 7 to pH 8 and at pH 2 to pH 4 and fuse between pH 4 to pH 6.

TABLES 34 A-D

DC-Chol/Chems → fusion over a broad range of C/A ratios

| | pH | | | | | |
|---|---|---|---|---|---|---|
| C/A | 7.50 | 6.50 | 5.50 | 4.50 | 3.50 | 2.50 |
| 0.00 | 0.01 | 0.01 | 0.05 | 0.47 | 1.54 | 1.63 |
| 0.17 | 0.00 | 0.00 | 0.14 | 2.61 | 3.65 | 1.23 |
| 0.33 | 0.00 | 0.00 | 0.91 | 2.87 | 1.06 | 0.75 |
| 0.40 | 0.00 | 0.00 | 1.80 | 2.89 | 0.88 | 0.62 |
| 0.50 | 0.00 | 0.00 | 2.27 | 2.26 | 0.58 | 0.36 |
| 0.67 | 0.00 | 0.00 | 2.07 | 0.63 | 0.24 | 0.14 |
| 0.75 | 0.00 | 0.00 | 1.84 | 0.18 | 0.07 | 0.03 |

DOTAP/Chol-C6 → fusion over a narrow range of C/A ratios

| | pH | | | | | |
|---|---|---|---|---|---|---|
| C/A | 7.5 | 6.5 | 5.5 | 4.5 | 3.5 | 2.5 |
| 0 | 0.00 | 0.00 | 0.08 | 0.85 | 2.27 | 2.98 |
| 0.17 | 0.00 | 0.00 | 1.64 | 2.61 | 1.02 | 0.63 |
| 0.33 | 0.00 | 0.00 | 0.94 | 0.81 | 0.25 | 0.21 |
| 0.4 | 0.00 | 0.00 | 0.55 | 0.38 | 0.16 | 0.12 |
| 0.5 | 0.00 | 0.15 | 0.37 | 0.04 | 0.00 | 0.01 |
| 0.67 | 0.00 | 0.34 | 0.20 | 0.00 | 0.00 | 0.00 |
| 0.75 | 0.00 | 0.47 | 0.01 | 0.00 | 0.00 | 0.00 |

DOTAP/DOGS → fusion range at C/A ratios >0-0.4

| | pH | | | | | |
|---|---|---|---|---|---|---|
| C/A | 7.5 | 6.5 | 5.5 | 4.5 | 3.5 | 2.5 |
| 0 | 0.05 | 0.08 | 0.32 | 0.81 | 1.63 | 1.44 |
| 0.17 | 0.00 | 0.00 | 0.70 | 4.08 | 0.80 | 0.17 |
| 0.33 | 0.00 | 0.03 | 1.38 | 1.98 | 0.20 | 0.06 |
| 0.4 | 0.00 | 0.05 | 1.35 | 1.28 | 0.14 | 0.04 |
| 0.5 | 0.08 | 0.21 | 0.73 | 0.27 | 0.00 | 0.00 |
| 0.67 | 0.02 | 0.05 | 0.04 | 0.00 | 0.00 | 0.00 |
| 0.75 | 0.09 | 0.25 | 0.28 | 0.01 | 0.00 | 0.00 |

DODAP/DMGS → fusion over a broad range of C/A ratios

| | pH | | | | | |
|---|---|---|---|---|---|---|
| C/A | 7.50 | 6.50 | 5.50 | 4.50 | 3.50 | 2.50 |
| 0 | 0.27 | 0.62 | 1.75 | 1.71 | 2.45 | 3.60 |
| 0.17 | 0.04 | 0.15 | 2.35 | 4.28 | 4.16 | 2.36 |
| 0.33 | 0.01 | 0.03 | 1.39 | 4.17 | 2.12 | 0.72 |
| 0.4 | 0.00 | 0.00 | 1.37 | 3.77 | 1.10 | 0.45 |
| 0.5 | 0.00 | 0.00 | 1.42 | 2.67 | 0.52 | 0.26 |
| 0.67 | 0.00 | 0.00 | 1.26 | 1.19 | 0.29 | 0.17 |
| 0.75 | 0.00 | 0.00 | 1.27 | 0.89 | 0.23 | 0.14 |

Example 13

Fusion Assay of Amphoter II Lipid Mixtures Comprising Solely Charged Amphiphiles A fusion assay was performed as described in Example 8. Lipid pairs as indicated in Table 35 were tested for fusion in cation/anion molar ratios (C/A ratio) of 0.33, 0.5, 0.67, 1, 1.5, 2, 3 and pure anionic liposomes were prepared as controls.

Table 35 shows the lipid pairs tested in the experiment. For each lipid pair the ranges of C/A ratios for which stability at pH 7 to pH 8 and fusion between pH 4 to pH 6 was observed are included in the table. In addition, for each lipid pair the ranges of C/A ratios having a stable lamellar phase both at pH 7 to pH 8 and at pH 2 to pH 4 and fuse between pH 4 to pH 6 are shown.

The fusion can be expressed as Σ FRET, the sum of all measured FRET signals in the matrix C/A=0.33-3 vs. pH.

TABLE 35

| Cation | Anion | Σ FRET | Fusion Zone and stability at pH 8 to pH 7 C/A (molar ratio) | Fusion Zone and stablility at pH 8 to pH 7 and at pH 2 to pH 4 C/A (molar ratio) |
|---|---|---|---|---|
| MoChol | Chems | 19 | >0-0.7 | ≥0.5-0.7 |
| MoChol | DOGS | 25 | >0-1 | ≥0.5-1 |
| MoChol | DMGS | 15 | >0-0.7 | ≥0.5-0.7 |
| MoChol | Chol-C3 | 17 | >0-0.7 | 0.7 |
| MoChol | Chol-C5 | 15 | >0-0.7 | ≥0.5-0.7 |
| MoChol | Chol-C6 | 11 | >0-0.5 | >0-0.5 |
| MoChol | Oleic acid | ND | not stable at pH 7.5-6.5 | — |
| DmC3Mo2 | Chems | 17 | >0-1 | ≥0.5-1 |
| DmC3Mo2 | DOGS | 26 | >0-1.5 | >0-1.5 |
| C4Mo4 | Chems | 14 | >0-0.5 | 0.5 |
| C4Mo4 | DOGS | 15 | >0-0.7 | >0-0.7 |
| DmC4Mo2 | Chems | 33 | >0 | ≥1 |
| DmC4Mo2 | DMGS | 28 | >0 | ≥1 |
| DmC4Mo2 | DOGS | 45 | >0 | ≥0.7 |
| DmC4Mo2 | Chol-C3 | 36 | ≥0.7 | ≥1.5 |
| DmC4Mo2 | Chol-C5 | 27 | >0-2 | ≥1-2 |
| DmC4Mo2 | Chol-C6 | 23 | >0-2 | ≥0.5-2 |
| C3Mo3 | Chems | 18 | >0-0.7 | ≥0.5-0.7 |
| C3Mo3 | DOGS | 16 | >0-0.7 | >0-0.7 |
| C3Mo2 | Chems | 23 | >0-1 | ≥0.7-1 |
| C3Mo2 | DOGS | 30 | >0-2 | ≥0.5-2 |
| C5Mo2 | Chems | 20 | >0-0.7 | 0.7 |
| C5Mo2 | DOGS | 22 | >0-1 | >0-1 |
| C6Mo2 | Chems | 21 | >0-1 | ≥0.7-1 |
| C6Mo2 | DOGS | 20 | >0-1 | >0-1 |
| C8Mo2 | Chems | 16 | >0-0.7 | ≥0.5-0.7 |
| C8Mo2 | DOGS | 23 | >0-1 | >0-1 |
| Chim | Chems | 30 | >0-1.5 | ≥0.5-1.5 |
| Chim | DMGS | 36 | >0-2 | ≥0.5-2 |
| Chim | DOGS | 30 | >0-1 | >0-1 |
| Chim | Oleic acid | ND | not stable at pH 7.5-6.5 | — |
| MoC3Chol | DOGS | 26 | >0-0.7 | 0.7 |
| DOIM | DOGS | 14 | >0-0.7 | >0-0.7 |
| HisChol | Chems | 22 | >0-0.7 | >0-0.7 |
| HisChol | DOGS | 37 | >0-0.7 | 0.7 |
| HisChol | OA | ND | not stable at pH 7.5-6.5 | — |

The following Tables 36 a-d show exemplary the matrix of the fusion profile for four selected amphoter II systems. In addition the fusion of liposomes of pure anionic lipid is shown (C/A=0). The fusion profiles indicate the amphoter II mixtures having a stable lamellar phase both at pH 7 to pH 8 and at pH 2 to pH 4 and fuse between pH 4 to pH 6.

TABLES 36 A-D

| | pH | | | | | |
|---|---|---|---|---|---|---|
| C/A | 7.5 | 6.5 | 5.5 | 4.5 | 3.5 | 2.5 |

DmC4Mo2/Chems → fusion over a broad range of C/A ratios

| 0.00 | 0.00 | 0.00 | 0.00 | 0.32 | 1.46 | 1.28 |
| 0.33 | 0.00 | 0.00 | 0.11 | 3.31 | 3.49 | 1.08 |

TABLES 36 A-D-continued

| C/A | pH 7.5 | 6.5 | 5.5 | 4.5 | 3.5 | 2.5 |
|---|---|---|---|---|---|---|
| 0.50 | 0.00 | 0.00 | 0.39 | 3.02 | 1.74 | 0.85 |
| 0.66 | 0.00 | 0.00 | 0.78 | 2.59 | 1.28 | 0.66 |
| 1.00 | 0.00 | 0.00 | 2.37 | 2.32 | 0.78 | 0.43 |
| 1.50 | 0.00 | 0.00 | 2.03 | 1.19 | 0.27 | 0.16 |
| 2.00 | 0.00 | 0.00 | 1.62 | 0.35 | 0.15 | 0.08 |
| 3.00 | 0.00 | 0.00 | 1.42 | 0.13 | 0.03 | 0.00 |

MoChol/Chol-C6 → fusion over a narrow range of C/A ratios

| 0.00 | 0.00 | 0.00 | 0.02 | 0.81 | 2.95 | 3.54 |
| 0.33 | 0.00 | 0.00 | 2.62 | 2.62 | 0.98 | 0.61 |
| 0.50 | 0.00 | 0.00 | 2.45 | 0.42 | 0.17 | 0.10 |
| 0.66 | 0.00 | 0.00 | 0.99 | 0.06 | 0.03 | 0.04 |
| 1.00 | 0.00 | 0.00 | 0.09 | 0.00 | 0.00 | 0.00 |
| 1.50 | 0.00 | 0.00 | 0.00 | 0.00 | 0.00 | 0.00 |
| 2.00 | 0.00 | 0.00 | 0.00 | 0.00 | 0.00 | 0.00 |
| 3.00 | 0.00 | 0.00 | 0.00 | 0.00 | 0.00 | 0.00 |

Chim/DMGS → fusion range at C/A ratios >0-2

| 0.00 | 0.33 | 0.55 | 2.00 | 2.16 | 2.03 | 1.99 |
| 0.33 | 0.05 | 0.10 | 1.50 | 4.53 | 2.20 | 0.83 |
| 0.50 | 0.00 | 0.04 | 4.19 | 4.13 | 0.67 | 0.38 |
| 0.66 | 0.00 | 0.03 | 3.52 | 2.25 | 0.42 | 0.30 |
| 1.00 | 0.00 | 0.02 | 3.15 | 0.45 | 0.25 | 0.21 |
| 1.50 | 0.00 | 0.29 | 2.12 | 0.18 | 0.13 | 0.09 |
| 2.00 | 0.00 | 0.80 | 1.28 | 0.07 | 0.05 | 0.04 |
| 3.00 | 0.01 | 1.68 | 0.32 | 0.00 | 0.00 | 0.00 |

C3Mo2/DOGS → fusion range at C/A ratios >0-2

| R C:A | pH 7.5 | 6.5 | 5.5 | 4.5 | 3.5 | 2.5 |
|---|---|---|---|---|---|---|
| 0.00 | 0.00 | 0.01 | 0.14 | 0.46 | 1.36 | 1.66 |
| 0.33 | 0.00 | 0.02 | 1.89 | 3.58 | 1.37 | 0.85 |
| 0.50 | 0.00 | 0.01 | 2.71 | 2.68 | 0.93 | 0.66 |
| 0.66 | 0.00 | 0.04 | 2.87 | 1.99 | 0.95 | 0.80 |
| 1.00 | 0.00 | 0.06 | 2.25 | 0.65 | 0.52 | 0.49 |
| 1.50 | 0.00 | 0.12 | 1.48 | 0.38 | 0.35 | 0.30 |
| 2.00 | 0.00 | 0.16 | 1.03 | 0.21 | 0.16 | 0.14 |
| 3.00 | 0.00 | 0.20 | 0.21 | 0.00 | 0.00 | 0.01 |

Example 14

Fusion Assay of Amphoter III Lipid Mixtures Comprising Solely Charged Amphiphiles Fusion assays were performed as described in Example 8. Lipid pairs as indicated in Table 37 were tested for fusion in cation/anion molar ratios (C/A ratio) of 1.5, 2, 3.

Table 37 shows the lipid pairs tested in the experiment. For each lipid pair the ranges of C/A ratios for which stability at pH 7 to pH 8 and fusion between pH 4 to pH 6 was observed are included in the table. In addition for each lipid pair the ranges of C/A ratios having a stable lamellar phase both at pH 7 to pH 8 and at pH 2 to pH 4 and fuse between pH 4 to pH 6 are shown.

TABLE 37

| Cation | Anion | Fusion Zone and stability at pH 8 to pH 7 C/A (molar ratio) | Fusion Zone and stablility at pH 8 to pH 7 and at pH 2 to pH 4 C/A (molar ratio) |
|---|---|---|---|
| MoChol | DOPA | >1-1.5 | >1-1.5 |
| HisChol | DOPA | >1-2 | 2 |
| MoChol | POPG | no fusion | no fusion |
| MoChol | Chol-SO4 | no fusion | no fusion |

The following Tables 37 a-d show by way of example the matrix of the fusion profile for the four tested amphoter III systems. In addition the fusion of liposomes of pure anionic lipid is shown (C/A=0). The fusion profiles indicate the amphoter III mixtures having a stable lamellar phase both at pH 7 to pH 8 and at pH 2 to pH 4 and fuse between pH 4 to pH 6. As described in Example 4 a mixture between MoChol and POPG does not undergo fusion owing to steric hindrance. This can be observed in the present FRET experiment as well. The same might be the case for the lipid pair MoChol/CholSO4.

TABLES 37 a-d

| C/A | pH 7.5 | 6.5 | 5.5 | 4.5 | 3.5 | 2.5 |
|---|---|---|---|---|---|---|
| MoChol/DOPA | | | | | | |
| 1.50 | 0.00 | 0.10 | 1.41 | 0.40 | 0.24 | 0.22 |
| 2.00 | 0.00 | 0.04 | 0.34 | 0.02 | 0.02 | 0.03 |
| 3.00 | 0.00 | 0.00 | 0.00 | 0.00 | 0.00 | 0.00 |
| HisChol/DOPA | | | | | | |
| 1.50 | 0.00 | 0.23 | 2.85 | 2.43 | 1.05 | 0.68 |
| 2.00 | 0.01 | 0.56 | 1.31 | 0.61 | 0.23 | 0.12 |
| 3.00 | 0.12 | 0.74 | 0.77 | 0.02 | 0.01 | 0.00 |
| MoChol/POPG | | | | | | |
| 1.50 | 0.13 | 0.16 | 0.31 | 0.34 | 0.50 | 0.46 |
| 2.00 | 0.00 | 0.03 | 0.12 | 0.10 | 0.13 | 0.11 |
| 3.00 | 0.00 | 0.00 | 0.00 | 0.00 | 0.00 | 0.01 |
| MoChol/Chol-SO4 | | | | | | |
| 1.50 | 0.00 | 0.00 | 0.04 | 0.02 | 0.02 | 0.01 |
| 2.00 | 0.00 | 0.00 | 0.00 | 0.00 | 0.00 | 0.00 |
| 3.00 | 0.00 | 0.00 | 0.00 | 0.00 | 0.00 | 0.00 |

Example 15

Impact of Neutral or Zwitterionic Lipids on the Fusion of Amphoteric Lipid Mixtures Amphoteric liposomes with increasing amounts of neutral or zwitterionic lipids were prepared as described in Example 8. Initially, an amphoter I system (DOTAP/DMGS) and an amphoter II (MoChol/DOGS) were prepared with the addition of 10-50% different neutral or zwitterionic lipids or mixtures thereof. Fusion was measured for a series of liposomes having different C/A ratios. Systems can be characterized using the sum of all such measurements in the entire matrix. The effect of the neutral or zwitterionic lipids was then analyzed using this global parameter (Σ FRET).

FIG. 25 shows the influence of different neutral or zwitterionic lipids on the fusogenicity of the amphoteric lipid mixture MoChol/DOGS. It is apparent that neutral lipids having a high κ, such as POPC or DOPC, decrease the fusogenicity of the amphoteric liposomes, whereas the lipids having a lower κ, such as DOPE or cholesterol, have little impact on the fusogenicity or may even improve the fusion. Mixtures of POPC and DOPE and mixtures of POPC or DOPC and cholesterol may have little impact or decrease the fusion ability, depending of the ratio of the two lipids. The presence of DOPE and cholesterol in the membrane of the amphoteric liposomes does not change the fusogenicity or even leads to an increase of it. These findings correlate very well with the model as shown in FIGS. 21-24 for the neutral lipids POPC, DOPE, Cholesterol and mixtures of POPC/Chol=1. In the figures Σ FRET of liposomes from DOTAP/DMGS (C/A=0.17-0.75) or MoCHol/DOGS (C/A 0.33-3) was plotted against k(min) for mixtures with 0%-50% neutral lipid. The reference K(min) was modelled for C/A=0.66 (DOTAP/DMGS) or C/A=1 (MoChol/DOGS).

In a further experiment the effect of different neutral or zwitterionic lipid systems (POPC, cholesterol or POPC/DOPE=0.33) on the fusogenicity of other amphoteric lipid systems were determined. Tables 38 and 39 summarize these data and confirm the results of the first part of the experiment. Tables 38 and 39 show the Σ Fret and range of C/A ratios for which the amphoteric liposomes are stable at pH 7 to pH 8 and fuse between pH 3 to pH 6, preferably between pH 4 to pH 6.

It becomes apparent that amphoteric lipid systems having low fusogenicity can be clearly improved by the addition of neutral or zwitterionic lipids. Furthermore the results indicate that neutral or zwitterionic lipids may have also an impact on the range of fusogenicity. This means that the range of C/A ratios can be broadened or narrowed depending on the neutral or zwitterionic lipid used in the mixtures.

TABLE 38

| Cation | Anion | K(salt) | Σ Fret 0% neutral lipid C/A ratio | Σ Fret 20% POPC C/A ratio | Σ Fret 40% POPC C/A ratio | Σ Fret 20% Chol C/A ratio | Σ Fret 40% Chol C/A ratio | Σ Fret 40% POPC/DOPE 0.33 C/A ratio | Σ Fret 40% POPC/DOPE 0.33 C/A ratio |
|---|---|---|---|---|---|---|---|---|---|
| DODAP | DMGS | 0.157 | 42 | 31 | 21 | 40 | 42 | 30 | 29 |
| DODAP | DMGS | | >0-<1 | >0-<1 | >0- | >0-<1 | >0-<1 | >0-0.67 | >0-<1 |
| N-methyl-PipChol | DMGS | 0.271 | 38 | 16 | 3 | 40 | 44 | 40 | 31 |
| N-methyl-PipChol | DMGS | | >0-<1 | >0-0.5 | — | >0-<1 | >0-<1 | >0-<1 | >0-<1 |
| DDAB | DMGS | 0.182 | 35 | 7 | 4 | 16 | 21 | 27 | 30 |
| DDAB | DMGS | | >0-0.5 | >0- | — | >0- | >0- | >0-0.67 | >0-0.67 |
| DOEPC | DMGS | 0.269 | 37 | ND | ND | ND | ND | 26 | 23 |
| DOEPC | DMGS | | >0-0.5 | ND | ND | ND | ND | >0-0.67 | >0-0.67 |
| DC-Chol | DOGS | 0.225 | 35 | 20 | 10 | 25 | 24 | 28 | 39 |
| DC-Chol | DOGS | | >0-<1 | >0- | >0- | >0- | >0-<1 | >0-<1 | >0-<1 |
| DOTAP | DMGS | 0.169 | 33 | 28 | 24 | 31 | 32 | 30 | 33 |
| DOTAP | DMGS | | >0-0.5 | >0- | >0- | >0- | >0- | >0-0.67 | >0-0.67 |
| DC-Chol | DMGS | 0.254 | 32 | 22 | 13 | 35 | 42 | 36 | 29 |
| DC-Chol | DMGS | | >0-<1 | >0- | >0- | >0-<1 | >0-<1 | >0-<1 | >0-<1 |
| DC-Chol | Chems | 0.265 | 31 | 8 | 1 | 33 | 33 | 25 | 19 |
| DC-Chol | Chems | | >0-<1 | >0- | — | >0-<1 | >0-<1 | >0-<1 | >0-0.67 |
| CTAB | DMGS | 0.271 | 29 | ND | ND | ND | ND | 24 | 16 |
| CTAB | DMGS | | >0-0.5 | ND | ND | ND | ND | >0-0.5 | >0-0.5 |
| TC-Chol | DMGS | 0.271 | 28 | ND | ND | ND | ND | 33 | 28 |
| TC-Chol | DMGS | | >0-0.67 | ND | ND | ND | ND | >0-<1 | >0-<1 |
| DOTAP | Chol- | 0.156 | 20 | ND | ND | ND | ND | 25 | 29 |
| DOTAP | Chol- | | ≥0.5-0.67 | ND | ND | ND | ND | ≥0.33-<1 | >0-<1 |
| DOTAP | Chol- | 0.186 | 17 | ND | ND | ND | ND | 17 | 17 |
| DOTAP | Chol- | | >0-0.4 | ND | ND | ND | ND | >0-0.4 | >0-0.4 |
| DOTAP | Chems | 0.171 | 17 | 11 | 3 | 21 | 25 | 19 | 25 |
| DOTAP | Chems | | >0-0.4 | >0- | >0- | >0- | >0- | >0-0.4 | >0-0.67 |
| DOTAP | DOGS | 0.153 | 17 | 17 | 17 | 36 | 37 | ND | ND |
| DOTAP | DOGS | | >0-0.4 | >0- | >0- | >0- | >0- | ND | ND |
| DOTAP | Chol- | 0.202 | 12 | ND | ND | ND | ND | 13 | 16 |
| DOTAP | Chol- | | >0-0.17 | ND | ND | ND | ND | >0-0.17 | >0-0.4 |
| DDAB | Chems | 0.186 | 6 | 7 | 0 | 33 | 52 | 10 | 9 |
| DDAB | Chems | | >0-0.17 | >0- | — | >0- | >0-<1 | >0-0.33 | >0-0.4 |

TABLE 39

| Cation | Anion | K(salt) | Σ Fret 0% neutral lipid C/A ratio | Σ Fret 20% POPC C/A ratio | Σ Fret 40% POPC C/A ratio | Σ Fret 20% Chol C/A ratio | Σ Fret 40% Chol C/A ratio | Σ Fret 40% POPC/DOPE 0.33 C/A ratio | Σ Fret 40% POPC/DOPE 0.33 C/A ratio |
|---|---|---|---|---|---|---|---|---|---|
| DmC4Mo2 | DOGS | 0.336 | 45 | ND | ND | ND | ND | 35 | 36 |
| DmC4Mo2 | DOGS | | >0 | ND | ND | ND | ND | >0 | >0 |
| Chim | DOPS | 0.284 | 39 | ND | ND | ND | ND | 31 | 33 |
| Chim | DOPS | | ≥1-2 | ND | ND | ND | ND | ≥1-1.5 | ≥1-1.5 |
| HisChol | DOGS | 0.282 | 37 | 19 | 9 | 33 | 50 | 34 | 29 |
| HisChol | DOGS | | >0-0.7 | >0- | >0- | >0- | <0- | >0-0.7 | <0-1 |
| Chim | DMGS | 0.278 | 36 | 12 | 5 | 37 | 42 | 26 | 23 |
| Chim | DMGS | | >0-2 | >0- | >0- | >0- | >0-1 | >0-1 | >0-1 |
| DmC4Mo2 | Chol- | 0.385 | 36 | ND | ND | ND | ND | 21 | 18 |
| DmC4Mo2 | Chol- | | ≥0.7 | ND | ND | ND | ND | ≥0.5 | >0 |
| DmC4Mo2 | Chems | 0.403 | 33 | 10 | 0 | 32 | 23 | 23 | 20 |
| DmC4Mo2 | Chems | | >0 | >0- | — | >0 | ≥1 | >0-2 | >0-2 |
| Chim | Chems | 0.292 | 30 | ND | 0 | 33 | 27 | 15 | 12 |
| Chim | Chems | | >0-1.5 | ND | — | >0- | >0- | >0-1.0 | >0-0.7 |
| Chim | DOGS | 0.247 | 30 | 16 | 14 | 29 | 29 | 24 | 22 |
| Chim | DOGS | | >0-1 | >0- | >0- | >0-1 | >0- | >0-1 | >0-1 |

TABLE 39-continued

| Cation | Anion | K(salt) | Σ Fret 0% neutral lipid C/A ratio | Σ Fret 20% POPC C/A ratio | Σ Fret 40% POPC C/A ratio | Σ Fret 20% Chol C/A ratio | Σ Fret 40% Chol C/A ratio | Σ Fret 40% POPC/DOPE 0.33 C/A ratio | Σ Fret 40% POPC/DOPE 0.33 C/A ratio |
|---|---|---|---|---|---|---|---|---|---|
| C3Mo2 | DOGS | 0.288 | 30 | ND | ND | ND | ND | 28 | 24 |
| C3Mo2 | DOGS | | >0-2 | ND | ND | ND | ND | >0-1.5 | >0-1 |
| DmC4Mo2 | DMGS | 0.378 | 28 | 22 | 9 | 33 | 41 | 36 | 38 |
| DmC4Mo2 | DMGS | | >0 | >0-0.7 | >0- | >0 | >0 | >0-2 | >0 |
| DmC4Mo2 | Chol- | 0.423 | 27 | ND | ND | ND | ND | 19 | 17 |
| DmC4Mo2 | Chol- | | >0-2 | ND | ND | ND | ND | >0-2 | >0-1.5 |
| DmC3Mo2 | DOGS | 0.319 | 26 | ND | ND | ND | ND | 20 | 19 |
| DmC3Mo2 | DOGS | | >0-1.5 | ND | ND | ND | ND | >0-1 | >0-1 |
| MoC3Chol | DOGS | 0.269 | 26 | 15 | 9 | 30 | 34 | 21 | 19 |
| MoC3Chol | DOGS | | >0-0.7 | >0- | >0- | >0- | >0- | >0-0.7 | >0-0.7 |
| MoChol | DOGS | 0.303 | 25 | 17 | 11 | 24 | ND | 21 | 20 |
| MoChol | DOGS | | >0-1 | >0- | >0- | >0-1 | ND | >0-1 | >0-1 |
| DmC4Mo2 | Chol- | 0.442 | 23 | ND | ND | ND | ND | 17 | 14 |
| DmC4Mo2 | Chol- | | >0-2 | ND | ND | ND | ND | >0-1.5 | >0-1 |
| C3Mo2 | Chems | 0.344 | 23 | ND | ND | ND | ND | 13 | 9 |
| C3Mo2 | Chems | | >0-1 | ND | ND | ND | ND | >0-0.7 | >0-0.7 |
| C8Mo2 | DOGS | 0.365 | 23 | ND | ND | ND | ND | 19 | 24 |
| C8Mo2 | DOGS | | >0-1 | ND | ND | ND | ND | >0-1 | >0-1 |
| HisChol | Chems | 0.336 | 22 | 9 | 1 | 22 | 25 | 18 | 16 |
| HisChol | Chems | | >0-0.7 | >0- | — | >0-1 | >0- | >0-1 | >0-0.7 |
| C5Mo2 | DOGS | 0.318 | 22 | ND | ND | ND | ND | 23 | 18 |
| C5Mo2 | DOGS | | >0-1 | ND | ND | ND | ND | >0-1 | >0-1 |
| MoChol | DOPS | 0.340 | 21 | ND | ND | ND | ND | 22 | 21 |
| MoChol | DOPS | | 1 | ND | ND | ND | ND | 1 | 1 |
| C6Mo2 | Chems | 0.401 | 21 | ND | ND | ND | ND | 12 | 8 |
| C6Mo2 | Chems | | >0-1 | ND | ND | ND | ND | >0-0.7 | >0-0.7 |
| C5Mo2 | Chems | 0.382 | 20 | ND | ND | ND | ND | 11 | 8 |
| C5Mo2 | Chems | | >0-0.7 | ND | ND | ND | ND | >0-0.7 | >0-0.7 |
| C6Mo2 | DOGS | 0.334 | 20 | ND | ND | ND | ND | 19 | 19 |
| C6Mo2 | DOGS | | >0-1 | ND | ND | ND | ND | >0-1 | >0-1 |
| MoChol | Chems | 0.363 | 19 | 3 | 0 | 20 | 24 | 13 | 10 |
| MoChol | Chems | | >0-0.7 | >0- | — | >0-1 | >0-1 | >0-0.7 | >0-0.7 |
| MoChol | DMPS | 0.383 | 19 | ND | ND | ND | ND | 11 | 13 |
| MoChol | DMPS | | 1 | ND | ND | ND | ND | — | — |
| C3Mo3 | Chems | 0.363 | 18 | ND | ND | ND | ND | 10 | 8 |
| C3Mo3 | Chems | | >0-0.7 | ND | ND | ND | ND | >0-0.7 | >0-0.5 |
| DmC3Mo2 | Chems | 0.382 | 17 | ND | ND | ND | ND | 10 | 9 |
| DmC3Mo2 | Chems | | >0-1 | ND | ND | ND | ND | >0-0.7 | >0-0.7 |
| MoChol | Chol- | 0.345 | 17 | ND | ND | ND | ND | 13 | 9 |
| MoChol | Chol- | | >0-0.7 | ND | ND | ND | ND | >0-0.7 | >0-0.7 |
| C8Mo2 | Chems | 0.440 | 16 | ND | ND | ND | ND | 10 | 8 |
| C8Mo2 | Chems | | >0-0.7 | ND | ND | ND | ND | >0-0.33 | >0-0.7 |
| C3Mo3 | DOGS | 0.304 | 16 | ND | ND | ND | ND | 21 | 17 |
| C3Mo3 | DOGS | | >0-0.7 | ND | ND | ND | ND | >0-1 | >0-1 |
| C4Mo4 | DOGS | 0.334 | 15 | ND | ND | ND | ND | 14 | 13 |
| C4Mo4 | DOGS | | >0-0.7 | ND | ND | ND | ND | >0-0.7 | >0-0.7 |
| MoChol | Chol- | 0.382 | 15 | ND | ND | ND | ND | 7 | 6 |
| MoChol | Chol- | | >0-0.7 | ND | ND | ND | ND | >0-0.7 | >0-0.5 |
| MoChol | DMGS | 0.342 | 15 | 8 | 4 | 18 | 23 | 15 | 14 |
| MoChol | DMGS | | >0-0.7 | >0- | — | >0-1 | >0-1 | >0-0.7 | >0-0.7 |
| C4Mo4 | Chems | 0.401 | 14 | ND | ND | ND | ND | 6 | 4 |
| C4Mo4 | Chems | | >0-0.5 | ND | ND | ND | ND | >0-0.5 | >0-0.3 |
| DOIM | DOGS | 0.145 | 14 | 9 | 10 | 13 | 26 | 15 | 13 |
| DOIM | DOGS | | >0-0.7 | >0- | >0- | >0- | >0- | >0-0.7 | >0-0.7 |
| MoChol | Chol- | 0.401 | 11 | ND | ND | ND | ND | 6 | 5 |
| MoChol | Chol- | | >0-0.5 | ND | ND | ND | ND | >0-0.5 | >0-0.5 |

Example 16

Synthesis of Cationic Amphiphiles

Synthesis of DmC4Mo2

A. Synthesis of 2,3-Dimethylsuccinic-anhydride 2,3-Dimethyl succinic anhydride was prepared as described in Sutton, et al. OPPI 24 (1992) 39. Briefly, 7.1 g 2,3-dimethyl succinic acid and 6.9 ml acetanhydride were slowly heated up to 50° C. for 3 hours. Then acetanhydride was removed by distillation. The product was recrystallized from ethanol abs. and characterized by the melting point.

B. Synthesis of 2,3-Dimethylsuccinicacid-monocholesterylester 2,3-Dimethylsuccinic acid-monocholesterylester was prepared according to the Chems synthesis in J. T. Kley et al., Monatshefte Chem 129 (1998) 319. 2.9 g 2,3-dimethylsuccinic-anhydride, 6.3 ml triethylamine, 0.06 g dimethylaminopyridine and 50 ml chloroform were combined in a round-bottomed flask and refluxed. 7.8 g cholesterol was added to the mixture in two steps during 45 min. The mixture was refluxed for 6 days. Finally the solvent was evaporated and 100 ml toluol and 1.8 g pyridine were added. The mixture was refluxed again for 1.5 days. The solvent was removed at a rotovap and the crude product was first purified by column chromatography on silica gel (eluent: dichloromethane/methanol 96:4) followed by a recrystallization from ether and a second column chromatography on silica gel (eluent: acetic acid ethyl ester: petrol ether 1:1). Purity of the product was judged by thin layer chromatography.

Synthesis of DmC4Mo2

5.9 g 2,3-Dimethylsuccinic acid-monocholesterylester and 300 ml tetrahydrofurane were stirred under $N_2$ atmosphere and cooled down to −10° C. 1.9 ml N-methylmorpholine was added to the mixture. Then 1.6 ml isobutylchloroformiate was added dropwise to the mixture. After on hour the mixture was brought to 0° C. and about 2 hours later to room temperature. Then the mixture was again cooled down to −10° C., 1.5 ml 4-(2-Aminoethyl)morpholine was added dropwise and the reaction was allowed to stir overnight at room temperature. The mixture was filtered, then the solvent was evaporated and the product was purified by column chromatography on silica gel (eluent: dichloromethane/methanol 96:4) and recrystallization from hexane. The product was characterized by thin layer chromatography, $^1$H-NMR and HPLC.

Synthesis of DmC3Mo2

A. Synthesis of 2,2-Dimethyl-malonic Acid Monoethyl Ester 25 g 2,2-Dimethyl-malonic acid diethyl ester, 7.8 g potassium hydroxide and 500 ml ethanol were mixed in a round-bottomed flask and refluxed for 3 hours. Then again 2.2 g potassium hydroxide were added and the mixture was refluxed overnight. The solvent was removed on a rotovap, 250 ml $H_2O$ were added and the mixture was washed with ether. The aqueous phase was acidified with HCl to pH 3-4 followed by two extractions with dichloromethane. The organic solvent was dried and evaporated and the resulting product was characterized by $^1$H-NMR.

B. Synthesis of 2,2-Dimethyl-N-(2-morpholin-4-yl-ethyl)-malonamic Acid Ethyl Ester 19 g 2,2-Dimethyl-malonic acid monoethyl ester were weighed into a round-bottomed flask and under $N_2$ atmosphere and room temperature, 200 ml tetrahydrofurane, 15.6 ml 4-(2-Aminoethyl)-morpholine and 32.6 ml N-Methylmorpholine were added. The reaction was stirred and cooled down to 5° C. Then, 43.8 g TBTU were added and the mixture was allowed to stir for another 1.5 hours. Finally the solvent was removed and the residue dissolved in 400 ml dichloromethane. This organic phase was washed two times with 500 ml $NaHCO_3$ solution. The dichloromethane phase was dried then the solvent was evaporated. Purity of the product was judged by gas chromatography.

C. Synthesis of 2,2-Dimethyl-N-(2-morpholin-4-yl-ethyl)-malonamic Acid (HCl Salt)

34.1 g 2,2-Dimethyl-N-(2-morpholin-4-yl-ethyl)-malonamic acid ethyl ester, 8.4 g potassium hydroxide, 200 ml ethanol and 4.5 ml $H_2O$ were stirred at 80° C. for 6 hours. Then most of the solvent was removed and the pH was adjusted to pH 3-4 with about 100 ml 2N HCl. The solvent was evaporated and toluol was added and then removed. To the final residue methanol was added and the suspension was filtered to remove salts. The solvent was removed and the residue was dissolved in $H_2O$ and lyophilized. The product was characterized by $^1$H-NMR.

C. Synthesis of DmC3Mo2

10.7 g 2,2-Dimethyl-N-(2-morpholin-4-yl-ethyl)-malonamic acid (HCl salt) and 50 ml toluol were combined in a round-bottomed flask under $N_2$ atmosphere. Then 13.9 ml thionyl chloride were added and the solution was refluxed for 3 hours. The solvent was evaporated and 150 ml chloroform were added to the residue. After the addition of 14.7 g cholesterol and 0.023 g 4-Dimethylaminopyridine the mixture was stirred at room temperature and 15 min later 10.7 ml triethylamine were added. The reaction was allowed to stir at room temperature for 1.5 days. Then the solvent was removed at a rotovap and the crude product was dissolved in 100 ml acetic acid ethyl ester and subsequent purified by column chromatography on silica gel (eluent: acetic acid ethyl ester/methanol 9:1) and recrystallization from ether. The final product was characterized by $^1$H-NMR and HPLC.

Synthesis of C3Mo3

A. Synthesis of Malonic Acid Monochloride

Malonic acid monochloride was synthesized as described in Wilson, et al., J. Org. Chem. 39 (1974) 3170. Briefly, 150 g malonic acid and 600 ml ether were added under $N_2$ atmosphere in a round bottom flask. The mixture was stirred and 150.2 ml thionyl chloride were added dropwise. The suspension was refluxed for 5 hours before the solvent was removed at a rotovap. The residue was treated three times under sonication and 40° C. with 500 ml chloroform:hexane 1:2. The three extracts were combined and kept at −15° C. over night. The mother liquor was decanted and the yellow crystals were washed with hexane and dried. The mother liquor was concentrated and again kept at −15° C. resulting in further product.

B. Synthesis of Malonic Acid Mono Cholesteryl Ester 26 g cholesterol and 12.4 g malonic acid monochloride were weighed into a round bottom flask under $N_2$ atmosphere. First 300 ml benzene were added and subsequent 11 ml pyridine dropwise. The mixture was stirred at room temperature and after one hour 100 ml chloroform were added. 3 hours later the mixture was sonicated for 40 min and subsequent again 100 ml chloroform were added and the mixture was further stirred for 0.5 days at room temperature. Then 250 ml $H_2O$ and 100 ml chloroform were added to the mixture. The organic phase was dried and the solvent was removed at a rotovap. The crude product was dissolved in 100 ml dichloromethane/methanol 9:1 and subsequent purified by column chromatography on silica gel (eluent: dichloromethane/methanol 9:1) and recrystallization from ether and petrol ether. The final product was characterized by $^1$H-NMR.

C. Synthesis of C3Mo3

6 g Malonic acid mono cholesteryl ester was weighed into a round bottom flask and under $N_2$ atmosphere and at room temperature, 200 ml tetrahydrofurane, 2.2 ml 4-(2-Aminopropyl)-morpholine and 2.8 ml N-Methylmorpholine were added. The mixture was stirred and cooled down to 0° C. Then, 8.2 g TBTU were added stepwise and the reaction was allowed to stir at room temperature for 1 day. The suspension was pre-purified by filtering the mixture through a frit filled with silica gel (eluent: acetic acid ethyl ester/methanol 1:1).

Finally the crude product was purified by column chromatography on silica gel (eluent: chloroform/methanol 9:1) and the resulting product was characterized by $^1$H-NMR and LC-MS.

Synthesis of C3Mo2

6 g Malonic acid mono cholesteryl ester was weighed into a round bottom flask and under $N_2$ atmosphere and at room temperature, 200 ml Tetrahydrofuran, 2.0 ml 4-(2-Aminoethyl)-morpholine and 2.8 ml N-Methylmorpholine were added. The mixture was stirred and cooled down to 0° C. Then, 8.2 g TBTU were added stepwise and the reaction was allowed to stir at room temperature for 2 days. The suspension was pre-purified by filtering the mixture through a frit filled with silica gel (eluent: acetic acid ethyl ester/methanol 1:1). Finally the crude product was purified by chromatography on silica gel (1. chromatography→eluent: chloroform/methanol 9:1; 2. chromatography→eluent: chloroform/0-3% methanol). The resulting product was characterized by $^1$H-NMR and LC-MS.

Synthesis of C4Mo4

A. Synthesis of 4-Morpholin-4-yl-butyronitrile 196.9 ml morpholine, 500 ml toluol and 100 ml chloroform were stirred in a round-bottomed flask under $N_2$ atmosphere and at 80° C. After one hour 100 g 4-chlorobutyronitrile was added dropwise within one hour. The reaction was stirred one day at 80° C. and another day at room temperature. The mixture was fritted and the residue was washed two times with ether. The filtrate was concentrated and finally distilleed under vacuum. The product fractions were collected at 95-100° C. and 1.2-0.89 Torr. The purity of the colourless oil was judged by gas chromatography and $^1$H-NMR.

B. Synthesis of 4-Morpholin-4-yl-butylamine 14.8 g lithium aluminium hydride were weighed under $N_2$ atmosphere into a round-bottomed flask. The substance was cooled down to −55° C. and 150 ml ether was added dropwise. The suspension was allowed to stir; then 30 g 4-Morpholin-4-yl-butyronitrile were dissolved in 200 ml ether and the solution was added dropwise to the reaction mixture. Again 200 ml ether were added to the mixture and the reaction was stirred at room temperature overnight. At the next day the mixture was cooled down to less than 10° C. and 35 ml $H_2O$ were added carefully. After five hours the mixture was fritted and the residue was washed with 300 ml ether. The filtrate was dried, concentrated and finally distilled under vacuum. The product fractions were collected at 74-78° C. and 2.1-1.6 Torr. The purity of the colourless oil was judged by gas chromatography, GC-MS and $^1$H-NMR.

C. Synthesis of C4Mo4

9.7 g cholesterol hemissuccinate were dissolved in 100 ml tetrahydrofurane and stirred under $N_2$ atmosphere and at −15° C. Then 3.3 ml N-Methylmorpholine were added dropwise within 10 min followed by the slow addition of 2.9 ml isobutyl chloroformiate. Then 3.2 g 4-Morpholin-4-yl-butylamine were added dropwise. The temperature was raised to room temperature and the reaction was allowed to stir for 2.5 hours. The mixture was fritted and the residue was washed with 20 ml tetrahydrofurane. The solvent of the filtrate was evaporated and to the residue 100 ml boiling acetic acid ethyl ester was added. After a further filtration the mixture was kept at room temperature for 2.5 days. The solvent was again removed and the crude product was purified by column chromatography on silica gel (eluent: dichloromethane/methanol 96:4 and 83:17). The product was characterized by thin layer chromatography and $^1$H-NMR.

Synthesis of C5Mo2

A. Synthesis of Pentanedioic Acid Mono Cholesteryl Ester 35 g cholesterol and 15.5 g glutaric anhydride were weighed into a round-bottomed flask. Under $N_2$ atmosphere 500 ml chloroform, 25.4 ml triethylamine and 0.22 g 4-dimethylamino pyridine were added. The reaction was refluxed for 5 days. Then 250 ml $H_2O$ were added and the pH was adjusted under stirring to pH 4-5 with 2N HCl. The organic phase was dried and finally evaporated. To the residue again 31 g glutaric anhydride were added together with 250 ml toluol, 22.1 ml pyridine and 0.22 g 4-dimethylamino pyridine. The mixture was allowed to reflux for 1 day. Then the solvent was evaporated and the residue was dissolved in dichloromethane/acetic acid ethylester (96:4) and purified by a frit on silica gel (eluent: dichloromethane/methanol 94:4). After further purification by column chromatography on silica gel (eluent: product was characterized by $^1$H-NMR and thin layer chromatography.

B. Synthesis of C5Mo2

Under N2 atmosphere 6 g pentanedioic acid mono cholesteryl ester were dissolved in 250 ml tetrahydrofurane. 2.8 ml 4-(2-Aminoethyl)morpholin and 2.6 ml N-Methylmorpholin were added and the mixture was cooled down to 10° C. Finally 7.7 g TBTU were added stepwise and the reaction was allowed to stir at room temperature for one day followed by an incubation at 4° C. for 3 days. Then the solvent was evaporated and the crude product was purified by column chromatography on silica gel and characterized by 1H-NMR.

Synthesis of C6Mo2

A. Synthesis of Oxepane-2,7-dione 100 g adipinic acid and 100 ml acetanhydride were refluxed for 5 hours. The solvent was removed at a rotovap and 100 ml acetonitrile were added to the residue and the mixture was kept in a freezer over night. Then the mixture was fritted and the resulting residue was washed with 50 ml acetonitrile and dried.

B. Synthesis of Hexanedioic Acid Mono Cholesteryl Ester 65 g cholesterol and 33 g oxepane-2,7-dione were weighed into a round-bottomed flask. Under $N_2$ atmosphere 300 ml toluol, 21.2 ml pyridine and 0.21 g 4-dimethylamino pyridine were added. The reaction was refluxed for 2 days. Then the solvent was evaporated and the residue was dissolved in dichloromethane/acetic acid ethylester (96:4) and purified by a frit on silica gel (eluent: dichloromethane/acetic acid ethyl ester (96:4). The product was characterized by $^1$H-NMR and thin layer chromatography.

C. Synthesis of C6Mo2

Under N2 atmosphere 10 g hexanedioic acid mono cholesteryl ester were dissolved in 250 ml tetrahydrofurane. 3.1 ml 4-(2-Aminoethyl)morpholin and 3.2 ml N-Methylmorpholin were added and the mixture was cooled down to 10° C. After the addition of further 100 ml tetrahydrofurane 9.4 g TBTU were added stepwise and the reaction was allowed to stir at room temperature overnight. Then the solvent was evaporated and the crude product was purified by column chromatography on silica gel (eluent: choloroform/0-5% methanol) and characterized by $^1$H-NMR, thin layer chromatography and LC-MS.

Example 17

Amphoteric Liposomes Encapsulating siRNA siRNA-loaded amphoteric liposomes were manufactured using non-targeting scrambled siRNA. The lipid mixtures A (DC-Chol:DMGS:Chol, 26:39:35 mol %) or B (DC-Chol:DMGS:Chol, 20:40:40 mol %) were dissolved at a concentration of 30 mM or 60 mM (final lipid concentration) for both mixtures in ethanol. Appropriate volumes of siRNA stock were diluted in 20 mM NaAc, 300 mM Sucrose/NaOH pH 4.0. The organic and the aqueous solution were mixed in a 3:7 ratio and the liposomal suspension was immediately shifted to pH >7.5 with 136 mM $Na_2HPO_4$, 100 mM NaCl.

The amount of unencapsulated siRNA was determined by using ultrafiltration with Centrisart (Molecular Weight Cut off 300 kD (Sartorius, Göttingen, Germany)). The siRNA concentration of the filtrate was measured spectroscopically (OD 260 nm). The amount of encapsulated oligonucleotide was determined by subtraction of unencapsulated amount of siRNA from the total amount of siRNA.

Particle Characteristics after Manufacturing:

| Formulation | Initial lipid concentration | Size // Polydispersity index | Encapsulation efficacy |
| --- | --- | --- | --- |
| A | 30 mM | 256 nm // 0.319 | 63% |
| A | 60 mM | 313 nm // 0.490 | 64% |
| B | 30 mM | 184 nm // 0.055 | 69% |
| B | 60 mM | 206 nm // 0.135 | 77% |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising a cationic amphiphile selected from the group consisting of 4-(2-aminoethyl)-morpholino-cholesterol-2,3-dimethylhemisuccinate (DmC4Mo2), 4-(2-aminoethly)-morpholino-cholesterol-2,3-dimethylhemimalonate (DmC3Mo2), 4-(2-aminobutyl)-morpholino-cholesterol-hemisuccinate (C4Mo4), 4-(2-aminopropyl)-morpholino-cholesterol-hemimalonate (C3Mo3), 4-(2-aminoethyl)-morpholino-cholesterol-hemimalonate (C3Mo2), 4-(2-aminoethyl)-morpholino-cholesterol-hemiglutarate (C5Mo2), 4-(2-aminoethyl)-morpholino-cholesterol-hemiadipate (C6Mo2) and 4-(2-aminoethyl)-morpholino-cholesterol-hemiadipate (C8Mo2).

2. A composition comprising a compound of claim 1 combined with an anionic amphiphile.

3. The composition of claim 2, wherein the anionic amphiphile is selected from the group consisting of cholesterol hemisuccinate CHEMS, Dimyristoylglycerolhemisuccinate DMGS, Dimyristoylglycerolhemimalonate DMGM, Dimyristoylglycerolhemiglutarate DMGG, Dimyristoylglycerolhemiadipate DMGA, 4-((1,2-Dimyristoyl-ethyl)amino)-4-oxobutanoic acid DMAS, 4-((1,2-Dimyristoyl-ethyl)amino)-4-oxopropanoic acid DMAM, 4-((1,2-Dirnyristoyl-ethyl)amino)-4-oxopentanoic acid DMAG, 4-((1,2-Dimyristoyl-ethyl)amino)-4-oxohexanoic acid DMAA, Dioleoylglycerolhemisuccinate DOGS, Dioleoylglycerolhemimalonate DOGM, Dioleoylglycerolhemiglutarate DOGG, Dioleoylglycerolhemiadipate DOGA, 4-((1,2-Dioleoyl-ethyl)amino)-4-oxobutanoic acid DOAS, 4-((1,2-Dioleoyl-ethyl)amino)-4-oxopropanoic acid DOAM, 4-((1,2-Dioleoyl-ethyl)amino)-4-oxopentanoic acid DOAG, 4-((1,2-Dioleoyl-ethyl)amino)-4-oxohexanoic acid DOAA, 5,6-Dimyristoyl-hexanoic acid DMS, 4,5-Dimyristoyl-pentanoic acid DMM, 6,7-Dimyristoyl-heptanoic acid DMG, 7,8-Dioleoyl-octanoic acid DMA, 5,6-Dioleoyl-hexanoic acid DOS, 4,5-Dioleoyl-pentanoic acid DOM, 6,7-Dioleoyl-heptanoic acid DOG, 7,8-Dioleoyl-octanoic acid DOA, Cholesterolhemimalonate Chol-C3, Cholesterolhemiglutarate Chol-C5, and Cholesterolhemiadipate Chol-C6.

4. The composition of claim 2, further comprising a neutral or zwitterionic amphiphile.

5. The composition of claim 4, wherein the neutral or zwitterionic amphiphile is selected from the group consisting of phosphatidylcholines, sphingomyelins, ceramides, phosphatidylethanolamines, cholesterol and mixtures thereof.

6. The composition of claim 2, wherein the composition has an isoelectric point of from pH 4 to pH 8.

7. The composition of claim 4, wherein
the neutral or zwitterionic amphiphiles are less than 50 mol % of the composition; and
the composition has an isoelectric point of from pH 4 to pH 8.

8. The composition of claim 4, wherein the composition comprises an amphoteric liposome.

9. The composition of claim 4, wherein the isoelectric point is from pH 5 to pH 7.

10. The composition of claim 4, wherein the composition adopts a stable lamellar phase at from pH 7 to pH 8.

11. The composition of claim 4, wherein the molar ratio of the cationic amphiphile to the anionic amphiphile is greater than or equal to 1.

12. The composition of claim 4, wherein the neutral or zwitterionic amphiphiles are less than 40 mol % of the composition.

13. The composition of claim 4, wherein the composition comprises liposomes that encapsulate at least one active agent.

14. The composition of claim 13, wherein the at least one active agent is a nucleic acid.

15. The composition of claim 4, wherein the neutral or zwitterionic amphiphiles are selected from the group consisting of phosphatidylcholines, sphingomyelins, ceramides, phosphatidylethanolamines, cholesterols, and mixtures thereof.

16. The composition of claim 4, wherein the neutral or zwitterionic amphiphile is DOPE or Cholesterol.

17. The composition of claim 4, further comprising a counter-cation.

18. The composition of claim 17, wherein the counter-cation is selected from the group consisting of sodium, tris (hydroxymethyl)aminomethane, tris-hydroxyethylaminomethane and triethylamine.

* * * * *